US012649925B2

(12) United States Patent
Kumar et al.

(10) Patent No.: US 12,649,925 B2
(45) Date of Patent: \*Jun. 9, 2026

(54) TISSUE-SPECIFIC EXPRESSION AND HYBRID PLANT PRODUCTION

(71) Applicant: Dow AgroSciences LLC, Indianapolis, IN (US)

(72) Inventors: Sandeep Kumar, Carmel, IN (US); Marcelo Ariel German, Portland, OR (US); Tristan E Coram, Zionsville, IN (US); Terry R. Wright, Westfield, IN (US)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 949 days.

This patent is subject to a terminal disclaimer.

(21) Appl. No.: 17/166,285

(22) Filed: Feb. 3, 2021

(65) Prior Publication Data

US 2021/0171968 A1     Jun. 10, 2021

Related U.S. Application Data

(60) Continuation of application No. 16/046,780, filed on Jul. 26, 2018, now Pat. No. 10,913,953, which is a division of application No. 14/577,887, filed on Dec. 19, 2014, now Pat. No. 10,683,513.

(60) Provisional application No. 61/922,603, filed on Dec. 31, 2013.

(51) Int. Cl.
*C12N 15/82* (2006.01)

(52) U.S. Cl.
CPC ..... *C12N 15/8218* (2013.01); *C12N 15/8217* (2013.01); *C12N 15/8222* (2013.01); *C12N 15/8231* (2013.01); *C12N 15/8274* (2013.01); *C12N 15/8289* (2013.01)

(58) Field of Classification Search
None
See application file for complete search history.

(56) References Cited

U.S. PATENT DOCUMENTS

| | | | |
|---|---|---|---|
| 5,135,867 A | 8/1992 | Payne et al. | |
| 5,273,894 A | 12/1993 | Strauch et al. | |
| 5,316,931 A | 5/1994 | Donson et al. | |
| 5,463,175 A | 10/1995 | Barry et al. | |
| 5,500,360 A | 3/1996 | Ahlquist et al. | |
| 5,561,236 A | 10/1996 | Leemans et al. | |
| 5,589,367 A | 12/1996 | Donson et al. | |
| 5,608,147 A | 3/1997 | Kaphammer | |
| 5,637,489 A | 6/1997 | Strauch et al. | |
| 5,646,024 A | 7/1997 | Leemans et al. | |
| 5,648,477 A | 7/1997 | Leemans et al. | |
| 5,879,903 A | 3/1999 | Strauch et al. | |
| 5,910,626 A | 6/1999 | Haselkorn et al. | |
| 6,087,563 A | 7/2000 | Dellapenna et al. | |
| 6,107,549 A | 8/2000 | Feng et al. | |
| 6,153,401 A | 11/2000 | Streber et al. | |
| 6,268,547 B1 | 7/2001 | Weeks | |
| 6,518,222 B2 | 2/2003 | Arndt et al. | |
| 7,112,665 B1 | 9/2006 | Leemans et al. | |
| 7,250,561 B1 | 7/2007 | Pallett et al. | |
| 7,405,074 B2 | 7/2008 | Castle et al. | |
| 7,462,481 B2 | 12/2008 | Castle et al. | |
| 7,659,448 B2 | 2/2010 | Ahrens et al. | |
| 7,838,733 B2 * | 11/2010 | Wright ................. | C12N 9/0069 800/300 |
| 7,863,503 B2 | 1/2011 | Castle et al. | |
| 7,998,703 B2 | 8/2011 | Castle et al. | |
| 8,222,489 B2 | 7/2012 | Castle et al. | |
| 8,598,413 B2 | 12/2013 | Cui et al. | |
| 9,074,007 B2 | 7/2015 | Danilevskaya et al. | |
| 9,127,289 B2 | 9/2015 | Wright et al. | |
| 10,174,337 B2 | 1/2019 | Wright et al. | |
| 10,683,513 B2 | 6/2020 | Sandeep et al. | |
| 10,913,953 B2 | 2/2021 | Sandeep et al. | |
| 10,947,555 B2 | 3/2021 | Wright et al. | |
| 2001/0023501 A1 | 9/2001 | Johal et al. | |
| 2002/0059659 A1 | 5/2002 | Stemmer | |
| 2003/0041357 A1 | 2/2003 | Jepson et al. | |
| 2003/0056245 A1 | 3/2003 | Chatterjee et al. | |
| 2003/0135879 A1 | 7/2003 | Weeks et al. | |
| 2007/0199095 A1 | 8/2007 | Allen et al. | |
| 2007/0300329 A1 | 12/2007 | Allen et al. | |
| 2009/0069182 A1 | 3/2009 | Castle et al. | |
| 2009/0093366 A1 * | 4/2009 | Wright ............... | C12N 15/8209 800/300 |
| 2012/0054919 A1 | 3/2012 | Allen et al. | |

(Continued)

FOREIGN PATENT DOCUMENTS

| | | |
|---|---|---|
| AU | 2006203892 A1 | 7/2006 |
| AU | 2009267007 A1 | 1/2010 |

(Continued)

OTHER PUBLICATIONS

Chuck et al Development, 2010, 137:1243-1250. (Year: 2010).*

(Continued)

*Primary Examiner* — Brent T Page
*Assistant Examiner* — Aleksandar Radosavljevic

(57) ABSTRACT

This disclosure concerns the use of endogenous plant RNAi machinery to preferentially or specifically reduce transgene expression. In some embodiments, the disclosure concerns specific reduction of transgene expression in male plant tissues, for example, to provide an economical male sterility system of hybrid seed production.

17 Claims, 8 Drawing Sheets

Specification includes a Sequence Listing.

(56) References Cited

U.S. PATENT DOCUMENTS

| | | | |
|---|---|---|---|
| 2012/0245339 A1 | 9/2012 | Castle et al. | |
| 2013/0007908 A1* | 1/2013 | Huang | C12N 15/8218 |
| | | | 800/278 |
| 2014/0325713 A1 | 10/2014 | Kovalic et al. | |
| 2015/0184178 A1* | 7/2015 | Kumar | C12N 15/8217 |
| | | | 536/23.6 |
| 2016/0108422 A1 | 4/2016 | Ellis et al. | |

FOREIGN PATENT DOCUMENTS

| | | | |
|---|---|---|---|
| CA | 2746892 A1 | 7/2010 | |
| CN | 101466837 A | 6/2009 | |
| CN | 102304520 A | 1/2012 | |
| EP | 1025250 A2 | 8/2000 | |
| EP | 1167531 A1 | 1/2002 | |
| EP | 1824967 A2 | 8/2007 | |
| EP | 1740039 B1 | 6/2012 | |
| EP | 2535414 A1 | 12/2012 | |
| JP | 2005287415 A | 10/2005 | |
| RU | 2129005 C1 | 4/1999 | |
| WO | 8705629 A1 | 9/1987 | |
| WO | 9013654 A1 | 11/1990 | |
| WO | 9633270 A1 | 10/1996 | |
| WO | 9713402 A1 | 4/1997 | |
| WO | 9802562 A2 | 1/1998 | |
| WO | 9808963 A1 | 3/1998 | |
| WO | 9820144 A2 | 5/1998 | |
| WO | 9838294 A1 | 9/1998 | |
| WO | 9838336 A1 | 9/1998 | |
| WO | 9844139 A1 | 10/1998 | |
| WO | 9910513 A1 | 3/1999 | |
| WO | 9963092 A1 | 12/1999 | |
| WO | 0006757 A1 | 2/2000 | |
| WO | 0009727 A2 | 2/2000 | |
| WO | 0066748 A1 | 11/2000 | |
| WO | 0138513 A2 | 5/2001 | |
| WO | 03013224 A2 | 2/2003 | |
| WO | 03034813 A2 | 5/2003 | |
| WO | 03056904 A2 | 7/2003 | |
| WO | 2005107437 A2 | 11/2005 | |
| WO | 2005122751 A1 | 12/2005 | |
| WO | 2006111512 A1 | 10/2006 | |
| WO | 2007047016 A2 | 4/2007 | |
| WO | 2007091099 A1 | 8/2007 | |
| WO | 2008133643 A3 | 5/2009 | |
| WO | 2011067745 A2 | 6/2011 | |
| WO | 2013184768 A1 | 12/2013 | |

OTHER PUBLICATIONS

Müller et al 2006, Applied and Environmental Microbiology, 72: 4853-4861 (Year: 2006).*
White et al 2010, PNAS 107: 20240-20245 (Year: 2010).*
Chekan et al 2019, PNAS 116: 13299-13304 (Year: 2019).*
Muller et al.2006b (Protein Science 15:1356-1368) (Year: 2006).*
IPR2023-01036 (available in unredacted form to Applicant) (Year: 2024).*
IPR2023-01037 (available in unredacted form to Applicant) (Year: 2024).*
IPR2023-01038 (available in unredacted form to Applicant) (Year: 2024).*
Arif M.A., et al., "DICER-LIKE3 Activity in Physcomitrella Patens DICER-LIKE4 Mutants Causes Severe Developmental Dysfunction and Sterility," Molecular Plant, Nov. 2012, vol. 5, No. 6, pp. 1281-1294, Advance Access Publication on Apr. 17, 2012.
Chuck G., et al., "The Maize SBP-box Transcription Factor Encoded by Tasselsheath4 Regulates Bract Development and the Establishment of Meristem Boundaries," Development and Stem Cells, 2010, vol. 137, No. 8, pp. 1243-1250.
Extended European Search Report for European Application No. 14876758.5, mailed Sep. 11, 2017, 10 Pages.

International Preliminary Report on Patentability for International Application No. PCT/US2014/073038, mailed Jul. 14, 2016, 12 Pages.
International Search Report and Written Opinion for International Application No. PCT/US2014/073038, mailed Apr. 27, 2015, 16 Pages.
Li D., et al., "Deep Sequencing of Maize Small RNAs Reveals a Diverse Set of MicroRNA in Dry and Imbibed Seeds," PloS one, Jan. 24, 2013, vol. 8, Issue. 1(e55107), 14 Pages.
Yi F., et al., "Genome-Wide Characterization of MicroRNA in Foxtail Millet (Setaria italica)," BMC Plant Biology, Dec. 13, 2013, vol. 13, No. 1, Article No. 212, 15 Pages, DOI: 10.1186/1471-2229-13-212, ISSN 1471-2229, XP021170735.
Zhang L., et al., "A Genome-Wide Characterization of MicroRNA Genes in Maize," PLOS Genetics, Nov. 20, 2009, vol. 5, Issue No. 11(e1000716), 16 Pages.
Wang S., et al., "Development and Validation of Vectors Containing Multiple siRNA Expression Cassettes for Maximizing the Efficiency of Gene Silencing," BMC Biotechnology, 2006, vol. 6, No. 50, pp. 1-7.
Ohkouchi Y., et al., "Cloning and Expression of DL-2-haloacid Dehalogenase Gene From Burkholderia Cepacia," Water Science and Technology, 2000, vol. 42, No. 7-8, pp. 261-268.
Park H-D., et al., "Genetic and Phenotypic Diversity of Dichlorprop-Degrading Bacteria Isolated from Soils," Journal of Microbiology, Seoul, Republic of Korea, 2003, vol. 41, No. 1, pp. 7-15.
Park I.H., et al., "Isolation and Characterization of 4-(2,4-dichlorophenoxy)Butyric Acid-Degrading Bacteria from Agricultural Soils," Journal of Microbiology and Biotechnology, Jan. 2003, vol. 13, No. 2, pp. 243-250.
Parker L.W., et al., "Kinetics of Microbial Decomposition of 2,4-D in Soil: Effects of Herbicide Concentration," Journal of Environmental Quality, Oct. 1982, vol. 11, No. 4, pp. 679-684.
Paulin M.M., et al., "Abundance and Expression of Enantioselective rdpA and sdpA Dioxygenase Genes during Degradation of the Racemic Herbicide (R,S)-2-(2,4-Dichlorophenoxy)Propionate in Soil," Applied and Environmental Microbiology, 2010, vol. 76, No. 9, pp. 2873-2883.
Paulin M.M., et al., "(R,S)-Dichlorprop Herbicide in Agricultural Soil Induces Proliferation and Expression of Multiple Dioxygenase-Encoding Genes in the Indigenous," Environmental Microbiology, 2011, vol. 13, pp. 1513-1523.
Perkins E.J., et al., "Use of Alcaligenes Eutrophus as a Source of Genes for 2,4-d Resistance in Plants," Weed Science, 1987, vol. 35, No. Suppl. 1, pp. 12-18.
Plumeier I., et al., "Importance of Different tfd Genes for Degradation of Chloroaromatics by Ralstonia Eutropha JMP134," Journal of Bacteriology, Aug. 2002, vol. 184, No. 15, pp. 4054-4064.
Poh R., et al., "2,4-Dichlorophenoxyacetate / .Alpha .- Ketoglutarate Dioxygenases from Burkholderia Cepacia 2a and Ralstonia Eutropha JMP134," Microbios, 2001, vol. 105, pp. 43-63.
Poh R.P-C., et al., "Complete Characterization of Tn5530 From Burkholderia Cepacia Strain 2a (plJB1) and Studies of 2,4-dichlorophenoxyacetate Uptake by the Organism," Plasmid, 2002, vol. 48, No. 1, pp. 1-12.
Poiger T., et al., "Environmental Behavior of the Chiral Herbicide Haloxyfop. 1. Rapid and Preferential Interconversion of the Enantiomers in Soil," Journal of Agricultural and Food Chemistry, 2015, vol. 63, No. 10, pp. 2583-2590.
Preston C., et al., "Multiple Resistance to Dissimilar Herbicide Chemistries in a Biotype OfLolium Rigidumdue to Enhanced Activity of Several Herbicide Degrading Enzymes," Pesticide Biochemistry and Physiology, 1996, vol. 54, No. 2, pp. 123-134.
Prins M., "Broad Virus Resistance in Transgenic Plants," Trends in Biotechnology, Sep. 1, 2003, vol. 21, No. 9, ISSN: 0167-7799, pp. 373-375.
Rousseaux S., et al., "Isolation and Characterisation of New Gram-negative and Gram-positive Atrazine Degrading Bacteria From Different French Soils," FEMS Microbiology Ecology, 2001, vol. 36, No. 2-3, pp. 211-222.
Saari R.E., et al., "Stereospecific Degradation of the Phenoxypropionate Herbicide Dichlorprop," Journal of Molecular Catalysis B: Enzymatic, 1999, vol. 6, No. 4, pp. 421-428.

(56) References Cited

OTHER PUBLICATIONS

Sambrook J., et al., "Molecular Cloning," A Laboratory Manual, Cold Spring Harbor Laboratory Press, Second Edition, 1989, vol. 2, 11.45, 3 Pages.

Schleinitz., et al., "Rhodoferax sp. P230 R-2,4-Dichlorophenoxypropionate Dioxygenase (rdpA) gene," complete eds., Database EMBL, Accession No. AF516751, Aug. 6, 2002, pp. 1-2.

Schleinitz K.M., et al., "Localization and Characterization of Two Novel Genes Encoding Stereospecific Dioxygenases Catalyzing 2(2,4-Dichlorophenoxy)propionate Cleavage in Delftia acidovorans MC1," Applied and Environmental Microbiology, Sep. 2004, vol. 70, No. 9, pp. 5357-5365.

Schleinitz K.M., et al., Sphingobium Hervbicidovorans R-2,4-Dichlorphenoxypropionate Dioxygenase (rdpA) Gene, Complete eds., Database EMBL, Accesion No. AF516752, Aug. 6, 2002, pp. 1-2.

Schneiderheinze J.M., et al., "Plant and Soil Enantioselective Biodegradation of Racemic Phenoxyalkanoic Herbicides," Chirality, 1999, vol. 11, No. 4, pp. 330-337.

Seifert S., et al., "Effect of Tillage on Microbial Characteristics and Herbicide Degradation in a Sharkey Clay Soil," Weed Science, 2001, vol. 49, No. 5, pp. 685-693.

Shaw L.J., et al., "Enhanced Mineralization of [U-14C]2,4-dichlorophenoxyacetic Acid in Soil From the Rhizosphere of Trifolium Pratense," Applied and Environmental Microbiology, Aug. 2004, vol. 70, No. 8, pp. 4766-4774.

Shimojo M., et al., "Analysis of Genes encoding the 2,4-Dichlorophenoxyacetic Acid Degrading Enzyme from Sphingomonas Agrestis 58-1," Journal of Bioscience and Bioengineering, 2008, vol. 108, No. 1, pp. 56-59.

Smejkal C.W., et al., "Substrate Specificity of chlorophenoxyalkanoic Acid-Degrading Bacteria is not Dependent upon Phylogenetically Related tfdA Gene Types," Biology and Fertility of Soils, Jun. 2001, vol. 33, No. 6, pp. 507-513.

Spencer T.M., et al., "Segregation of Transgenes in Maize," Plant Molecular Biology, 1992, vol. 18, pp. 201-210.

Streber W.R., et al., "Analysis, Cloning, and High-Level Expression of 2, 4-Dichlorophenixyacetic Monooxygenase Gene tfdA of Alcaligenes Eutrophus JMP134," Journal of Bacteriology, 1987, vol. 169, No. 7, pp. 2950-2955.

Streber W.R., et al., "Transgenic Tobacco Plants Expressing a Bacterial Detoxifying Enzyme Are Resistant to 2,4- D," Bio/ Technology, 1989, vol. 7, pp. 811-816, 4 Pages (Abstract Only).

Streber W.R., "Transgenic Tobacco Plants Expressing a Bacterial Detoxifying Enzyme Are Resistant to 2,4-d," Bio/ Technology, 1989, vol. 7, No. 8, pp. 811-816.

Suwa Y., et al., "Characterization of a Chromosomally Encoded 2,4-Dichlorophenoxyacetic Acid/Ketoglutarate Dioxygenase from Burkholderia sp. Strain RASC," Applied and Environmental Microbiology, Jul. 1996, vol. 62, No. 7, pp. 2464-2469.

Swiegers J.H., et al., "Carnitine Biosynthesis in Neurospora Crassa: Identification of a cDNA Coding for Epsilon-n- trimethyllysine Hydroxylase and Its Functional Expression in Saccharomyces Cerevisiae," FEMS Microbiology Letters, 2002, vol. 210, No. 1, pp. 19-23.

Tamura K., "Microbial Pesticide Degradations and Evolutionary Analysis of Degrading Enzymes," Nippon Noyaku Gakkaishi, 2001, vol. 26, No. 3, pp. 309-314, 9 Pages.

Tett V.A., et al., "Biodegradation of the Chlorophenoxy Herbicide (R)-(+)-Mecoprop by Alcaligenes Denitrificans," Biodegradation, 1997, vol. 8, No. 1, pp. 43-52.

Tett V.A., et al., "Enantioselective Degradation of the Herbicide Mecoprop [2-(2-methyl-4-chlorophenoxy) Propionic Acid] by Mixed and Pure Bacterial Cultures," FEMS Microbiology Ecology, 1994, vol. 14, No. 3, pp. 191-200.

Top E.M., et al., "Capture of a Catabolic Plasmid That Encodes Only 2,4-dichlorophenoxyacetic Acid:alpha- ketoglutaric Acid Dioxygenase (Tfda) by Genetic Complementation," Applied and Environmental Microbiology, Jul. 1996, vol. 62, No. 7, pp. 2470-2476.

Top E.M., et al., "Methane Oxidation as a Method to Evaluate the Removal of 2,4-dichlorophenoxyactic Acid (2,4-d) From Soil by Plasmid-mediated Bioaugmentation," FEMS Microbiology Ecology, 1999, vol. 28, No. 3, pp. 203-213.

Top E.M., et al., "The Role of Mobile Genetic Elements in Bacterial Adaptation to Xenobiotic Organic Compounds," Current Opinion in Biotechnology, 2003, No. 14, No. 3, pp. 262-269.

Travkin V.M., et al., "Characterization of an Intradiol Dioxygenase Involved in the Biodegradation of the Chlorophenoxy Herbicides 2,4-d and 2,4,5-t," FEBS Letters, 1997, vol. 407, No. 1, pp. 69-72.

UNIPROT: "R-2,4-Dichlorophenoxypropionate Dioxygenase ((R)-2-(2,4-Dichlo Oxoglutarate Dioxygenase," Database Accession No. Q8KSC8.2, RdpA Shingobium herbicidovorans, Sequence updated: Mar. 1, 2004, Oct. 31, 2006, 2 pages.

Vallaeys T., et al., "Isolation and Characterization of a Stable 2,4-Dichlorophenoxyacetic Acid Degrading Bacterium, Variovorax Paradoxus, using Chemostat Culture," Biotechnology Letters, Nov. 1998, vol. 20, No. 11, pp. 1073-1076.

Vallaeys T., et al., "PCR-RFLP Analysis of 16s rRNA, tfdA and tfdb Genes Reveals a Diversity of 2,4-d Degraders in Soil Aggregates," FEMS Microbiology Ecology, 1997, vol. 24, No. 3, pp. 269-278.

Vallaeys T., et al., "The Metabolic Pathway of 2,4-dichlorophenoxyacetic Acid Degradation Involves Different Families of tfda and tfdb Genes According to PCR-RFLP Analysis," FEMS Microbiology Ecology, 1996, vol. 20, No. 3, pp. 163-172.

Vedler E., et al., "Analysis of the 2,4-dichlorophenoxyacetic Acid-degradative Plasmid pEST4011of Achromobacter Xylosoxidans Subsp. Denitrificans Strain EST4002," Gene, 2000, vol. 255, No. 2, pp. 281-288.

Vedler E., et al., "TfdR, the LysR-type Transcriptional Activator, is Responsible for the Activation of the tfdCB Operon of Pseudomonas Putida 2,4-Dichlorophenoxyacetic Acid Degradative Plasmid pEST4011," Gene, 2000, vol. 245, No. 1, pp. 161-168.

Vedler E., et al., "The Completely Sequenced Plasmid pEST4011 Contains a Novel IncP1 Backbone and a Catabolic Transposon Harboring tfd Genes for 2,4-Dichlorophenoxyacetic Acid Degradation," Journal of Bacteriology, Nov. 2004, vol. 186, No. 21, pp. 7161-7174.

Velicer G.J., "Pleiotropic Effects of Adaptation to a Single Carbon Source for Growth on Alternative Substrates," Applied and Environmental Microbiology, Jan. 1999, vol. 65, No. 1, pp. 264-269.

Westendorf A., et al., "Kinetic Traits and Enzyme Form Patterns of (R)-2-(2,4-Dichlorophenoxy) propionate/Alpha-Ketoglutarate Dioxygenase (RdpA) after Expression in Different Bacterial Strains," Engineering in Life Sciences, 2006, vol. 6, No. 6, pp. 552-559.

Westendorf A., et al., "Purification and Characterisation of the Enantiospecific Dioxygenases from Delftia acidovorans MC1 Initiating the Degradation of Phenoxypropionate and Phenoxyacetate Herbicides," Jan. 1, 2003, vol. 23, XP055108279, pp. 3-17.

Westendorf A., et al., "The Two Enantiospecific Dichlorprop/Alpha-Ketoglutarate-Dioxygenases from Delftia Acidovorans MC1protein and Sequence Data of RdpA and SdpA," Microbiological Research, 2002, vol. 157, pp. 317-322.

Westendorf A., et al., "The Two Enantiospecific Dichlorprop/. Alpha.—Ketoglutarate-Dioxygenases from Delftia Acidovorans MC1Protein and Sequence Data of RdpA and SdpA," Microbiological Research, 2002, vol. 157, pp. 317-322, 1 Page (Abstract only).

Whiting A.K., et al., "Metal Coordination Environment of a Cu(II)-Substituted -Keto Acid-Dependent Dioxygenase That Degrades the Herbicide 2,4-D," Journal of the American Chemical Society, 1997, vol. 119, No. 14, pp. 3413-3414.

Wu X., et al., "Rapid Biodegradation of the Herbicide 2,4-Dichlorophenoxyacetic Acid by Cupriavidus Gilardii T-I," Journal of Agricultural and Food Chemistry, 2017, vol. 65, No. 18, pp. 3711-3720.

Yi H-R., et al., "Phylogenetic and Phenotypic Diversity of 4-chlorobenzoate-degrading Bacteria Isolated From Soils," FEMS Microbiology Ecology, 2000, vol. 31, No. 1, pp. 53-60.

(56)  References Cited

OTHER PUBLICATIONS

Zabaloy M.C., et al., "Isolation and Characterization of Indigenous 2,4-D Herbicide Degrading Bacteria from an Agricultural Soil in Proximity of Sauce Grande River, Argentina," Annals of Microbiology, 2014, vol. 64, No. 3, pp. 969-974.

Zaprasis A., et al., "Abundance of Novel and Diverse tfdA-Like Genes, Encoding Putative Phenoxyalkanoic Acid Herbicide-Degrading Dioxygenases, in Soil," Applied and Environmental Microbiology, Jan. 2010, vol. 76, No. 1, pp. 119-128.

Zhang B-H., et al., "In Vitro Assay for 2,4-D Resistance in Transgenic Cotton," In Vitro Cellular & Developmental Biology: Plant, March-Apr. 2001, vol. 37, No. 2, pp. 300-304.

Zhang B-H., et al., "Inheritance and Segregation of Exogenous Genes in Transgenic Cotton," Journal of Genetics, Aug. 2000, vol. 79, No. 2, pp. 71-75.

Zhang H., et al., "Two Dcm Gene Clusters Essential for the Degradation of Diclofopmethyl in a Microbial Consortium of Rhodococcus sp. JT-3 and Brevundimonas sp. JT-9," Journal of Agricultural and Food Chemistry, 2018, vol. 66, No. 46, pp. 12217-12226.

Zhang L., et al., "Enantioselective Catabolismof the Two Enantiomers of the Phenoxyalkanoic Acid Herbicide Dichlorprop by Sphingopyxis sp. DBS4," Journal of Agricultural and Food Chemistry, 2020, vol. 68, No. 26, ISSN: 0021-8561, pp. 6967-6976.

Zhang Y., et al., "Enantioselective Environmental Behavior of the Chiral Herbicide Fenoxaprop-Ethyl and Its Chiral Metabolite Fenoxaprop in Soil," Journal of Agricultural and Food Chemistry, 2010, vol. 58, No. 24, pp. 12878-12884.

Zipper C., et al., "Complete Microbial Degradation Of Both Enantiomers Of The Chiral Herbicide Mecoprop [(Rs)-2- (4-chloro-2-methylphenoxy)Propionic Acid] in an Enantioselective Manner By Sphingomonas herbicidovorans Sp. Nov," Applied and Environmental Microbiology, Dec. 1996, vol. 62, No. 12, pp. 4318-4322.

Zipper C., et al., "Enantioselective Uptake and Degradation of the Chiral Herbicide Dichlorprop [(Rs)-2-(2,4- dichlorophenoxy)propanoic Acid] by Sphingomonas Herbicidovorans MH," Journal of Bacteriology, Jul. 1998, vol. 180, No. 13, pp. 3368-3374.

Baelum J., et al., "Comparison of 16S rRNA Gene Phylogeny and Functional tfdA Gene Distribution in Thirty-One Different 2, 4-Dichlorophenoxyacetic Acid and 4-Chloro-2-Methylphenoxyacetic Acid Degraders," Systematic and Applied Microbiology, 2010, vol. 33, pp. 67-70 (Supplemental Material), 10 Pages.

Baelum J., et al., "Degradation of 4-Chloro-2-Methylphenoxyacetic Acid in Top- and Subsoil is Quantitatively Linked to the Class III tfdA Gene," Applied and Environmental Microbiology, Feb. 2006, vol. 72, pp. 1476-1486.

Baelum J., et al., "TaqMan Probe-Based Real-Time PCR Assay for Detection and Discrimination of Class I, II, and III tfdA Genes in Soils Treated with Phenoxy Acid Herbicides," Applied and Environmental Microbiology, May 2009, vol. 75, No. 9, pp. 2969-2972.

Bayley C., et al., "Engineering 2,4-D Resistance Into Cotton," Theoretical and Applied Genetics, Jan. 1, 1992, vol. 83, No. 5, pp. 645-649.

Bhat M.A., et al., "Purification of 3,5-dichlorocatechol 1,2-dioxygenase, a Nonheme Iron Dioxygenase and a Key Enzyme in the Biodegradation of a Herbicide, 2,4-dichlorophenoxyacetic Acid (2,4-d), From Pseudomonas Cepacia Csv90," Archives of Biochemistry and Biophysics, 1993, vol. 300, No. 2, pp. 738-746.

Bisht N.C., et al., "Development of 2,4-O-Resistant Transgenics in Indian Oilseed Mustard (Brassica Juncea)," Current Science, Aug. 10, 2004, vol. 87, No. 3, ISSN: 0011-3891, pp. 367-370.

Chaudhry G.R., et al., "Isolation and Characterization of a New Plasmid From a Flavobacterium Sp. Which Carries the Genes for Degradation of 2,4-dichlorophenoxyacetate," Journal of Bacteriology, 1988, vol. 170, No. 9, pp. 3897-3902.

Chen S., et al., "Reasons for the Acclimation for 2,4-D Biodegradation in Lake Water," Journal of Environmental Quality, Apr. 1989, vol. 18, No. 2, pp. 153-156.

Cho S.H., et al., "Isolation and Characterization of 2-Methyl-4-Chlorophenoxyacetic Acid-Degrading Bacteria from Agricultural Soils," Agricultural Chemistry and Biotechnology (English Edition), 1999, vol. 42, No. 2, pp. 57-61.

Cosper N.J., et al., "X-ray Absorption Spectroscopic Analysis of Fe(II) and Cu(II) Forms of a Herbicide-degrading Alpha-ketoglutarate Dioxygenase," Journal of Biological Inorganic Chemistry, 1999, vol. 4, No. 1, pp. 122-129.

Daane L.L., et al., "Earthworm Egg Capsules as Vectors for the Environmental Introduction of Biodegradative Bacteria," Applied and Environmental Microbiology, Jun. 1999, vol. 65, No. 6, pp. 2376-2381.

Dellaporta S.L., et al., "A Plant DNA Minipreparation: Version 11," Plant Molecular Biology Reporter, Jan. 1, 1983, vol. 1, No. 4, ISSN: 0735-9640, pp. 19-21.

Don R.H., et al., "Genetic and Physical Map of the 2,4-Dichlorophenoxyacetic Acid-Degradative Plasmid pJP4," Journal of Bacteriology, Jan. 1985, vol. 161, No. 1, pp. 466-468.

Donr.H., et al., "Transposon Mutagenesis and Cloning Analysis of the Pathways for Degradation of 2,4- Dichlorophenoxyacetic Acid and 3-Chlorobenzoate in Alcaligenes Eutrophus JMP134(pJP4)," Journal of Bacteriology, Jan. 1985, vol. 161, No. 1, pp. 85-90.

"sdpA MC1 Delftia Aciovorans," UniProtKB Accession No. P83309. 2, Sep. 18, 2019, 3 Pages.

Dunbar J., et al., "Genetic Diversity Through the Looking Glass: Effect of Enrichment Bias," Applied and Environmental Microbiology, Apr. 1997, vol. 63, No. 4, pp. 1326-1331.

Ehrig A., et al., "Isolation of Phenoxy Herbicide-Degrading Rhodoferax Species from Contaminated Building Material," Acta Biotechnologica, 1997, vol. 17, No. 4, pp. 351-356.

Eichhorn E., et al., "Characterization of Alpha-Ketoglutarate-Dependent Taurine Dioxygenase from Escherichia Coli," Journal of Biological Chemistry, Sep. 1997, vol. 272, No. 37, ISSN: 0021-9258, p. 23031-23036.

Feng L., et al., Biodegradation and Plant Protection From the Herbicide 2,4-D by Plant-microbial Associations in Cotton Production Systems, Biotechnology and Bioengineering, 1997, vol. 54, No. 6, pp. 513-519.

Fuchslin H.P., et al., "Effect of Integration of a Gfp Reporter Gene on Fitness of Ralstonia Eutropha During Growth With 2,4-dichlorophenoxyacetic Acid," Environmental Microbiology, Oct. 2003, vol. 5, No. 10, pp. 878-887.

Fukamori F., et al., Alcaligenes Eutrophus JMP134 "2,4-Dichlorophenoxyacetate Monooxygenase is an a-Ketoglutarate-Dependent Dioxygenase," Journal of Bacteriology, 1993, vol. 175, pp. 2083-2086.

Fukamori F., et al., "Purification and Characterization of 2,4-Dichlorophenoxyacetate/Alpha-Ketoglutarate Dioxygenase," Journal of Biological Chemistry, 1993, vol. 268, No. 32, pp. 24311-24317.

Gazitua M.C., et al., "Novel Alpha-Ketoglutarate Dioxygenase tfdA-Related Genes are found in Soil DNA after Exposure to Phenoxyalkanoic Herbicides," Environmental Microbiology, 2010, vol. 12, No. 9, pp. 2411-2425.

GenBank: "(S)-2-(2,4-dichlorophenoxy)propionate/alpha-ketoglutarate dioxygenase [Rhodoferax sp. P230]," GenBank Accession No. ABD67501.1, Mar. 14, 2006, 2 Pages.

Griffin S.L., et al., "Characterization Of Aryloxyalkanoate Dioxygenase-12, A Nonheme Fe(II)/Alpha.-Ketoglutarate- Dependent Dioxygenase, Expressed in Transgenic Soybean and Pseudomonas Fluorescens," Journal of Agricultural and Food Chemistry, 2013, vol. 61, pp. 6589-6596.

Han L., et al., "16S rRNA Gene Phylogeny and tfdA Gene Analysis of 2,4-D-Degrading Bacteria Isolated in China," World Journal of Microbiology & Biotechnology, 2014, vol. 30, No. 10, pp. 2567-2576.

Han L., et al., "Cloning, Expression, Characterization and Mutational Analysis of the tfdA Gene from Cupriavidus Campinensis BJ71," World Journal of Microbiology & Biotechnology, 2015, vol. 31, No. 7, pp. 1021-1030.

Harker A.R., et al., "Phenoxyacetic Acid Degradation by the 2,4-dichlorophenoxyacetic Acid (TFD) Pathway of Plasmid pJP4: Mapping and Characterization of the TFD Regulatory Gene, tfdR," Journal of Bacteriology, 1989, vol. 171, No. 1, pp. 314-320.

(56)                    References Cited

OTHER PUBLICATIONS

Hausinger R.P., "Biochemical Diversity of 2-0xoglutarate-Dependent Oxygenases," 2015, vol. 3, No. 1, pp. 1-58.

Hausinger R.P., et al., "Characterization of the First enzyme in 2,4-Dichlorphenoxyacetic Acid Metabolism," Environmental Health Perspectives, Jun. 1995, vol. 103, Supplement 5, pp. 37-39.

Hausinger R.P., et al., "Fe(II)/Alpha-Ketoglutarate-Dependent Hydroxylases and Related Enzymes," Critical Reviews in Biochemsitry, 2004, vol. 39, No. 1, pp. 21-68, 51 Pages.

Hawkins A.C., et al., "Chemotaxis of Ralstonia eutropha JMP134(pJP4) to the Herbicide 2,4- dichlorophenoxyacetate," Applied and Environmental Microbiology, Feb. 2002, vol. 68, No. 2, pp. 968-972.

Hegg E.L., et al., "Herbicide-Degrading Alpha-Keto Acid-Dependent Enzyme TfdA: Metal Coordination Environment and Mechanistic Insights," Biochemistry, Dec. 14, 1999, vol. 38, No. 50, ISSN 0006-2960, XP002549095, p. 16714-16726.

Hoffmann D., et al., "A Transposon Encoding the Complete 2,4-dichlorophenoxyacetic Acid Degradation Pathway in the Alkalitolerant Strain Delftia Acidovorans P4a," Microbiology, 2003, vol. 149, No. 9, pp. 2545-2556.

Hoffmann D., et al., "Development and Application of PCR Primers for the Detection of the Lid Genes in Delftia Acidovorans P4a Involved in the Degradation of 2,4-D," Acta Biotechnologica, 2001, vol. 21, No. 4, pp. 321-331.

Hogan D.A., et al., "Distribution of the Tfda Gene in Soil Bacteria That Do not Degrade 2,4-dichlorophenoxyacetic Acid (2,4-d)," Microbial Ecology, 1997, vol. 34, No. 2, pp. 90-96.

Hogan D.A., et al., "Site-directed Mutagenesis of 2,4-dichlorophenoxyacetic Acid/alpha-ketoglutarate Dioxygenase. Identification of Residues Involved in Metallocenter Formation and Substrate Binding," Journal of Biological Chemistry, 2000, vol. 275, No. 17, pp. 12400-12409.

Horvath M., et al., "Isolation and Characterization of a 2-(2,4-dichlorophenoxy) Propionic Acid-degrading Soil Bacterium," Applied Microbiology and Biotechnology, 1990, vol. 33, pp. 213-216, 1 Page (Abstract only).

Hotopp J.C.D., et al., "Alternative Substrates of 2,4-Dichlorophenoxyacetate/a-Ketoglutarate Dioxygenase," Journal of Molecular Catalysis B: Enzymatic, Nov. 1, 2001, vol. 15, No. 4-6, pp. 155-162.

Hotopp J.C.D., et al., "Probing the 2,4-Dichlorophenoxyacetate/Alpha-Ketoglutarate Dioxygenase Substrate-Binding Site by Site-Directed Mutagenesis and Mechanism-Based Inactivation," Biochemistry, 2002, vol. 41, No. 31, pp. 9787-9794.

Hulse J.D., et al., "Carnitine Biosynthesis Beta-Hydroxylation of Tri Methyl Lysine by an Alpha-Keto Glutarate Dependent Mitochondrial Dioxygenase," Journal of Biological Chemistry, Mar. 10, 1978, vol. 253, No. 5, ISSN: 0021-9258, pp. 1654-1659.

Itoh K., et al., "Root Nodule Bradyrhizobium spp. Harbor tfdA and cadA, Homologous with Genes Encoding 2,4- Dichlorophenoxyacetic Acid-Degrading Proteins," Applied and Environmental Microbiology, 2004, vol. 70, No. 4, pp. 2110-2118.

Itoh K., et al., "tfdA-like Genes in 2,4-Dichlorophenoxyacetic Acid-Degrading Bacteria Belonging to the Bradyrhizobium-Agromonas-Nitrobacter-Afipia Cluster in Proteobacteria," Applied and Environmental Microbiology, Jul. 2002, vol. 68, No. 7, pp. 3449-3454.

Jackman S.A., et al., "Electrokinetic Movement and Biodegradation of 2,4-dichlorophenoxyacetic Acid in Silt Soil," Biotechnology and Bioengineering, Jul. 5, 2001, vol. 74, No. 1, pp. 40-48.

Jing X., et al., "Enantioselective Toxicity and Degradation of Chiral Herbicidefenoxaprop-Ethyl in Earthworm Eisenia Fetida," Ecological indicators, 2017, vol. 75, pp. 126-131.

Ka J.O., et al., "Integration and Excision of a 2,4-dichlorophenoxyacetic Acid-degradative Plasmid in Alcaligenes Paradoxus and Evidence of Its Natural Intergeneric Transfer," Journal of Bacteriology, Sep. 1994, vol. 176, No. 17, 5284-5289.

Ka J.O., et al., "Use of Gene Probes to Aid in Recovery and Identification of Functionally Dominant 2,4- dichlorophenoxyacetic Acid-degrading Populations in Soil," Applied and Environmental Microbiology, Apr. 1994, vol. 60, No. 4, pp. 1116-1120.

Kaneko T., et al., "Complete Genomic Sequence of Nitrogen-Fixing Symbiotic Bacterium Bradyrhizobium Japonicum USDA110," Dna Research, 2002, vol. 9, pp. 189-197.

Kaneko T., et al., "Complete Genomic Sequence of Nitrogen-fixing Symbiotic Bacterium Bradyrhizobium Japonicum USDA110 (Supplement)," DNA Research, Nov. 18, 2002, vol. 9, No. 6, pp. 225-256 (Supplement).

Kitagawa W., et al., "Novel 2,4-Dichlorophenoxyacetic Acid Degradation Genes From Oligotrophic Bradyrhizobium Sp. Strain HW13 Isolated From a Pristine Environment," Journal of Bacteriology, Jan. 2002, vol. 184, No. 2, pp. 509-518.

Kleinsteuber S., et al., "Expression of the 2,4-d Degradative Pathway of pJP4 in an Alkaliphilic, Moderately Halophilic Soda Lake Isolate, Halomonas Sp. EF43," Extremophiles, 2001, vol. 5, No. 6, pp. 375-384.

Kohler H.P., et al., "Sphingomonas Herbicidovorans MH: a Versatile Phenoxyalkanoic Acid Herbicide Degrader," Genbank Accession No. Q8KSC8, Oct. 31, 2006, 2 Pages, First Published on Oct. 1, 2002.

Kohler H.P.E., "Sphingomonas Herbicidovorans Mh: A Versatile Phenoxyalkanoic Acid Herbicide Degrader," Journal of Industrial Microbiology and Biotechnology, 1999, vol. 23, XP002587234, pp. 336-340.

Kohler, "Sphingomonas Herbicidovorans tnpA Gene for Transposase and rdpA Gene for (R)-2- (2,4- Dichlorophenoxy) Propionate, 2-Oxoglutarate Dioxygenase," Database EMBL, Accesion No. AJ628859, Mar. 3, 2004, pp. 1-2.

Kraube J., et al., "Crystal Structure of the 2-Oxoglutarate Dependent Dioxygenase RdpA," 4th Biotechnology Symposium of the University of Leipzig (Abstract), Protein Engineering and Bioanalytics, 2005, 1 Page.

Kwon J.K., et al., "Expression of 2,4-Dichlorophenoxyacetic Acid Monooxygenase Gene in Tobacco Plants," Journal of Korean Society of Horticultural Science, 1997, vol. 38, No. 6, pp. 796-799.

Laemmli C., et al., "Mutation Analysis of the Different Tfd Genes for Degradation of Chloroaromatic Compounds in Ralstonia Eutropha JMP134," Archives of Microbiology, 2004, vol. 181, No. 2, pp. 112-121.

Larue C.T., et al., "Development of Enzymes for Robust Aryloxyphenoxypropionate and Synthetic Auxin Herbicide Tolerance Traits in Maize and Soybean Crops," Pest Management Science, 2019, vol. 75, No. 8, pp. 2086-2094.

Laurent F., et al., "2,4-Dichlorophenoxyacetic Acid Metabolism in Transgenic Tolerant Cotton (Gossypium hirsutum)," Journal of Agricultural and Food Chemistry, 2000, vol. 48, No. 11, pp. 5307-5311.

Leibeling S., et al., "Posttranslational Oxidative Modification of (R)-2- (2,4-dichlorophenoxy) Propionate/Alpha- Ketoglutarate-Dependent Dioxygenases (RdpA) Leads to Improved Degradation of 2,4-Dichlorophenoxyacetate (2,4- D)," Engineering in Life Sciences, 2013, vol. 13, No. 3, pp. 278-291.

Letouze A., et al., "Enhanced Activity of Several Herbicide-degrading Enzymes: a Suggested Mechanism Responsible for Multiple Resistance in Blackgrass (Alopecurus Myosuroides Huds.)," Agronomie, 2003, vol. 23, No. 7, pp. 601-608.

Lewis D.L., et al., "Influence of Environmental Changes on Degradation of Chiral Pollutants in Soils," Nature, 1999, vol. 401, No. 6756, pp. 898-901.

Lim J-S., et al., "Genetic and Phenotypic Diversity of (R/S)-Mecoprop [2-(2-Methyl-4-Chlorophenoxy)Propionic acid]- Degrading Bacteria Isolated from Soils," Journal of Microbiology, Seoul, Republic of Korea, 2004, vol. 42, No. 2, pp. 87-93.

Lipthay J.R.D., et al., "Enhanced Degradation of Phenoxyacetic Acid in Soil by Horizontal Transfer of the Tfda Gene Encoding a 2,4-dichlorophenoxyacetic Acid Dioxygenase," FEMS Microbiology Ecology, 2001, vol. 35, No. 1, pp. 75-84.

Lipthay J.R.D., et al., "Expression of Tfda Genes in Aquatic Microbial Communities During Acclimation to 2,4-Dichlorophenoxyacetic Acid," FEMS Microbiology Ecology, 2002, vol. 40, No. 3, pp. 205-214.

(56)                    References Cited

OTHER PUBLICATIONS

Lipthay J.R.D., et al., "In Situ Exposure to Low Herbicide Concentrations Affects Microbial Population Composition and Catabolic Gene Frequency in an Aerobic Shallow Aquifer," Applied and Environmental Microbiology, Jan. 2003, vol. 69, No. 1, pp. 461-467.

Liu Y.J., et al., "Consumers of 4-Chloro-2-Methylpheoxyacetic Acid from Ggricultural Soil and Drilosphere Harbor cadA, r/sdpA, and tfdA-like Gene Encoding Oxygenases," FEMS Microbiology Ecology, 2013, vol. 86, No. 1, pp. 114-129.

Llewellyn D., et al., "Genetic Engineering of Crops for Tolerance to 2,4-D," Herbicide-Resistant Crops, 1996, Chapter 10, pp. 159-174.

Loos M.A., et al., "Phenoxyacetate Herbicide Detoxication by Bacterial Enzymes," Journal of Agricultural and Food Chemistry, 1967, vol. 15, No. 5, pp. 858-860.

Ludwig P., et al., "Chromatographic Separation of the Enantiomers of Marine Pollutants. Part 5: Enantioselective Degradation of Phenoxycarboxylic Acid Herbicides by Marine Microorganisms," Chemosphere, 1992, vol. 24, No. 10, pp. 1423-1429.

Lyon B.R., et al., "Cotton Plants Transformed with a Bacterial Degradation Gene are Protected from Accidental Spray Drift Damage by the Herbicide 2,4-Dichlorophenoxyacetic Acid," Transgenic Research, 1993, vol. 2, No. 3, pp. 162-169.

Lyon B.R., et al., "Expression of a Bacterial Gene in Transgenic Tobacco Plants Confers Resistance to the Herbicide 2,4-dichlorophenoxyacetic Acid," Plant Molecular Biology, 1989, vol. 13, No. 5, pp. 533-540.

Mae A.A., et al., "Characterization of a New 2,4-dichlorophenoxyacetic Acid Degrading Plasmid pEST4011: Physical Map and Localization of Catabolic Genes," Journal of General Microbiology, 1993, vol. 139, No. 12, pp. 3165-3170.

Maltseva O., et al., "Degradation of 2,4-dichlorophenoxyacetic Acid by Haloalkaliphilic Bacteria," Microbiology, 1996, vol. 142, No. 5, pp. 1115-1122.

Marriott M.W., et al., "Biodegradation of Mixtures of Chlorophenoxyalkanoic Acid Herbicides by Alcaligenes Denitrificans," Journal of Industrial Microbiology & Biotechnology, 2000, vol. 25, No. 5, pp. 255-259.

Matheson V.G., et al., "Evidence for Acquisition in Nature of a Chromosomal 2,4-Dichlorophenoxyacetic Acid/ (alpha)-Ketoglutarate Dioxygenase Gene by Different Burkholderia spp," Applied and Environmental Microbiology, Jul. 1996, vol. 62, No. 7, pp. 2457-2463.

McGowan C., et al., "Evidence for Interspecies Gene Transfer in the Evolution of 2,4- Dichlorophenoxyacetic Acid Degraders," Applied and Environmental Microbiology, Oct. 1998, vol. 64, No. 10, pp. 4089-4092.

Mierzejewska E., et al., "Biodegradation Potential and Ecotoxicity Assessment in Soil Extracts Amended with Phenoxy Acid Herbicide (2,4-D) and a Structurally-Similar Plant Secondary Metabolite (Ferulic Acid)," Bulletin of Environmental Contamination and Toxicology, 2020, vol. 104, No. 2, pp. 200-205.

Mortensen S.K., et al., "Influence of Frozen Storage on Herbicide Degradation Capacity in Surface and Subsurface Sandy Soils," Environmental Science & Technology, 2004, vol. 38, No. 24, pp. 6625-6632.

Mueller R.H., et al., "Degradability and Recalcitrance of Phenoxyalkanoic Acid Herbicides—Traits of the Microbial Metabolism," In Second International Conference on Remediation of Chlorinated and Racalcitrant Compounds, 2000, pp. 229-236.

Mueller T.A., et al., "Insights into the Enantiospecificities of (R)- and (S)-Dichlorprop/a-Ketoglutarate Dioxygenases," Un Mich ICBIC, 2005, 3 Pages (Abstract).

Muller R.H., "Activity and Reaction Mechanism of the Initial Enzymatic Step Specifying the Microbial Degradation of 2,4-Dichlorophenoxyacetate," Engineering in Life Sciences, 2007, vol. 7, No. 4, pp. 311-321.

Muller R.H., et al., "Comamonas Acidovorans Strain Mc1. A New Isolate Capable of Degrading the Chiral Herbicides Dichlorprop and Mecoprop and the Herbicides 2,4-d and Mcpa," Microbiological Research, 1999, vol. 154, No. 3, pp. 241-246.

Muller R.H., et al., "Separation of Two Dichlorprop/a-ketoglutarate Dioxygenases With Enantiospecific Properties From Comamonas Acidovorans Mc1," Acta Biotechnologica, 1999, vol. 19, No. 4, pp. 349-355.

Muller R.H., et al., "Physiological and Genetic Characteristics of Two Bacterial Strains Utilizing Phenoxypropionate and Phenoxyacetate Herbicides," Microbiological Research, 2001, vol. 156, No. 2, pp. 121-131.

Muller R.H., et al., "Pseudo-Recalcitrance of Chlorophenoxyalkanoate Herbicides—Correlation to the Availability of Ketoglutarate," Acta Biotechnologica, 2001, vol. 21, No. 3, pp. 227-242.

Muller T.A., et al., "Genetic Analysis of Phenoxyalkanoic Acid Degradation in Sphingomonas Herbicidovorans MH," Applied and Environmental Microbiology, Oct. 2004, vol. 70, No. 10, pp. 6066-6075.

Muller T.A., "Metabolism of Phenoxyalkanoic Acid Herbicides in Sphingomonas Herbicidovorans Mh Cloning And Characterization of Two Enantiospecific -ketoglutarate-dependent Dioxygenases and Degradation Pathway Analysis," Swiss Federal Institute of Technology Thesis, Nov. 2004, 182 Pages.

Ncbi: "2,4-D Dioxygenase (Plasmid) [Burkholderia Cepacia]," GenBank Accession No. AAB47567.1, Jul. 26, 2016, 1 Page.

NCBI: "2,4-D/Alpha-ketoglutarate Dioxygenase [Delftia Acidovorans]," GenBank Accession No. AAM76772.1, Jul. 26, 2016, 2 Pages.

NCBI: "2,4-D/Alpha-ketoglutarate Dioxygenase (Plasmid) [Burkholderia Cepacia]," GenBank Accession No. AAK81681.1, Jul. 23, 2016, 2 Pages.

NCBI: "2,4-Dichlorophenoxyacetate Monooxygenase (Gtg Start Codon) [Cupriavidus Necator]," GenBank Accession No. AAA21983.1, Apr. 26, 1993, 1 Page.

NCBI: "A. eutrophus 2, Dichlorophenoxyacetate Monooxygenase Gene, Complete Cds," GenBank Database Accession No. M16730, Apr. 26, 1993, 2 Pages.

NCBI: "Alpha KG dependent 2,4-D Dioxygenase [Alpha Proteobacterium HW13]," GenBank Accession No. BAB92966.1, Jul. 2, 2002, 1 page.

NCBI: "Alpha KG dependent 2,4-D Dioxygenase [Alpha Proteobacterium HWK12]," GenBank Accession No. BAB92965.1, Jul. 2, 2002, 1 Page.

NCBI: "Alpha KG dependent 2,4-D Dioxygenase [Alpha Proteobacterium RD5-C2]," GenBank Accession No. BAB92964.1, Jul. 2, 2002, 1 Page.

NCBI: "RecName: Full=Alpha-ketoglutarate-dependent 2,4-dichlorophenoxyacetate Dioxygenase; Short=2,4-D Dioxygenase," UniProtKB Accession No. Q45423.1, Aug. 12, 2020, 2 Pages.

NCBI: "TfdA (Plasmid) [Achromobacter Denitrificans]," GenBank Accession No. AAS49436.1, Apr. 3, 2020, 2 Pages.

Nickel K., et al., "Involvement of Two Alpha-ketoglutarate-dependent Dioxygenases in Enantioselective Degradation of (R)- and (S)-mecoprop by Sphingomonas Herbicidovorans MH," Journal of Bacteriology, 1997, vol. 179, No. 21, pp. 6674-6679.

Nielsen T.K., et al., "Novel Insight into the Genetic Context of the cadAB Genes from a 4-Chloro-2-Methylphenoxyacetic Acid-Degrading Sphingomonas," PLOS One, 2013, vol. 8, No. 12, e83346, pp. 1-9.

* cited by examiner

| Level | | Mean |
|---|---|---|
| 112377 | A | 302.66667 |
| 113016 | A | 301.66667 |
| 112376 | A | 282.66667 |
| 112375 | B | 58.00000 |
| Negative Control | B | 0.00000 |
| YFP Control | B | 0.00000 |

Levels not connected by same letter are significantly different.

AAD1 is repressed in 112375 presumably due to high abundance of miR156 in corn immature embryos

| Level | | Mean |
|---|---|---|
| 113021 | A | 1730.5000 |
| 113019 | B | 341.5400 |
| 113020 | B | 190.3000 |
| 113018 | B | 145.8571 |

Levels not connected by same letter are significantly different.

| Level | | Mean |
|---|---|---|
| 113021 | A | 201.45000 |
| 113019 | A  B | 140.10000 |
| 113020 | A  B | 117.37500 |
| 113018 | B | 110.21875 |

Levels not connected by same letter are significantly different.

| Level | | Mean |
|---|---|---|
| 113018 | A | 0.37052632 |
| 113021 | A | 0.34000000 |
| 113020 | A | 0.29454545 |
| 113019 | A | 0.26111111 |

Levels not connected by same letter are significantly different.

| Level | | Mean |
|---|---|---|
| 113021 | A | 2.4233333 |
| 113020 | B | 0.7600000 |
| 113019 | B | 0.7520000 |
| 113018 | B | 0.4200000 |

Levels not connected by same letter are significantly different.

```
                          SEQUENCE LISTING

<160> NUMBER OF SEQ ID NOS: 38

<210> SEQ ID NO 1
<211> LENGTH: 20
<212> TYPE: RNA
<213> ORGANISM: Artificial
<220> FEATURE:
<223> OTHER INFORMATION: exemplary miR156 RNA

<400> SEQUENCE: 1
ugacagaaga gagugagcac                                                   20

<210> SEQ ID NO 2
<211> LENGTH: 21
<212> TYPE: RNA
<213> ORGANISM: Artificial
<220> FEATURE:
<223> OTHER INFORMATION: exemplary miR529 RNA

<400> SEQUENCE: 2
agaagagaga gaguacagcc u                                                 21

<210> SEQ ID NO 3
<211> LENGTH: 20
<212> TYPE: RNA
<213> ORGANISM: Artificial
<220> FEATURE:
<223> OTHER INFORMATION: miR319 RNA

<400> SEQUENCE: 3
uuggacugaa gggugcuccc                                                   20

<210> SEQ ID NO 4
<211> LENGTH: 35
<212> TYPE: DNA
<213> ORGANISM: Artificial
<220> FEATURE:
<223> OTHER INFORMATION: tsh4 miR529-156 DNA target site

<400> SEQUENCE: 4
gactccagct gtgctctctc tcttctgtca actca                                  35

<210> SEQ ID NO 5
<211> LENGTH: 1296
<212> TYPE: DNA
<213> ORGANISM: Artificial
<220> FEATURE:
<223> OTHER INFORMATION: pDAB113016 expression cassette
<220> FEATURE:
<221> NAME/KEY: misc_feature
<222> LOCATION: (889)..(1296)
<223> OTHER INFORMATION: ZmPer5 3'UTR

<400> SEQUENCE: 5
atggctcatg ctgccctcag ccctctctcc caacgctttg agagaatagc tgtccagcca      60
ctcactggtg tccttggtgc tgagatcact ggagtggact tgagggaacc acttgatgac     120
agcacctgga atgagatatt ggatgccttc cacacttacc aagtcatcta ctttcctggc     180
caagcaatca ccaatgagca gcacattgca ttctcaagaa ggtttggacc agttgatcca     240
gtgcctcttc tcaagagcat tgaaggctat ccagaggttc agatgatccg cagagaagcc     300
```

-continued

```
aatgagtctg gaagggtgat tggtgatgac tggcacacag actccacttt ccttgatgca      360
cctccagctg ctgttgtgat gagggccata gatgttcctg agcatggcgg agacactggg      420
ttcctttcaa tgtacacagc ttgggagacc ttgtctccaa ccatgcaagc caccatcgaa      480
gggctcaacg ttgtgcactc tgccacacgt gtgttcggtt ccctctacca agcacagaac      540
cgtcgcttca gcaacacctc agtcaaggtg atggatgttg atgctggtga cagagagaca      600
gtccatccct tggttgtgac tcatcctggc tctggaagga aaggccttta tgtgaatcaa      660
gtctactgtc agagaattga gggcatgaca gatgcagaat caaagccatt gcttcagttc      720
ctctatgagc atgccaccag atttgacttc acttgccgtg tgaggtggaa gaaagaccaa      780
gtccttgtct gggacaactt gtgcaccatg caccgtgctg ttcctgacta tgctggcaag      840
ttcagatact tgactcgcac cacagttggt ggagttaggc ctgcccgctg agtagttagc      900
ttaatcacct agagctcggt aacctttaaa ctgagggcac tgaagtcgct tgatgtgctg      960
aattgtttgt gatgttggtg gcgtattttg tttaaataag taagcatggc tgtgatttta     1020
tcatatgatc gatctttggg gttttatttta acacattgta aaatgtgtat ctattaataa     1080
ctcaatgtat aagatgtgtt cattcttcgg ttgccataga tctgcttatt tgacctgtga     1140
tgttttgact ccaaaaacca aaatcacaac tcaataaact catggaatat gtccacctgt     1200
ttcttgaaga gttcatctac cattccagtt ggcatttatc agtgttgcag cggcgctgtg     1260
ctttgtaaca taacaattgt tacggcatat atccaa                               1296
```

```
<210> SEQ ID NO 6
<211> LENGTH: 1331
<212> TYPE: DNA
<213> ORGANISM: Artificial
<220> FEATURE:
<223> OTHER INFORMATION: pDAB112375 expression cassette
<220> FEATURE:
<221> NAME/KEY: misc_feature
<222> LOCATION: (918)..(952)
<223> OTHER INFORMATION: native tsh4 miR529-156 target site
<220> FEATURE:
<221> NAME/KEY: misc_feature
<222> LOCATION: (967)..(1331)
<223> OTHER INFORMATION: ZmPer5 3'UTR

<400> SEQUENCE: 6
```

```
atggctcatg ctgccctcag ccctctctcc caacgctttg agagaatagc tgtccagcca       60
ctcactggtg tccttggtgc tgagatcact ggagtggact tgagggaacc acttgatgac      120
agcacctgga atgagatatt ggatgccttc cacacttacc aagtcatcta ctttcctggc      180
caagcaatca ccaatgagca gcacattgca ttctcaagaa ggtttggacc agttgatcca      240
gtgcctcttc tcaagagcat tgaaggctat ccagaggttc agatgatccg cagagaagcc      300
aatgagtctg gaagggtgat tggtgatgac tggcacacag actccacttt ccttgatgca      360
cctccagctg ctgttgtgat gagggccata gatgttcctg agcatggcgg agacactggg      420
ttcctttcaa tgtacacagc ttgggagacc ttgtctccaa ccatgcaagc caccatcgaa      480
gggctcaacg ttgtgcactc tgccacacgt gtgttcggtt ccctctacca agcacagaac      540
cgtcgcttca gcaacacctc agtcaaggtg atggatgttg atgctggtga cagagagaca      600
gtccatccct tggttgtgac tcatcctggc tctggaagga aaggccttta tgtgaatcaa      660
gtctactgtc agagaattga gggcatgaca gatgcagaat caaagccatt gcttcagttc      720
ctctatgagc atgccaccag atttgacttc acttgccgtg tgaggtggaa gaaagaccaa      780
gtccttgtct gggacaactt gtgcaccatg caccgtgctg ttcctgacta tgctggcaag      840
```

```
ttcagatact tgactcgcac cacagttggt ggagttaggc ctgcccgctg agtagttagc      900
ttaatcacct agagctcgac tccagctgtg ctctctctct tctgtcaact caggtaacct      960
ttaaactgag ggcactgaag tcgcttgatg tgctgaattg tttgtgatgt tggtggcgta     1020
ttttgtttaa ataagtaagc atggctgtga ttttatcata tgatcgatct ttggggtttt     1080
atttaacaca ttgtaaaatg tgtatctatt aataactcaa tgtataagat gtgttcattc     1140
ttcggttgcc atagatctgc ttatttgacc tgtgatgttt tgactccaaa aaccaaaatc     1200
acaactcaat aaactcatgg aatatgtcca cctgtttctt gaagagttca tctaccattc     1260
cagttggcat ttatcagtgt tgcagcggcg ctgtgctttg taacataaca attgttacgg     1320
catatatcca a                                                          1331
```

<210> SEQ ID NO 7
<211> LENGTH: 37
<212> TYPE: DNA
<213> ORGANISM: Artificial
<220> FEATURE:
<223> OTHER INFORMATION: modified tsh4 target site

<400> SEQUENCE: 7

```
gactcaggct gtactctctt acttcacaaa gtactca                                37
```

<210> SEQ ID NO 8
<211> LENGTH: 37
<212> TYPE: DNA
<213> ORGANISM: Artificial
<220> FEATURE:
<223> OTHER INFORMATION: modified tsh4 target site

<400> SEQUENCE: 8

```
gactcaggct gtactctctc tcttcacaaa gtactca                                37
```

<210> SEQ ID NO 9
<211> LENGTH: 1333
<212> TYPE: DNA
<213> ORGANISM: Artificial
<220> FEATURE:
<223> OTHER INFORMATION: pDAB112377 expression cassette
<220> FEATURE:
<221> NAME/KEY: misc_feature
<222> LOCATION: (918)..(954)
<223> OTHER INFORMATION: modified tsh4 target site
<220> FEATURE:
<221> NAME/KEY: misc_feature
<222> LOCATION: (969)..(1333)
<223> OTHER INFORMATION: ZmPer5 3'UTR

<400> SEQUENCE: 9

```
atggctcatg ctgccctcag ccctctctcc caacgctttg agagaatagc tgtccagcca       60
ctcactggtg tccttggtgc tgagatcact ggagtggact tgagggaacc acttgatgac      120
agcacctgga atgagatatt ggatgccttc cacacttacc aagtcatcta ctttcctggc      180
caagcaatca ccaatgagca gcacattgca ttctcaagaa ggtttggacc agttgatcca      240
gtgcctcttc tcaagagcat tgaaggctat ccagaggttc agatgatccg cagagaagcc      300
aatgagtctg gaagggtgat tggtgatgac tggcacacag actccacttt ccttgatgca      360
cctccagctg ctgttgtgat gagggccata gatgttcctg agcatggcgg agacactggg      420
ttcctttcaa tgtacacagc ttgggagacc ttgtctccaa ccatgcaagc caccatcgaa      480
gggctcaacg ttgtgcactc tgccacacgt gtgttcggtt ccctctacca agcacagaac      540
```

-continued

```
cgtcgcttca gcaacacctc agtcaaggtg atggatgttg atgctggtga cagagagaca      600
gtccatccct tggttgtgac tcatcctggc tctggaagga aaggccttta tgtgaatcaa      660
gtctactgtc agagaattga gggcatgaca gatgcagaat caaagccatt gcttcagttc      720
ctctatgagc atgccaccag atttgacttc acttgccgtg tgaggtggaa gaaagaccaa      780
gtccttgtct gggacaactt gtgcaccatg caccgtgctg ttcctgacta tgctggcaag      840
ttcagatact tgactcgcac cacagttggt ggagttaggc ctgcccgctg agtagttagc      900
ttaatcacct agagctcgac tcaggctgta ctctcttact tcacaaagta ctcaggtaac      960
ctttaaactg agggcactga agtcgcttga tgtgctgaat tgtttgtgat gttggtggcg     1020
tattttgttt aaataagtaa gcatggctgt gattttatca tatgatcgat ctttggggtt     1080
ttatttaaca cattgtaaaa tgtgtatcta ttaataactc aatgtataag atgtgttcat     1140
tcttcggttg ccatagatct gcttatttga cctgtgatgt tttgactcca aaaaccaaaa     1200
tcacaactca ataaactcat ggaatatgtc cacctgtttc ttgaagagtt catctaccat     1260
tccagttggc atttatcagt gttgcagcgg cgctgtgctt tgtaacataa caattgttac     1320
ggcatatatc caa                                                        1333
```

```
<210> SEQ ID NO 10
<211> LENGTH: 1333
<212> TYPE: DNA
<213> ORGANISM: Artificial
<220> FEATURE:
<223> OTHER INFORMATION: expression cassette
<220> FEATURE:
<221> NAME/KEY: misc_feature
<222> LOCATION: (918)..(954)
<220> FEATURE:
<221> NAME/KEY: misc_feature
<222> LOCATION: (969)..(1333)
<223> OTHER INFORMATION: ZmPer5 3'UTR

<400> SEQUENCE: 10
```

```
atggctcatg ctgccctcag ccctctctcc caacgctttg agagaatagc tgtccagcca      60
ctcactggtg tccttggtgc tgagatcact ggagtggact tgagggaacc acttgatgac     120
agcacctgga atgagatatt ggatgccttc cacacttacc aagtcatcta ctttcctggc     180
caagcaatca ccaatgagca gcacattgca ttctcaagaa ggtttggacc agttgatcca     240
gtgcctcttc tcaagagcat tgaaggctat ccagaggttc agatgatccg cagagaagcc     300
aatgagtctg gaagggtgat tggtgatgac tggcacacag actccacttt ccttgatgca     360
cctccagctg ctgttgtgat gagggccata gatgttcctg agcatggcgg agacactggg     420
ttcctttcaa tgtacacagc ttgggagacc ttgtctccaa ccatgcaagc caccatcgaa     480
gggctcaacg ttgtgcactc tgccacacgt gtgttcggtt ccctctacca agcacagaac     540
cgtcgcttca gcaacacctc agtcaaggtg atggatgttg atgctggtga cagagagaca     600
gtccatccct tggttgtgac tcatcctggc tctggaagga aaggccttta tgtgaatcaa     660
gtctactgtc agagaattga gggcatgaca gatgcagaat caaagccatt gcttcagttc     720
ctctatgagc atgccaccag atttgacttc acttgccgtg tgaggtggaa gaaagaccaa     780
gtccttgtct gggacaactt gtgcaccatg caccgtgctg ttcctgacta tgctggcaag     840
ttcagatact tgactcgcac cacagttggt ggagttaggc ctgcccgctg agtagttagc     900
ttaatcacct agagctcgac tcaggctgta ctctctctct tcacaaagta ctcaggtaac     960
ctttaaactg agggcactga agtcgcttga tgtgctgaat tgtttgtgat gttggtggcg    1020
```

-continued

```
tattttgttt aaataagtaa gcatggctgt gattttatca tatgatcgat ctttggggtt      1080
ttatttaaca cattgtaaaa tgtgtatcta ttaataactc aatgtataag atgtgttcat      1140
tcttcggttg ccatagatct gcttatttga cctgtgatgt tttgactcca aaaaccaaaa      1200
tcacaactca ataaactcat ggaatatgtc cacctgtttc ttgaagagtt catctaccat      1260
tccagttggc atttatcagt gttgcagcgg cgctgtgctt tgtaacataa caattgttac      1320
ggcatatatc caa                                                          1333

<210> SEQ ID NO 11
<211> LENGTH: 272
<212> TYPE: DNA
<213> ORGANISM: Artificial
<220> FEATURE:
<223> OTHER INFORMATION: artificial miRNA CMSRF9973.1

<400> SEQUENCE: 11
ggatcccagc agcagccaca gcaaaatttg gtttgggata ggtaggtgtt atgttaggtc        60
tggttttttg gctgtagcag cagcagagaa gagagagagt acagcctcag gagattcagt       120
ttgaagctgg acttcacttt tgcctctcta ggctctacac tctctcttct ttcctgctgc       180
taggctgttc tgtggaagtt tgcagagttt atattatggg tttaatcgtc catggcatca       240
gcatcagcag catttaaatg agctcggtaa cc                                     272

<210> SEQ ID NO 12
<211> LENGTH: 1429
<212> TYPE: DNA
<213> ORGANISM: Artificial
<220> FEATURE:
<223> OTHER INFORMATION: SCBV promoter

<400> SEQUENCE: 12
tcggaagttg aagacaaaga aggtcttaaa tcctggctag caacactgaa ctatgccaga        60
aaccacatca aagcatatcg gcaagcttct tggcccatta tatccaaaga cctcagagaa       120
aggtgagcga aggctcaatt cagaagattg gaagctgatc aataggatca agacaatggt       180
gagaacgctt ccaaatctca ctattccacc agaagatgca tacattatca ttgaaacaga       240
tgcatgtgca actggatggg gagcagtatg caagtggaag aaaaacaagg cagacccaag       300
aaatacagag caaatctgta ggtatgccag tggaaaattt gataagccaa aaggaacctg       360
tgatgcagaa atctatgggg ttatgaatgg cttagaaaag atgagattgt tctacttgga       420
caaaagagag atcacagtca gaactgacag tagtgcaatc gaaaggttct acaacaagag       480
tgctgaacac aagccttctg agatcagatg gatcaggttc atggactaca tcactggtgc       540
aggaccagag atagtcattg aacacataaa agggaagagc aatggtttag ctgacatctt       600
gtccaggctc aaagccaaat agctcagaa tgaaccaacg gaagagatga tcctgcttac       660
acaagccata agggaagtaa ttccttatcc agatcatcca tacactgagc aactcagaga       720
atggggaaac aaaattctgg atccattccc cacattcaag aaggacatgt tcgaaagaac       780
agagcaagct tttatgctaa cagaggaacc agttctactc tgtgcatgca ggaagcctgc       840
aattcagtta gtgtccagaa catctgccaa cccaggaagg aaattcttca gtgcgcaat       900 gaacaaatgc cattgctggt actgggcaga tctcattgaa gaacacattc aagacagaat       960
tgatgaattt ctcaagaatc ttgaagttct gaagaccggt ggcgtgcaaa caatggagga      1020
ggaacttatg aaggaagtca ccaagctgaa gatagaagag caggagttcg aggaatacca      1080
ggccacacca agggctatgt cgccagtagc cgcagaagat gtgctagatc tccaagacgt      1140
```

-continued

```
aagcaatgac gattgaggag gcattgacgt cagggatgac cgcagcggag agtactgggc     1200
ccattcagtg gatgctccac tgagttgtat tattgtgtgc ttttcggaca agtgtgctgt     1260
ccactttctt ttggcacctg tgccacttta ttccttgtct gccacgatgc ctttgcttag     1320
cttgtaagca aggatcgcag tgcgtgtgtg acaccacccc ccttccgacg ctctgcctat     1380
ataaggcacc gtctgtaagc tcttacgatc atcggtagtt caccaaggc                1429
```

<210> SEQ ID NO 13
<211> LENGTH: 531
<212> TYPE: DNA
<213> ORGANISM: Artificial
<220> FEATURE:
<223> OTHER INFORMATION: synthetic 5' UTR

<400> SEQUENCE: 13

```
ctgaaggctc gacaaggcag tccacggagg agctgatatt tggtggacaa gctgtggata      60
ggagcaaccc tatccctaat ataccagcac caccaagtca gggcaatccc cagatcaccc     120
cagcagattc gaagaaggta cagtacacac acatgtatat atgtatgatg tatcccttcg     180
atcgaaggca tgccttggta taatcactga gtagtcattt tattactttg ttttgacaag     240
tcagtagttc atccatttgt cccatttttt cagcttggaa gtttggttgc actggccttg     300
gtctaataac tgagtagtca ttttattacg ttgtttcgac aagtcagtag ctcatccatc     360
tgtcccattt tttcagctag gaagtttggt tgcactggcc ttggactaat aactgattag     420
tcattttatt acattgtttc gacaagtcag tagctcatcc atctgtccca tttttcagct     480
aggaagttcg gatctggggc catttgttcc aggcacggga taagcattca g              531
```

<210> SEQ ID NO 14
<211> LENGTH: 4233
<212> TYPE: DNA
<213> ORGANISM: Artificial
<220> FEATURE:
<223> OTHER INFORMATION: maize Invertase (INV) gene

<400> SEQUENCE: 14

```
agcctggtgt ttccggagga gacagacatg atccctgccg ttgctgatcc gacgacgctg      60
gacggcgggg gcgcgcgcag gccgttgctc ccggagacgg accctcgggg gcgtgctgcc     120
gccggcgccg agcagaagcg gccgccggct acgccgaccg ttctcaccgc cgtcgtctcc     180
gccgtgctcc tgctcgtcct cgtggcggtc acagtcctcg cgtcgcagca cgtcgacggg     240
caggctgggg gcgttcccgc gggcgaagat gccgtcgtcg tcgaggtggc cgcctcccgt     300
ggcgtggctg agggcgtgtc ggagaagtcc acggccccgc tcctcggctc cggcgcgctc     360
caggacttct cctggaccaa cgcgatgctg cgtggcagc gcacggcgtt ccacttccag     420
ccccccaaga actggatgaa cggttagttg gacccgtcgc catcggtgac gacgcgcgga     480 tcgtttttt cttttttcct ctcgttctgg ctctaacttg gttccgcgtt tctgtcacgg     540
acgcctcgtg cacatggcga tacccgatcc gccggccgcg tatatctatc tacctcgacc     600
ggcttctcca gatccgaacg gtaagttgtt ggctccgata cgatcgatca catgtgagct     660
cggcatgctg ctttttctgcg cgtgcatgcg gctcctagca ttccacgtcc acgggtcgtg     720
acatcaatgc acgatataat cgtatcggta cagagatatt gtcccatcag ctgctagctt     780
tcgcgtattg atgtcgtgac attttgcacg caggtccgct gtatcacaag ggctggtacc     840
acctcttcta ccagtggaac ccggactccg cggtatgggg caacatcacc tggggccacg     900
```

-continued

```
ccgtctcgcg cgacctcctc cactggctgc acctaccgct ggccatggtg cccgatcacc      960
cgtacgacgc caacggcgtc tggtccgggt cggcgacgcg cctgcccgac ggccggatcg     1020
tcatgctcta cacgggctcc acggcggagt cgtcggcgca ggtgcagaac ctcgcggagc     1080
cggccgacgc gtccgacccg ctgctgcggg agtgggtcaa gtcggacgcc aacccggtgc     1140
tggtgccgcc gccgggcatc gggccgacgg acttccgcga cccgacgacg gcgtgtcgga     1200
cgccggccgg caacgacacg gcgtggcggg tcgccatcgg gtccaaggac cgggaccacg     1260
cggggctggc gctggtgtac cggacggagg acttcgtgcg gtacgacccg gcgccggcgc     1320
tgatgcacgc cgtgccgggc accggcatgt gggagtgcgt ggacttctac ccggtggccg     1380
cgggatcagg cgccgcggcg ggcagcgggg acgggctgga gacgtccgcg gcgccgggac     1440
ccggggtgaa gcacgtgctc aaggctagcc tcgacgacga caagcacgac tactacgcga     1500
tcggcaccta cgaccgggcg acggacacct ggacccccga cagcgcggag gacgacgtcg     1560
ggatcggcct ccggtacgac tatggcaagt actacgcgtc gaagaccttc tacgaccccg     1620
tccttcgccg gcgggtgctc tggggtgggg tcggcgagac cgacagcgag cgcgcggaca     1680
tcctcaaggg ctgggcatcc gtgcaggtac gtctcagggt ttgaggctag catggcttca     1740
atcttgctgg catcgaatca ttaatgggca gatattataa cttgataatc tgggttggtt     1800
gtgtgtggtg gggatggtga cacacgcgcg gtaataatgt agctaagctg gttaaggatg     1860
agtaatgggg ttgcgtataa acgacagctc tgctaccatt acttctgaca cccgattgaa     1920
ggagacaaca gtaggggtag ccggtagggt cgtcgactt gccttttctt ttttcctttg      1980
ttttgttgtg gatcgtccaa cacaaggaaa ataggatcat ccaacaaaca tggaagtaat     2040
cccgtaaaac atttctcaag gaaccatcta gctagacgag cgtggcatga tccatgcatg     2100
cacaaacact agataggtct ctgcagctgt gatgttcctt tacatatacc accgtccaaa     2160
ctgaatccgg tctgaaaatt gttcaagcag agaggccccg atcctcacac ctgtacacgt     2220
ccctgtacgc gccgtcgtgg tctcccgtga tcctgccccg tcccctccac gcggccacgc     2280
ctgctgcagc gctctgtaca agcgtgcacc acgtgagaat ttccgtctac tcgagcctag     2340
tagttagacg ggaaaacgag aggaagcgca cggtccaagc acaacacttt gcgcgggccc     2400
gtgacttgtc tccggttggc tgagggcgcg cgacagagat gtatggcgcc gcggcgtgtc     2460
ttgtgtcttg tcttgcctat acaccgtagt cagagactgt gtcaaagccg tccaacgaca     2520
atgagctagg aaacgggttg gagagctggg ttcttgcctt gcctcctgtg atgtctttgc     2580
cttgcatagg gggcgcagta tgtagctttg cgttttactt cacgccaaag gatactgctg     2640
atcgtgaatt attattatta tatatatatc gaatatcgat ttcgtcgctc tcgtggggtt     2700
ttattttcca gactcaaact tttcaaaagg cctgtgtttt agttcttttc ttccaattga     2760
gtaggcaagg cgtgtgagtg tgaccaacgc atgcatggat atcgtggtag actggtagag     2820
ctgtcgttac cagcgcgatg cttgtatatg tttgcagtat tttcaaatga atgtctcagc     2880
tagcgtacag ttgaccaagt cgacgtggag ggcgcacaac agacctctga cattattcac     2940 tttttttta ccatgccgtg cacgtgcagt caatccccag gacggtcctc ctggacacga     3000
agacgggcag caacctgctc cagtggccgg tggtggaggt ggagaacctc cggatgagcg     3060
gcaagagctt cgacggcgtc gcgctggacc gcggatccgt cgtgcccctc gacgtcggca     3120
aggcgacgca ggtgacgccg cacgcagcct gctgcagcga acgaactcgc gcgttgccgg     3180
cccgcggcca gctgacttag tttctctggc tgatcgaccg tgtgcctgcg tgcgtgcagt     3240
tggacatcga ggctgtgttc gaggtggacg cgtcggacgc ggcgggcgtc acggaggccg     3300
```

-continued

```
acgtgacgtt caactgcagc accagcgcag gcgcggcggg ccggggcctg ctcggcccgt    3360
tcggccttct cgtgctggcg gacgacgact tgtccgagca gaccgccgtg tacttctacc    3420
tgctcaaggg cacggacggc agcctccaaa ctttcttctg ccaagacgag ctcaggtatg    3480
tatgttatga cttatgacca tgcatgcatg cgcatttctt agctaggctg tgaagcttct    3540
tgttgagttg tttcacagat gcttaccgtc tgctttgttt cgtatttcga ctaggcatcc    3600
aaggcgaacg atctggttaa gagagtatac gggagcttgg tccctgtgct agatggggag    3660
aatctctcgg tcagaatact ggtaagtttt tacagcgcca gccatgcatg tgttggccag    3720
ccagctgctg gtactttgga cactcgttct tctcgcactg ctcattattg cttctgatct    3780
ggatgcacta caaattgaag gttgaccact ccatcgtgga gagctttgct caaggcggga    3840
ggacgtgcat cacgtcgcga gtgtacccca cacgagccat ctacgactcc gcccgcgtct    3900
tcctcttcaa caacgccaca catgctcacg tcaaagcaaa atccgtcaag atctggcagc    3960
tcaactccgc ctacatccgg ccatatccgg caacgacgac ttctctatga ctaaattaag    4020
tgacggacag ataggcgata ttgcatactt gcatcatgaa ctcatttgta caacagtgat    4080
tgtttaattt atttgctgcc ttccttatcc ttcttgtgaa actatatggt acacacatgt    4140
atcattaggt ctagtagtgt tgttgcaaag acacttagac accagaggtt ccaggagtat    4200
cagagataag gtataagagg gagcagggag cag                                 4233
```

<210> SEQ ID NO 15
<211> LENGTH: 1600
<212> TYPE: DNA
<213> ORGANISM: Artificial
<220> FEATURE:
<223> OTHER INFORMATION: Maize gene Elongation Factor 1? (EF1?)

<400> SEQUENCE: 15

```
cgcctcgccg tctgccttct gcgcctccat ttcggcctct gtcccttgca agttcaatct      60
cacctccaac catgggtaaa gagaagtccc acatcaacat tgtggttatt ggccatgtcg     120
actctggcaa gtcgaccacc acaggacacc ttatctacaa gcttggaggc attgacaagc     180
gtgtgatcga gaggttcgag aaggaggctg ctgaaatgaa caagcggtcc ttcaagtacg     240
cgtgggtgct cgacaagctc aaggctgagc gtgagagagg tatcaccatt gatatcgctc     300
tgtggaagtt tgagaccacc aagtactact gcacggtcat tgatgcccct ggacaccgtg     360
acttcatcaa gaacatgatc actggtacct cccaggctga ctgtgctgtc cttatcattg     420
actccaccac tggtggtttt gaggctggta tctccaagga tggccagacc cgtgaacatg     480
ctctccttgc gttcacactt ggagtgaagc agatgatttg ctgctgcaac aagatggatg     540
caaccactcc caaatactcc aaggcacgtt atgaagagat tgtgaaggaa gtctcatcct     600
acctcaagaa agttgggtac aaccctgata gattgccctt tgttcccatt tctggttttg     660
agggcgacaa catgattgag aggtccacca accttgactg tacaaaggc ccaaccctgc      720 ttgaggctct tgaccagatc accgagccca agaggccttc agacaagccc ctgcgtctag     780
ccctccagga tgtgtacaag attggtggta ttggaactgt accggttggt cgtgtggaga     840
ctggtgtcat caagcctggt atggtagtca cctttggtcc aactggcctg actaccgagg     900
tgaagtctgt tgagatgcac cacgaggcac ttcaggaggc tcttccgggt gacaatgttg     960
gcttcaacgt gaagaatgtt gctgtcaagg atctcaagcg tgggtttgtg gcctccaact    1020
ccaaggatga ccctgccaag gaggctgcca gcttcacctc ccaggtcatc atcatgaacc    1080
```

-continued

```
accctgggca gattggcaac ggctatgccc ctgtgctgga ctgccacacc tcccacatcg      1140
ctgtcaagtt tgctgagctc attaccaaga tcgacaggcg ctctggcaag gagcttgaga      1200
aggagccaaa gttcctgaag aacggtgatg ctggtatggt gaagatgata cccaccaagc      1260
ctatggtggt ggagacattc tccgcgtatc ctcccctggg taggtttgcc gtccgcgaca      1320
tgaggcagac ggttgctgtt ggagtcatca agagtgtgga gaagaaggac ccaaccggcg      1380
ccaaggtgac caaggcggcc gccaagaaga aatgatgcga tccctgcgcc tgctttagca      1440
ataccctagt ttccatcatt acaagtttgt ttgtggtcgt tgctgttatt gtgtgaactg      1500
ttgagctctg ttagcctgtg cacttttatc tatttatttg gtaccttctt gctatttcac      1560
cttctgcaat acaagaatgc tgtaagagct atatgttaac                            1600
```

```
<210> SEQ ID NO 16
<211> LENGTH: 20
<212> TYPE: DNA
<213> ORGANISM: Artificial
<220> FEATURE:
<223> OTHER INFORMATION: Oligonucleotide AAD1F

<400> SEQUENCE: 16
tgttcggttc cctctaccaa                                                    20

<210> SEQ ID NO 17
<211> LENGTH: 22
<212> TYPE: DNA
<213> ORGANISM: Artificial
<220> FEATURE:
<223> OTHER INFORMATION: Oligonucleotide AAD1R

<400> SEQUENCE: 17
caacatccat caccttgact ga                                                 22

<210> SEQ ID NO 18
<211> LENGTH: 24
<212> TYPE: DNA
<213> ORGANISM: Artificial
<220> FEATURE:
<223> OTHER INFORMATION: Oligonucleotide AAD1P

<400> SEQUENCE: 18
cacagaaccg tcgcttcagc aaca                                               24

<210> SEQ ID NO 19
<211> LENGTH: 29
<212> TYPE: DNA
<213> ORGANISM: Artificial
<220> FEATURE:
<223> OTHER INFORMATION: Oligonucleotide PAT_F

<400> SEQUENCE: 19
acaagagtgg attgatgatc tagagaggt                                          29

<210> SEQ ID NO 20
<211> LENGTH: 29
<212> TYPE: DNA
<213> ORGANISM: Artificial
<220> FEATURE:
<223> OTHER INFORMATION: Oligonucleotide PAT_R

<400> SEQUENCE: 20
ctttgatgcc tatgtgacac gtaaacagt                                          29
```

<210> SEQ ID NO 21
<211> LENGTH: 29
<212> TYPE: DNA
<213> ORGANISM: Artificial
<220> FEATURE:
<223> OTHER INFORMATION: Oligonucleotide PAT_FamP

<400> SEQUENCE: 21
ggtgttgtgg ctggtattgc ttacgctgg                                          29

<210> SEQ ID NO 22
<211> LENGTH: 19
<212> TYPE: DNA
<213> ORGANISM: Artificial
<220> FEATURE:
<223> OTHER INFORMATION: Oligonucleotide SPC1A

<400> SEQUENCE: 22
cttagctgga taacgccac                                                     19

<210> SEQ ID NO 23
<211> LENGTH: 19
<212> TYPE: DNA
<213> ORGANISM: Artificial
<220> FEATURE:
<223> OTHER INFORMATION: Oligonucleotide SPC1S

<400> SEQUENCE: 23
gaccgtaagg cttgatgaa                                                     19

<210> SEQ ID NO 24
<211> LENGTH: 21
<212> TYPE: DNA
<213> ORGANISM: Artificial
<220> FEATURE:
<223> OTHER INFORMATION: Oligonucleotide TQSPC

<400> SEQUENCE: 24
cgagattctc cgcgctgtag a                                                  21

<210> SEQ ID NO 25
<211> LENGTH: 18
<212> TYPE: DNA
<213> ORGANISM: Artificial
<220> FEATURE:
<223> OTHER INFORMATION: Oligonucleotide InvertaseF

<400> SEQUENCE: 25
tggcggacga cgacttgt                                                      18

<210> SEQ ID NO 26
<211> LENGTH: 19
<212> TYPE: DNA
<213> ORGANISM: Artificial
<220> FEATURE:
<223> OTHER INFORMATION: Oligonucleotide InvertaseR

<400> SEQUENCE: 26
aaagtttgga ggctgccgt                                                     19

<210> SEQ ID NO 27
<211> LENGTH: 21
<212> TYPE: DNA
<213> ORGANISM: Artificial
<220> FEATURE:
<223> OTHER INFORMATION: Oligonucleotide InvertaseP -continued

<400> SEQUENCE: 27
cgagcagacc gccgtgtact t                                                    21

<210> SEQ ID NO 28
<211> LENGTH: 23
<212> TYPE: DNA
<213> ORGANISM: Artificial
<220> FEATURE:
<223> OTHER INFORMATION: Oligonucleotide EF1a_F

<400> SEQUENCE: 28
ataacgtgcc ttggagtatt tgg                                                  23

<210> SEQ ID NO 29
<211> LENGTH: 22
<212> TYPE: DNA
<213> ORGANISM: Artificial
<220> FEATURE:
<223> OTHER INFORMATION: Oligonucleotide EF1a_R

<400> SEQUENCE: 29
tggagtgaag cagatgattt gc                                                   22

<210> SEQ ID NO 30
<211> LENGTH: 18
<212> TYPE: DNA
<213> ORGANISM: Artificial
<220> FEATURE:
<223> OTHER INFORMATION: Oligonucleotide EF1a-MGB

<400> SEQUENCE: 30
ttgcatccat cttgttgc                                                        18

<210> SEQ ID NO 31
<211> LENGTH: 22
<212> TYPE: DNA
<213> ORGANISM: Artificial
<220> FEATURE:
<223> OTHER INFORMATION: random primer T20VN
<220> FEATURE:
<221> NAME/KEY: misc_feature
<222> LOCATION: (22)..(22)
<223> OTHER INFORMATION: n is a, c, g, or t

<400> SEQUENCE: 31
tttttttttt tttttttttt vn                                                   22

<210> SEQ ID NO 32
<211> LENGTH: 50
<212> TYPE: DNA
<213> ORGANISM: Artificial
<220> FEATURE:
<223> OTHER INFORMATION: miR156_RT

<400> SEQUENCE: 32
gttggctctg gtgcagggtc cgaggtattc gcaccagagc caacgtgctc                     50

<210> SEQ ID NO 33
<211> LENGTH: 50
<212> TYPE: DNA
<213> ORGANISM: Artificial
<220> FEATURE:
<223> OTHER INFORMATION: miR529_RT

<400> SEQUENCE: 33
gttggctctg gtgcagggtc cgaggtattc gcaccagagc caacaggctg                     50

```
<210> SEQ ID NO 34
<211> LENGTH: 22
<212> TYPE: DNA
<213> ORGANISM: Artificial
<220> FEATURE:
<223> OTHER INFORMATION: miR156_F Forward Primer

<400> SEQUENCE: 34
ggtgacagaa gagagtgagc ac                                              22

<210> SEQ ID NO 35
<211> LENGTH: 23
<212> TYPE: DNA
<213> ORGANISM: Artificial
<220> FEATURE:
<223> OTHER INFORMATION: miR529_F Forward Primer

<400> SEQUENCE: 35
ggcggagaag agagagagta cag                                             23

<210> SEQ ID NO 36
<211> LENGTH: 16
<212> TYPE: DNA
<213> ORGANISM: Artificial
<220> FEATURE:
<223> OTHER INFORMATION: Universal Reverse Primer

<400> SEQUENCE: 36
gtgcagggtc cgaggt                                                     16

<210> SEQ ID NO 37
<211> LENGTH: 171
<212> TYPE: PRT
<213> ORGANISM: Sphingobium herbicidovorans
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(27)
<223> OTHER INFORMATION: Xaa can be any naturally occurring amino acid
<220> FEATURE:
<221> NAME/KEY: misc_feature
<222> LOCATION: (29)..(159)
<223> OTHER INFORMATION: Xaa can be any naturally occurring amino acid
<220> FEATURE:
<221> NAME/KEY: misc_feature
<222> LOCATION: (161)..(170)
<223> OTHER INFORMATION: Xaa can be any naturally occurring amino acid

<400> SEQUENCE: 37

His Xaa Asp Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Thr Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95
```

```
Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa His
145                 150                 155                 160

Xaa Xaa Xaa Xaa Xaa Xaa Xaa Xaa Xaa Arg
            165                 170
```

```
<210> SEQ ID NO 38
<211> LENGTH: 175
<212> TYPE: PRT
<213> ORGANISM: Sphingobium herbicidovorans
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(27)
<223> OTHER INFORMATION: Xaa can be any naturally occurring amino acid
<220> FEATURE:
<221> NAME/KEY: misc_feature
<222> LOCATION: (29)..(159)
<223> OTHER INFORMATION: Xaa can be any naturally occurring amino acid
<220> FEATURE:
<221> NAME/KEY: misc_feature
<222> LOCATION: (161)..(170)
<223> OTHER INFORMATION: Xaa can be any naturally occurring amino acid
<220> FEATURE:
<221> NAME/KEY: misc_feature
<222> LOCATION: (172)..(174)
<223> OTHER INFORMATION: Xaa can be any naturally occurring amino acid

<400> SEQUENCE: 38

His Xaa Asp Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Thr Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa His
145                 150                 155                 160

Xaa Xaa Xaa Xaa Xaa Xaa Xaa Xaa Xaa Xaa Arg Xaa Xaa Xaa Arg
            165                 170                 175
```

TISSUE-SPECIFIC EXPRESSION AND HYBRID PLANT PRODUCTION

CROSS-REFERENCE TO RELATED APPLICATION

This application is a continuation application of U.S. patent application Ser. No. 16/046,780, filed Jul. 26, 2018, which is a divisional application of U.S. patent application Ser. No. 14/577,887, filed Dec. 19, 2014, and issued as U.S. Pat. No. 10,683,513B2 which claims the benefit of the filing date of U.S. Provisional Patent Application Ser. No. 61/922, 603, filed Dec. 31, 2013, the disclosures of which are hereby incorporated herein in their entirety by this reference.

REFERENCE TO SEQUENCE LISTING SUBMITTED ELECTRONICALLY

The official copy of the sequence listing is submitted electronically via EFS-Web as an ASCII formatted sequence listing with a file named "71601_US_CNT.txt", created on Nov. 8, 2023 and having a size of 28.0 kilobytes and is filed concurrently with the specification. The sequence listing contained in this ASCII formatted document is part of the specification and is herein incorporated by reference in its entirety.

TECHNICAL FIELD

The present disclosure relates to constructs and methods for the control of gene expression in plants. Specific embodiments herein relate to constructs and methods for utilizing the native RNA inhibition (RNAi) machinery of a plant cell to effect tissue-specific expression of a gene of interest, for example, in male plant tissues.

BACKGROUND

The development of hybrid crop varieties has enabled an increase in crop productivity, mainly due to hybrid vigor and increased uniformity. Most crops show hybrid vigor, but commercial production of hybrids is only feasible if a reliable and cost-effective pollination control system is available; hybrid seed production requires a system that prevents unwanted self-pollination.

Methods that can be used to prevent self-pollination include mechanical removal of anthers or male flowers, application of male-specific gametocides, and use of genetic cytoplasmic or nuclear-encoded male sterility. Mechanical removal is an expensive practice, which also undesirably reduces crop yield due to plant damage. With respect to the use of cytoplasmic male-sterile (CMS) lines, these lines have a mutation in their mitochondrial genome, and thus the male sterility is inherited as a dominant, maternally-transmitted trait. Cytoplasmic male sterility requires CMS mutants and nuclear restorer available in a given crop. Perez-Prat and van Lookeren Campagne (2002) *Trends Plant Sci.* 7:199-203.

In view of the foregoing considerations, the production of commercial hybrid corn seed typically utilizes the planting of male and female inbred lines in separate rows or blocks in an isolated field to reduce the possibility of contamination. The female inbred is then detasseled before pollen shed, which ensures cross-pollination by the male inbred. Hybrid seed is harvested and processed from the ears of the cross-pollinated female inbred. Manual or mechanical detasseling contributes to the high cost of hybrid corn seed.

Furthermore, hybrid seeds generally have lower yields, which further results in lower revenues and profitability.

RNA interference (RNAi) is a process utilizing endogenous cellular pathways, whereby an interfering RNA (iRNA) molecule (e.g., a dsRNA molecule) that is specific for a target gene sequence results in the degradation of the mRNA encoded thereby. In recent years, RNAi has been used to perform gene "knockdown" in a number of species and experimental systems; for example, *C. elegans*, plants, insect embryos, and cells in tissue culture. See, e.g., Fire et al. (1998) *Nature* 391:806-11; Martinez et al. (2002) *Cell* 110:563-74; McManus and Sharp (2002) *Nature Rev. Genetics* 3:737-47.

RNAi accomplishes degradation of mRNA through an endogenous pathway including the DICER protein complex. DICER cleaves long dsRNA molecules into short double-stranded fragments of approximately 20 nucleotides. The inhibitory double-stranded RNA is unwound into two single-stranded RNAs: the passenger strand and the guide strand. The passenger strand is degraded, and the guide strand is incorporated into the RNA-induced silencing complex (RISC). Post-transcriptional gene silencing (translational repression) occurs when the guide strand binds specifically to a complementary sequence of an mRNA molecule and induces cleavage by Argonaute, the catalytic component of the RISC complex.

Plant micro-RNAs (miRNAs) are typically produced from fold-back structures having a partial double-stranded structure (e.g., "hairpins"), and usually are nearly perfectly complementarity with target sites, which are found most commonly in protein-coding regions of the genome. As a result, plant miRNAs function generally to guide mRNA cleavage. Watson et al. (2005) *FEBS Lett.* 579:5982-7. In contrast, animal miRNAs contain relatively low levels of complementarity to their target sites, and thus generally do not guide cleavage, but rather function to repress expression at the translational or co-translational level. Watson et al. (2005), supra; Tomari and Zamore (2005) *Genes Dev.* 19 (5): 517-29. Although miRNA sequences are not conserved between plants and animals, the RNAi pathways that utilize these genes are highly similar. Millar and Waterhouse (2005) *Funct. Integr. Genomics* 5:129-35. For example, while the biogenesis of miRNAs in plants is accomplished by a different set of related enzymes than accomplish the biogenesis of animal miRNAs, the miRNA molecules themselves have a characteristic structure that is capable of effecting mRNA cleavage or translational repression, depending on their degree of sequence complementarity to the target gene. Id.

In addition to miRNAs, plants also produce endogenous 21-25 nucleotide small inhibitory-RNAs (siRNAs). Most of these differ from miRNAs, in that they arise from double-stranded RNA (rather than imperfect fold-back structures), which in some cases are generated by the activity of RNA-Dependent RNA Polymerases (RDRs).

Most plants contain four DICER-LIKE (DCL) proteins, one of which (DCL1) is necessary for maturation of most miRNA precursors. Kurihara and Watanabe (2004) *Proc. Natl. Acad. Sci. USA* 101:12753-8. Animal miRNA precursor processing requires the sequential nucleolytic activity of DROSHA and DICER. Lee et al. (2003) *Nature* 425:415-9. In animals, Exportin-5 (ExpS) regulates the transport of pre-miRNAs from the nucleus to the cytoplasm. Bohnsack et al. (2004) *RNA* 10:185-91.

Only RNA transcripts complementary to the siRNA and/or miRNA are cleaved and degraded by RNAi, and thus the knock-down of mRNA expression is sequence-specific. The gene silencing effect of RNAi persists for days and, under experimental conditions, can lead to a decline in abundance of the targeted transcript of 90% or more, with consequent reduction in levels of the corresponding protein.

BRIEF SUMMARY

Described herein are the compositions and methods of a novel plant small RNA (sRNA)-mediated approach for transgenic plant (e.g., hybrids) production. The approach utilizes sRNAs (e.g., endogenous siRNAs and miRNAs) that are expressed in specific tissues for targeted repression or knockdown of (trans) gene expression. In some embodiments, a target site of an sRNA is fused within a transgene sequence that confers herbicide tolerance. Tissue-specific expression of sRNA (e.g., endogenous sRNAs) in the tissue results in down-regulation of the transgene, which confers sensitivity to the herbicide upon the specific tissue, while other plant tissues remain tolerant.

In some embodiments, sRNAs are specifically expressed in male tissue of a plant, so as to repress/knockdown the expression of a transgene and thereby eliminate the need for manual detasseling. Particular embodiments include the sRNA-mediated tissue-specific expression of any transgene in plants that allows for timed induction of male sterility. In examples, the transgene is an herbicide tolerance gene, and application of the herbicide to the plant before or during tassel stage prevents tassel development and self-pollination. In some embodiments, sRNAs are specifically or preferentially expressed in, for example, the root tissue of a plant, so as to specifically or preferentially reduce expression of a transgene in the tissue.

Described herein are nucleic acid expression constructs, which constructs comprise a gene of interest having an internal target site for at least one sRNA molecule. In embodiments, RNA may be transcribed from the gene of interest in vivo when the construct is introduced into a plant cell, which RNA is then degraded by an RNAi mechanism under the control of the sRNA molecule(s). In particular embodiments, the gene of interest is an agronomic trait gene, an herbicide resistance gene or a selectable marker gene. In particular embodiments, the internal sRNA targeting site is, for example, 20-25 nucleotides in length.

Also described herein are transgenic plant cells, plant tissues, and plants comprising at least one of the foregoing nucleic acid expression constructs. In particular embodiments, the sRNA molecule is differentially expressed in different plant cells and tissues. For example, the gene (e.g., transgene) encoding the sRNA molecule may be operably linked to a non-constitutive promoter (e.g., a tissue-specific promoter). In particular embodiments, the sRNA is an endogenous sRNA of the plant cell. In certain examples, the sRNA is an endogenous sRNA that is expressed predominantly in male plant tissues, which sRNA directs degradation specifically in male tissues of RNA transcribed from the gene of interest, wherein the expression of RNA transcribed from the gene of interest in other tissues is essentially unaffected.

Further described herein are pollination control systems comprising the foregoing constructs and/or plant cells, plant tissues, and plants comprising such constructs.

The foregoing and other features will become more apparent from the following detailed description of several embodiments, which proceeds with reference to the accompanying figures.

4

SEQUENCE LISTING

Figure 1:
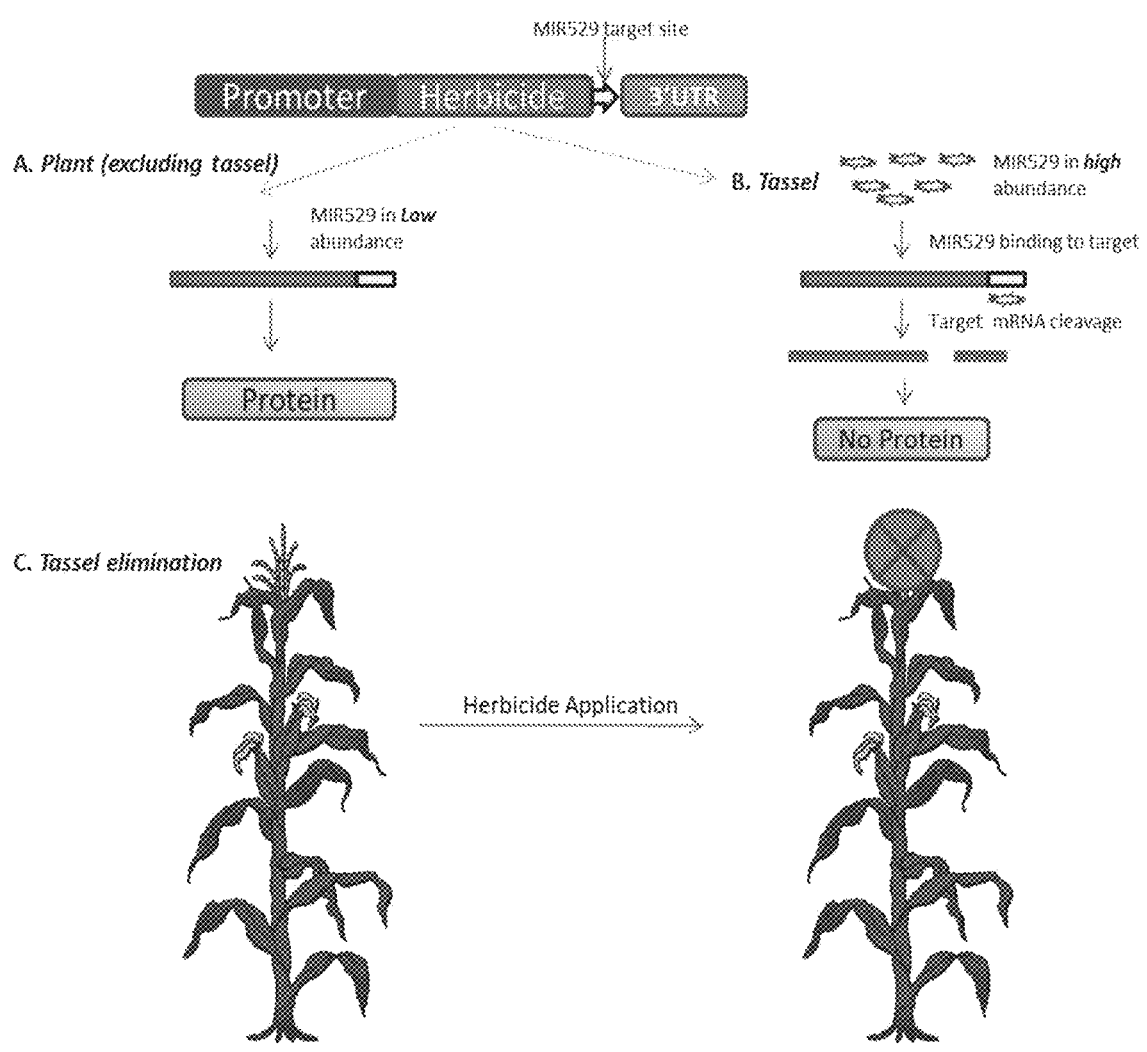
FIG. 1 includes a diagram of particular embodiments, wherein male tissue-specific herbicide susceptibility is conferred upon a transgenic corn plant as part of a pollination control system.

The nucleic acid sequences listed in the accompanying sequence listing are shown using standard letter abbreviations for nucleotide bases, as defined in 37 C.F.R. § 1.822. Only one strand of each nucleic acid sequence is shown, but the complementary strand is understood to be included by any reference to the displayed strand. In the accompanying sequence listing:

SEQ ID NO: 1 shows, in the 5' to 3' direction, an exemplary miR156 RNA:

UGACAGAAGAGAGUGAGCAC

SEQ ID NO:2 shows, in the 5' to 3' direction, an exemplary miR529 RNA:

AGAAGAGAGAGAGUACAGCCU

SEQ ID NO:3 shows an exemplary miR319 RNA:

UUGGACUGAAGGGUGCUCCC

SEQ ID NO:4 shows a tsh4 miR529-156 DNA target site:

GACTCCAGCTGTGCTCTCTCTCTTCTGTCAACTCA

SEQ ID NO:5 shows an exemplary expression cassette comprising an AAD-1 v3 coding region (underlined), followed by a fragment comprising a 3' UTR from a maize peroxidase 5 gene, ZmPer5 3'UTR (italics):

ATGGCTCATGCTGCCCTCAGCCCTCTCTCCCAACGCTTTGAGAGAATAGCT

GTCCAGCCACTCACTGGTGTCCTTGGTGCTGAGATCACTGGAGTGGACTTG

AGGGAACCACTTGATGACAGCACCTGGAATGAGATATTGGATGCCTTCCAC

ACTTACCAAGTCATCTACTTTCCTGGCCAAGCAATCACCAATGAGCAGCAC

ATTGCATTCTCAAGAAGGTTTGGACCAGTTGATCCAGTGCCTCTTCTCAAG

AGCATTGAAGGCTATCCAGAGGTTCAGATGATCCGCAGAGAAGCCAATGAG

TCTGGAAGGGTGATTGGTGATGACTGGCACACAGACTCCACTTTCCTTGAT

GCACCTCCAGCTGCTGTTGTGATGAGGGCCATAGATGTTCCTGAGCATGGC

GGAGACACTGGGTTCCTTTCAATGTACACAGCTTGGGAGACCTTGTCTCCA

ACCATGCAAGCCACCATCGAAGGGCTCAACGTTGTGCACTCTGCCACACGT

-continued

```
GTGTTCGGTTCCCTCTACCAAGCACAGAACCGTCGCTTCAGCAACACCTCA

GTCAAGGTGATGGATGTTGATGCTGGTGACAGAGAGACAGTCCATCCCTTG

GTTGTGACTCATCCTGGCTCTGGAAGGAAAGGCCTTTATGTGAATCAAGTC

TACTGTCAGAGAATTGAGGGCATGACAGATGCAGAATCAAAGCCATTGCTT

CAGTTCCTCTATGAGCATGCCACCAGATTTGACTTCACTTGCCGTGTGAGG

TGGAAGAAAGACCAAGTCCTTGTCTGGGACAACTTGTGCACCATGCACCGT

GCTGTTCCTGACTATGCTGGCAAGTTCAGATACTTGACTCGCACCACAGTT

GGTGGAGTTAGGCCTGCCCGCTGAGTAGTTAGCTTAATCACCTAGAGCTCG

GTAACCTTTAAACTGAGGGCACTGAAGTCGCTTGATGTGCTGAATTGTTTG

TGATGTTGGTGGCGTATTTTGTTTAAATAAGTAAGCATGGCTGTGATTTTA

TCATATGATCGATCTTTGGGGTTTTATTTAACACATTGTAAAATGTGTATC

TATTAATAACTCAATGTATAAGATGTGTTCATTCTTCGGTTGCCATAGATC

TGCTTATTTGACCTGTGATGTTTTGACTCCAAAAACCAAAATCACAACTCA

ATAAACTCATGGAATATGTCCACCTGTTTCTTGAAGAGTTCATCTACCATT

CCAGTTGGCATTTATCAGTGTTGCAGCGGCGCTGTGCTTTGTAACATAACA

ATTGTTACGGCATATATCCAA
```

SEQ ID NO:6 shows an exemplary polynucleotide comprising the AAD-1 coding region (underlined), followed by a native tsh4 miR529-156 target site (double underlined) positioned between the end of the AAD-1 coding region and the ZmPer5 3'UTR (italics):

```
ATGGCTCATGCTGCCCTCAGCCCTCTCTCCCAACGCTTTGAGAGAATAGCT

GTCCAGCCACTCACTGGTGTCCTTGGTGCTGAGATCACTGGAGTGGACTTG

AGGGAACCACTTGATGACAGCACCTGGAATGAGATATTGGATGCCTTCCAC

ACTTACCAAGTCATCTACTTTCCTGGCCAAGCAATCACCAATGAGCAGCAC

ATTGCATTCTCAAGAAGGTTTGGACCAGTTGATCCAGTGCCTCTTCTCAAG

AGCATTGAAGGCTATCCAGAGGTTCAGATGATCCGCAGAGAAGCCAATGAG

TCTGGAAGGGTGATTGGTGATGACTGGCACACAGACTCCACTTTCCTTGAT

GCACCTCCAGCTGCTGTTGTGATGAGGGCCATAGATGTTCCTGAGCATGGC

GGAGACACTGGGTTCCTTTCAATGTACACAGCTTGGGAGACCTTGTCTCCA

ACCATGCAAGCCACCATCGAAGGGCTCAACGTTGTGCACTCTGCCACACGT

GTGTTCGGTTCCCTCTACCAAGCACAGAACCGTCGCTTCAGCAACACCTCA

GTCAAGGTGATGGATGTTGATGCTGGTGACAGAGAGACAGTCCATCCCTTG

GTTGTGACTCATCCTGGCTCTGGAAGGAAAGGCCTTTATGTGAATCAAGTC

TACTGTCAGAGAATTGAGGGCATGACAGATGCAGAATCAAAGCCATTGCTT

CAGTTCCTCTATGAGCATGCCACCAGATTTGACTTCACTTGCCGTGTGAGG

TGGAAGAAAGACCAAGTCCTTGTCTGGGACAACTTGTGCACCATGCACCGT

GCTGTTCCTGACTATGCTGGCAAGTTCAGATACTTGACTCGCACCACAGTT

GGTGGAGTTAGGCCTGCCCGCTGAGTAGTTAGCTTAATCACCTAGAGCTCG

ACTCCAGCTGTGCTCTCTCTCTTCTGTCAACTCAGGTAACCTTTAAACTGA

GGGCACTGAAGTCGCTTGATGTGCTGAATTGTTTGTGATGTTGGTGGCGTA
```

-continued

```
TTTTGTTTAAATAAGTAAGCATGGCTGTGATTTTATCATATGATCGATCTT

TGGGGTTTTATTTAACACATTGTAAAATGTGTATCTATTAATAACTCAATG

TATAAGATGTGTTCATTCTTCGGTTGCCATAGATCTGCTTATTTGACCTGT

GATGTTTTGACTCCAAAAACCAAAATCACAACTCAATAAACTCATGGAATA

TGTCCACCTGTTTCTTGAAGAGTTCATCTACCATTCCAGTTGGCATTTATC

AGTGTTGCAGCGGCGCTGTGCTTTGTAACATAACAATTGTTACGGCATATA

TCCAA
```

SEQ ID NO:7 shows an exemplary modified tsh4 target site comprising a native miR529 target site with a mutated miR156 target site:

```
GACTCAGGCTGTACTCTCTTACTTCACAAAGTACTCA
```

SEQ ID NO:8 shows a further exemplary modified tsh4 target site comprising a native miR529 target site with a mutated miR156 target site:

```
GACTCAGGCTGTACTCTCTCTCTTCACAAAGTACTCA
```

SEQ ID NO:9 shows an exemplary polynucleotide comprising the AAD-1 coding region (underlined), followed by an exemplary modified tsh4 target site (double underlined) comprising a mutated miR529 target site with a mutated miR156 target site, positioned between the end of the AAD-1 coding region and the ZmPer5 3'UTR (italics):

```
ATGGCTCATGCTGCCCTCAGCCCTCTCTCCCAACGCTTTGAGAGAATAGCT

GTCCAGCCACTCACTGGTGTCCTTGGTGCTGAGATCACTGGAGTGGACTTG

AGGGAACCACTTGATGACAGCACCTGGAATGAGATATTGGATGCCTTCCAC

ACTTACCAAGTCATCTACTTTCCTGGCCAAGCAATCACCAATGAGCAGCAC

ATTGCATTCTCAAGAAGGTTTGGACCAGTTGATCCAGTGCCTCTTCTCAAG

AGCATTGAAGGCTATCCAGAGGTTCAGATGATCCGCAGAGAAGCCAATGAG

TCTGGAAGGGTGATTGGTGATGACTGGCACACAGACTCCACTTTCCTTGAT

GCACCTCCAGCTGCTGTTGTGATGAGGGCCATAGATGTTCCTGAGCATGGC

GGAGACACTGGGTTCCTTTCAATGTACACAGCTTGGGAGACCTTGTCTCCA

ACCATGCAAGCCACCATCGAAGGGCTCAACGTTGTGCACTCTGCCACACGT

GTGTTCGGTTCCCTCTACCAAGCACAGAACCGTCGCTTCAGCAACACCTCA

GTCAAGGTGATGGATGTTGATGCTGGTGACAGAGAGACAGTCCATCCCTTG

GTTGTGACTCATCCTGGCTCTGGAAGGAAAGGCCTTTATGTGAATCAAGTC

TACTGTCAGAGAATTGAGGGCATGACAGATGCAGAATCAAAGCCATTGCTT

CAGTTCCTCTATGAGCATGCCACCAGATTTGACTTCACTTGCCGTGTGAGG

TGGAAGAAAGACCAAGTCCTTGTCTGGGACAACTTGTGCACCATGCACCGT

GCTGTTCCTGACTATGCTGGCAAGTTCAGATACTTGACTCGCACCACAGTT

GGTGGAGTTAGGCCTGCCCGCTGAGTAGTTAGCTTAATCACCTAGAGCTCG

ACTCAGGCTGTACTCTCTTACTTCACAAAGTACTCAGGTAACCTTTAAACT

GAGGGCACTGAAGTCGCTTGATGTGCTGAATTGTTTGTGATGTTGGTGGCG

TATTTTGTTTAAATAAGTAAGCATGGCTGTGATTTTATCATATGATCGATC
```

-continued

TTTGGGGTTTTATTTAACACATTGTAAAATGTGTATCTATTAATAACTCAA

TGTATAAGATGTGTTCATTCTTCGGTTGCCATAGATCTGCTTATTTGACCT

GTGATGTTTTGACTCCAAAAACCAAAATCACAACTCAATAAACTCATGGAA

TATGTCCACCTGTTTCTTGAAGAGTTCATCTACCATTCCAGTTGGCATTTA

TCAGTGTTGCAGCGGCGCTGTGCTTTGTAACATAACAATTGTTACGGCATA

TATCCAA

SEQ ID NO:10 shows an exemplary polynucleotide comprising the AAD-1 coding region (underlined), followed by a further exemplary modified tsh4 target site (double underlined) comprising a mutated miR529 target site with a mutated miR156 target site, positioned between the end of the AAD-1 coding region and the ZmPer5 3'UTR (italics):

ATGGCTCATGCTGCCCTCAGCCCTCTCTCCCAACGCTTTGAGAGAATAGCT

GTCCAGCCACTCACTGGTGTCCTTGGTGCTGAGATCACTGGAGTGGACTTG

AGGGAACCACTTGATGACAGCACCTGGAATGAGATATTGGATGCCTTCCAC

ACTTACCAAGTCATCTACTTTCCTGGCCAAGCAATCACCAATGAGCAGCAC

ATTGCATTCTCAAGAAGGTTTGGACCAGTTGATCCAGTGCCTCTTCTCAAG

AGCATTGAAGGCTATCCAGAGGTTCAGATGATCCGCAGAGAAGCCAATGAG

TCTGGAAGGGTGATTGGTGATGACTGGCACACAGACTCCACTTTCCTTGAT

GCACCTCCAGCTGCTGTTGTGATGAGGGCCATAGATGTTCCTGAGCATGGC

GGAGACACTGGGTTCCTTTCAATGTACACAGCTTGGGAGACCTTGTCTCCA

ACCATGCAAGCCACCATCGAAGGGCTCAACGTTGTGCACTCTGCCACACGT

GTGTTCGGTTCCCTCTACCAAGCACAGAACCGTCGCTTCAGCAACACCTCA

GTCAAGGTGATGGATGTTGATGCTGGTGACAGAGAGACAGTCCATCCCTTG

GTTGTGACTCATCCTGGCTCTGGAAGGAAAGGCCTTTATGTGAATCAAGTC

TACTGTCAGAGAATTGAGGGCATGACAGATGCAGAATCAAAGCCATTGCTT

CAGTTCCTCTATGAGCATGCCACCAGATTTGACTTCACTTGCCGTGTGAGG

TGGAAGAAAGACCAAGTCCTTGTCTGGGACAACTTGTGCACCATGCACCGT

GCTGTTCCTGACTATGCTGGCAAGTTCAGATACTTGACTCGCACCACAGTT

GGTGGAGTTAGGCCTGCCCGCTGAGTAGTTAGCTTAATCACCTAGAGCTCG

ACTCAGGCTGTACTCTCTCTCTTCACAAAGTACTCAGGTAACCTTTAAACT

GAGGGCACTGAAGTCGCTTGATGTGCTGAATTGTTTGTGATGTTGGTGGCG

TATTTTGTTTAAATAAGTAAGCATGGCTGTGATTTTATCATATGATCGATC

TTTGGGGTTTTATTTAACACATTGTAAAATGTGTATCTATTAATAACTCAA

TGTATAAGATGTGTTCATTCTTCGGTTGCCATAGATCTGCTTATTTGACCT

GTGATGTTTTGACTCCAAAAACCAAAATCACAACTCAATAAACTCATGGAA

TATGTCCACCTGTTTCTTGAAGAGTTCATCTACCATTCCAGTTGGCATTTA

TCAGTGTTGCAGCGGCGCTGTGCTTTGTAACATAACAATTGTTACGGCATA

TATCCAA

SEQ ID NO:11 shows an artificial miRNA, referred to herein as CMSRF9973.1:

GGATCCCAGCAGCAGCCACAGCAAAATTTGGTTTGGGATAGGTAGGTGTTA

TGTTAGGTCTGGTTTTTTGGCTGTAGCAGCAGCAGAGAAGAGAGAGAGTAC

AGCCTCAGGAGATTCAGTTTGAAGCTGGACTTCACTTTTGCCTCTCTAGGC

TCTACACTCTCTCTTCTTTCCTGCTGCTAGGCTGTTCTGTGGAAGTTTGCA

GAGTTTATATTATGGGTTTAATCGTCCATGGCATCAGCATCAGCAGCATTT

AAATGAGCTCGGTAACC

SEQ ID NO:12 shows an SCBV promoter, utilized in certain examples herein:

TCGGAAGTTGAAGACAAAGAAGGTCTTAAATCCTGGCTAGCAACACTGAAC

TATGCCAGAAACCACATCAAAGCATATCGGCAAGCTTCTTGGCCCATTATA

TCCAAAGACCTCAGAGAAAGGTGAGCGAAGGCTCAATTCAGAAGATTGGAA

GCTGATCAATAGGATCAAGACAATGGTGAGAACGCTTCCAAATCTCACTAT

TCCACCAGAAGATGCATACATTATCATTGAAACAGATGCATGTGCAACTGG

ATGGGGAGCAGTATGCAAGTGGAAGAAAAACAAGGCAGACCCAAGAAATAC

AGAGCAAATCTGTAGGTATGCCAGTGGAAAATTTGATAAGCCAAAAGGAAC

CTGTGATGCAGAAATCTATGGGGTTATGAATGGCTTAGAAAAGATGAGATT

GTTCTACTTGGACAAAAGAGAGATCACAGTCAGAACTGACAGTAGTGCAAT

CGAAAGGTTCTACAACAAGAGTGCTGAACACAAGCCTTCTGAGATCAGATG

GATCAGGTTCATGGACTACATCACTGGTGCAGGACCAGAGATAGTCATTGA

ACACATAAAAGGGAAGAGCAATGGTTTAGCTGACATCTTGTCCAGGCTCAA

AGCCAAATTAGCTCAGAATGAACCAACGGAAGAGATGATCCTGCTTACACA

AGCCATAAGGGAAGTAATTCCTTATCCAGATCATCCATACACTGAGCAACT

CAGAGAATGGGGAAACAAAATTCTGGATCCATTCCCCACATTCAAGAAGGA

CATGTTCGAAAGAACAGAGCAAGCTTTTATGCTAACAGAGGAACCAGTTCT

ACTCTGTGCATGCAGGAAGCCTGCAATTCAGTTAGTGTCCAGAACATCTGC

CAACCCAGGAAGGAAATTCTTCAAGTGCGCAATGAACAAATGCCATTGCTG

GTACTGGGCAGATCTCATTGAAGAACACATTCAAGACAGAATTGATGAATT

TCTCAAGAATCTTGAAGTTCTGAAGACCGGTGGCGTGCAAACAATGGAGGA

GGAACTTATGAAGGAAGTCACCAAGCTGAAGATAGAAGAGCAGGAGTTCGA

GGAATACCAGGCCACACCAAGGGCTATGTCGCCAGTAGCCGCAGAAGATGT

GCTAGATCTCCAAGACGTAAGCAATGACGATTGAGGAGGCATTGACGTCAG

GGATGACCGCAGCGGAGAGTACTGGGCCCATTCAGTGGATGCTCCACTGAG

TTGTATTATTGTGTGCTTTTCGGACAAGTGTGCTGTCCACTTTCTTTTGGC

ACCTGTGCCACTTTATTCCTTGTCTGCCACGATGCCTTTGCTTAGCTTGTA

AGCAAGGATCGCAGTGCGTGTGTGACACCACCCCCCTTCCGACGCTCTGCC

TATATAAGGCACCGTCTGTAAGCTCTTACGATCATCGGTAGTTCACCAAGG

C

SEQ ID NO:13 shows a synthetic 5' UTR, utilized in certain examples herein:

```
CTGAAGGCTCGACAAGGCAGTCCACGGAGGAGCTGATATTTGGTGGACAAG    5

CTGTGGATAGGAGCAACCCTATCCCTAATATACCAGCACCACCAAGTCAGG

GCAATCCCCAGATCACCCCAGCAGATTCGAAGAAGGTACAGTACACACACA

TGTATATATGTATGATGTATCCCTTCGATCGAAGGCATGCCTTGGTATAAT    10

CACTGAGTAGTCATTTTATTACTTTGTTTTGACAAGTCAGTAGTTCATCCA

TTTGTCCCATTTTTTCAGCTTGGAAGTTTGGTTGCACTGGCCTTGGTCTAA

TAACTGAGTAGTCATTTTATTACGTTGTTTCGACAAGTCAGTAGCTCATCC    15

ATCTGTCCCATTTTTTCAGCTAGGAAGTTTGGTTGCACTGGCCTTGGACTA

ATAACTGATTAGTCATTTTATTACATTGTTTCGACAAGTCAGTAGCTCATC

CATCTGTCCCATTTTTCAGCTAGGAAGTTCGGATCTGGGGCCATTTGTTCC    20

AGGCACGGGATAAGCATTCAG
```

SEQ ID NO:14 shows a maize Invertase (INV) gene (GenBank™ Accession No. U16123).

SEQ ID NO:15 shows a maize Elongation Factor 1α (EF1α) gene (GenBank™ Accession No. AF136823.1).

SEQ ID NOs: 16-31 show oligonucleotides utilized in certain examples herein.

DETAILED DESCRIPTION

I. Overview of Several Embodiments

Embodiments herein exploit tissue-specific expression of sRNAs to repress/knockdown the expression of a transgene in the specific tissue. sRNAs have been shown to regulate diverse developmental processes, including organ separation, polarity, and identity, and to modulate their own biogenesis and function. In embodiments herein, the precision and specificity of sRNA-mediated gene regulation is utilized to accomplish the tissue-specific expression of a transgene. In examples, a target site for a tissue-specific sRNA (e.g., an endogenous tissue-specific sRNA) is engineered into the transgene to reduce or eliminate expression of the transgene in the tissue. Embodiments herein may be utilized to target the expression of any transgene to any particular tissue(s).

Particular embodiments herein are useful, for example, in preferentially repressing expression of an herbicide selection gene in male tissues (e.g., tassel, pollen, anther, and stamen) to induce male sterility via herbicide application. Examples of this novel cellular engineering approach will save enormous resources, for example, by reducing or eliminating the need to employ expensive manual detasseling procedures during hybrid seed production. In addition, some examples avoid yield loss that is due to plant damage occurring during detasseling processes.

II. Abbreviations dsRNA double-stranded ribonucleic acid
GI growth inhibition
NCBI National Center for Biological Information
gDNA genomic DNA
iRNA inhibitory ribonucleic acid
ORF open reading frame
RNAi ribonucleic acid interference
miRNA micro inhibitory ribonucleic acid
SRNA small ribonucleic acid siRNA small inhibitory ribonucleic acid, or short, interfering
ribonucleic acid
hpRNA hairpin ribonucleic acid
UTR untranslated region
PCR polymerase chain reaction
RISC RNA-induced Silencing Complex III. Terms In the description and tables which follow, a number of terms are used. In order to provide a clear and consistent understanding of the specification and claims, including the scope to be given such terms, the following definitions are provided:

Backcrossing: Backcrossing methods may be used to introduce a nucleic acid sequence into plants. The backcrossing technique has been widely used for decades to introduce new traits into plants. N. Jensen, Ed. *Plant Breeding Methodology*, John Wiley & Sons, Inc., 1988. In a typical backcross protocol, the original variety of interest (recurrent parent) is crossed to a second variety (non-recurrent parent) that carries a gene of interest to be transferred. The resulting progeny from this cross are then crossed again to the recurrent parent, and the process is repeated until a plant is obtained wherein essentially all of the desired morphological and physiological characteristics of the recurrent plant are recovered in the converted plant, in addition to the transferred gene from the non-recurrent parent.

Expression: As used herein, "expression" of a coding sequence (for example, a gene or a transgene) refers to the process by which the coded information of a nucleic acid transcriptional unit (including, e.g., genomic DNA or cDNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

Genetic material: As used herein, the term "genetic material" includes all genes, and nucleic acid molecules, such as DNA and RNA.

Inhibition: As used herein, the term "inhibition," when used to describe an effect on a coding sequence (for example, a gene), refers to a measurable decrease in the cellular level of mRNA transcribed from the coding sequence and/or peptide, polypeptide, or protein product of the coding sequence. In some examples, expression of a coding sequence may be inhibited such that expression is essentially eliminated (e.g., expression is reduced to less than 10%, 9%, 8%, 7%, 6%, 5%, 4%, 3%, 2%, or 1% of its expression in a control cell).

Isolated: An "isolated" biological component (such as a nucleic acid or protein) has been substantially separated, produced apart from, or purified away from other biological components in the cell of the organism in which the component naturally occurs (i.e., other chromosomal and extrachromosomal DNA and RNA, and proteins), while effecting a chemical or functional change in the component (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods, wherein there has been a chemical or functional change in the nucleic acid or protein. The term also embraces nucleic acids and proteins prepared by recombinant expression in a host cell, as well as chemically-synthesized nucleic acid molecules, proteins, and peptides.

Nucleic acid molecule: As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The nucleotide sequence of a nucleic acid molecule is read from the 5' to the 3' end of the molecule by convention. The "complement" of a nucleotide sequence refers to the sequence, from 5' to 3', of the nucleobases which form base pairs with the nucleobases of the nucleotide sequence (i.e., A-T/U, and G-C). The "reverse complement" of a nucleic acid sequence refers to the sequence, from 3' to 5', of the nucleobases which form base pairs with the nucleobases of the nucleotide sequence.

"Nucleic acid molecules" include single- and double-stranded forms of DNA; single-stranded forms of RNA; and double-stranded forms of RNA (dsRNA). The term "nucleotide sequence" or "nucleic acid sequence" refers to both the sense and antisense strands of a nucleic acid as either individual single strands or in the duplex. The term "ribonucleic acid" (RNA) is inclusive of iRNA (inhibitory RNA), dsRNA (double-stranded RNA), sRNA (small RNA), siRNA (small interfering RNA), miRNA (micro-RNA), hpRNA (hairpin RNA), mRNA (messenger RNA), tRNA (transfer RNA), and cRNA (complementary RNA). The term "deoxyribonucleic acid" (DNA) is inclusive of cDNA, genomic DNA, and DNA-RNA hybrids. The term "polynucleotide" will be understood by those in the art as a structural term that is defined by its nucleotide sequence, and that includes genomic sequences, ribosomal RNA sequences, transfer RNA sequences, messenger RNA sequences, operon sequences, and smaller engineered nucleotide sequences.

Small RNA (sRNA): sRNAs are non-coding RNAs that regulate gene expression by pairing to the message of protein-coding genes to guide mRNA cleavage or repression of productive translation. Dugas and Bartel (2004) *Curr. Opin. Plant Biolo.* 7:512-20. As used herein, the term "small RNA" (sRNA) includes, for example, microRNA (miRNA), small interfering RNA (siRNA), trans-acting small interfering RNA (tasiRNA), and other sRNAs guiding cleavage, translational repression, and/or gene silencing.

Small interfering RNA (siRNA): RNA of approximately 21-25 nucleotides that is processed from a dsRNA by a DICER enzyme (in animals) or a DCL enzyme (in plants). The initial DICER or DCL products are double-stranded, in which the two strands are typically 21-25 nucleotides in length and contain two unpaired bases at each 3' end. The individual strands within the double stranded siRNA structure are separated, and typically one of the siRNAs then are associated with a multi-subunit complex, the RNAi-induced silencing complex (RISC). A typical function of the siRNA is to guide RISC to the target based on base-pair complementarity.

Target nucleic acid (to be inhibited): As used herein, the term "target," in reference to a polynucleotide, refers to any nucleic acid containing a sequence that interacts with a miRNA or siRNA, or that has the potential to yield a sequence that interacts with a miRNA or siRNA (for example, through transcription of a locus). The target can be a cellular nucleic acid, such as an mRNA that encodes an essential or nonessential protein, or a foreign nucleic acid, such as a virus-derived or transgene-derived RNA molecule. The target can be a DNA sequence corresponding to a promoter, or a sequence corresponding to any expressed region of a genome, for instance.

Oligonucleotide: An oligonucleotide is a short nucleic acid molecule. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer," which allows a DNA polymerase to extend the oligonucleotide and replicate the complementary strand.

A nucleic acid molecule may include either or both naturally occurring and modified nucleotides linked together by naturally occurring and/or non-naturally occurring nucleotide linkages. Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, inter-nucleotide modifications (e.g., uncharged linkages: for example, methyl phosphonates, phosphotriesters, phosphoramidates, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

As used herein with respect to DNA, the term "coding sequence" refers to a nucleotide sequence that is transcribed into RNA when placed under the control of appropriate regulatory sequences. A "protein coding sequence" is a nucleotide sequence (DNA or RNA) that is ultimately translated into a polypeptide, via transcription and mRNA. With respect to RNA, the term "coding sequence" refers to a nucleotide sequence that is translated into a peptide, polypeptide, or protein. The boundaries of a coding sequence are determined by a translation start codon at the 5'-terminus and a translation stop codon at the 3'-terminus. Coding sequences include, but are not limited to: genomic DNA; cDNA; EST; and recombinant nucleotide sequences.

Genome: As used herein, the term "genome" refers to chromosomal DNA found within the nucleus of a cell, and also refers organelle DNA found within subcellular components of the cell. In some embodiments of the invention, a DNA molecule may be introduced into a plant cell such that the DNA molecule is integrated into the genome of the plant cell. In these and further embodiments, the DNA molecule may be either integrated into the nuclear DNA of the plant cell, or integrated into the DNA of the chloroplast or mitochondrion of the plant cell.

Endogenous: The term "endogenous," as applied to nucleic acids (e.g., polynucleotides, DNA, RNA, and genes) herein, refers to one or more nucleic acid(s) that are normally (e.g., in a wild-type cell of the same type and species) present within their specific environment or context. For example, an endogenous gene is one that is normally found in the particular cell in question and in the same context (e.g., with regard to regulatory sequences). Endogenous nucleic acids can be distinguished from exogenous and/or heterologous, for example and without limitation, by detection in the latter of sequences that are consequent with recombination from bacterial plasmid; identification of atypical codon preferences; and amplification of atypical sequences in a PCR reaction from primers characterized in a wild-type cell.

Exogenous: The term "exogenous," as applied to nucleic acids herein, refers to one or more nucleic acid(s) that are not normally present within their specific environment or context. For example, if a host cell is transformed with a nucleic acid that does not occur in the untransformed host cell in nature, then that nucleic acid is exogenous to the host cell. The term exogenous, as used herein, also refers to one or more nucleic acid(s) that are identical in sequence to a nucleic acid already present in a host cell, but that are located in a different cellular or genomic context than the nucleic acid with the same sequence already present in the host cell. For example, a nucleic acid that is integrated in the genome of the host cell in a different location than a nucleic acid with the same sequence is normally integrated in the genome of the host cell is exogenous to the host cell. Furthermore, a nucleic acid (e.g., a DNA molecule) that is present in a plasmid or vector in the host cell is exogenous to the host cell when a nucleic acid with the same sequence is only normally present in the genome of the host cell.

Heterologous: The term "heterologous," as applied to nucleic acids (e.g., polynucleotides, DNA, RNA, and genes) herein, means of different origin. For example, if a host cell is transformed with a nucleic acid that does not occur in the untransformed host cell in nature, then that nucleic acid is heterologous (and exogenous) to the host cell. Furthermore, different elements (e.g., promoter, enhancer, coding sequence, terminator, etc.) of a transforming nucleic acid may be heterologous to one another and/or to the transformed host. The term heterologous, as used herein, may also be applied to one or more nucleic acid(s) that are identical in sequence to a nucleic acid already present in a host cell, but that are now linked to different additional sequences and/or are present at a different copy number, etc.

Sequence identity: The term "sequence identity" or "identity," as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50. A detailed consideration of sequence alignment methods and homology calculations can be found in, e.g., Altschul et al. (1990) *J. Mol. Biol.* 215:403-10.

The National Center for Biotechnology Information (NCBI) Basic Local Alignment Search Tool (BLAST™; Altschul et al. (1990)) is available from several sources, including the National Center for Biotechnology Information (Bethesda, MD), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

Specifically hybridizable/specifically complementary: As used herein, the terms "specifically hybridizable" and "specifically complementary" are terms that indicate a sufficient degree of complementarity such that stable and specific binding occurs between the nucleic acid molecule and a target nucleic acid molecule. Hybridization between two nucleic acid molecules involves the formation of an anti-parallel alignment between the nucleic acid sequences of the two nucleic acid molecules. The two molecules are then able to form hydrogen bonds with corresponding bases on the opposite strand to form a duplex molecule that, if it is sufficiently stable, is detectable using methods well known in the art. A nucleic acid molecule need not be 100% complementary to its target sequence to be specifically hybridizable. However, the amount of sequence complementarity that must exist for hybridization to be specific is a function of the hybridization conditions used.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Calculations regarding hybridization conditions required for attaining particular degrees of stringency are known to those of ordinary skill in the art, and are discussed, for example, in Sambrook et al. (ed.) *Molecular Cloning: A Laboratory Manual*, 2nd ed., vol. 1-3, Cold Spring Harbor Laboratory Press, Cold Spring Harbor, NY, 1989, chapters 9 and 11; and Hames and Higgins (eds.) *Nucleic Acid Hybridization*, IRL Press, Oxford, 1985. Further detailed instruction and guidance with regard to the hybridization of nucleic acids may be found, for example, in Tijssen, "Overview of principles of hybridization and the strategy of nucleic acid probe assays," in *Laboratory Techniques in Biochemistry and Molecular Biology-Hybridization with Nucleic Acid Probes*, Part I, Chapter 2, Elsevier, NY, 1993; and Ausubel et al., Eds., *Current Protocols in Molecular Biology*, Chapter 2, Greene Publishing and Wiley-Interscience, NY, 1995.

As used herein, "stringent conditions" encompass conditions under which hybridization will only occur if there is less than 20% mismatch between the hybridization molecule and a homologous sequence within the target nucleic acid molecule. "Stringent conditions" include further particular levels of stringency. Thus, as used herein, "moderate stringency" conditions are those under which molecules with more than 20% sequence mismatch will not hybridize; conditions of "high stringency" are those under which sequences with more than 10% mismatch will not hybridize; and conditions of "very high stringency" are those under which sequences with more than 5% mismatch will not hybridize.

The following are representative, non-limiting hybridization conditions.

High Stringency condition (detects sequences that share at least 90% sequence identity): Hybridization in 5×SSC buffer at 65° C. for 16 hours; wash twice in 2×SSC buffer at room temperature for 15 minutes each; and wash twice in 0.5× SSC buffer at 65° C. for 20 minutes each.

Moderate Stringency condition (detects sequences that share at least 80% sequence identity): Hybridization in 5×-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Non-stringent control condition (sequences that share at least 50% sequence identity will hybridize): Hybridization in 6×SSC buffer at room temperature to 55° C. for 16-20 hours; wash at least twice in 2×-3×SSC buffer at room temperature to 55° C. for 20-30 minutes each.

As used herein, the term "substantially homologous" or "substantial homology," with regard to a polynucleotide, refers to polynucleotides that hybridize under stringent conditions to the reference nucleic acid sequence. For example, polynucleotides that are substantially homologous to a reference DNA coding sequence are those polynucleotides that hybridize under stringent conditions (e.g., the Moderate Stringency conditions set forth, supra) to the reference DNA coding sequence. Substantially homologous sequences may have at least 80% sequence identity. For example, substantially homologous sequences may have from about 80% to 100% sequence identity, such as about 81%; about 82%; about 83%; about 84%; about 85%; about 86%; about 87%; about 88%; about 89%; about 90%; about 91%; about 92%; about 93%; about 94% about 95%; about 96%; about 97%; about 98%; about 98.5%; about 99%; about 99.5%; and about 100%. The property of substantial homology is closely related to specific hybridization. For example, a nucleic acid molecule is specifically hybridizable when there is a sufficient degree of complementarity to avoid non-specific binding of the nucleic acid to non-target sequences under conditions where specific binding is desired, for example, under stringent hybridization conditions.

As used herein, the term "ortholog" refers to a gene in two or more species that has evolved from a common ancestral nucleotide sequence, and may retain the same function in the two or more species.

DNA has two antiparallel strands, a 5'→3' strand, referred to as the plus strand, and a 3'→5' strand, referred to as the minus strand. Because RNA polymerase adds nucleic acids in a 5'→3' direction, the minus strand of the DNA serves as the template for the RNA during transcription. Thus, an RNA transcript will have a sequence complementary to the minus strand, and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a DNA target. An antisense RNA is a molecule of RNA complementary to a sense (encoding) nucleic acid molecule.

As used herein, two nucleic acid sequence molecules are said to exhibit "complete complementarity" when every nucleotide of a sequence read in the 5' to 3' direction is complementary to every nucleotide of the other sequence when read in the 3' to 5' direction. A nucleotide sequence that is complementary to a reference nucleotide sequence will exhibit a sequence identical to the reverse complement sequence of the reference nucleotide sequence. These terms and descriptions are well defined in the art and are easily understood by those of ordinary skill in the art.

As used herein, the term "substantially identical" may refer to nucleotide sequences that are more than 85% identical. For example, a substantially identical nucleotide sequence may be at least 85.5%; at least 86%; at least 87%; at least 88%; at least 89%; at least 90%; at least 91%; at least 92%; at least 93%; at least 94%; at least 95%; at least 96%; at least 97%; at least 98%; at least 99%; or at least 99.5% identical to the reference sequence.

Operably linked: A first nucleotide sequence is operably linked with a second nucleic acid sequence when the first nucleic acid sequence is in a functional relationship with the second nucleic acid sequence. When recombinantly produced, operably linked nucleic acid sequences are generally contiguous, and, where necessary to join two protein-coding regions, in the same reading frame (e.g., in a polycistronic ORF). However, nucleic acids need not be contiguous to be operably linked.

The term, "operably linked," when used in reference to a regulatory sequence and a coding sequence, means that the regulatory sequence affects the expression of the linked coding sequence. "Regulatory sequences," or "control elements," refer to nucleotide sequences that influence the timing and level/amount of transcription, RNA processing or stability, or translation of the associated coding sequence. Regulatory sequences may include promoters; translation leader sequences; introns; enhancers; stem-loop structures; repressor binding sequences; termination sequences; polyadenylation recognition sequences; etc. Particular regulatory sequences may be located upstream and/or downstream of a coding sequence operably linked thereto. Also, particular regulatory sequences operably linked to a coding sequence may be located on the associated complementary strand of a double-stranded nucleic acid molecule.

Promoter: As used herein, the term "promoter" refers to a region of DNA that may be upstream from the start of transcription, and that may be involved in recognition and binding of RNA polymerase and other proteins to initiate transcription. A promoter may be operably linked to a coding sequence for expression in a cell, or a promoter may be operably linked to a nucleotide sequence encoding a signal sequence which may be operably linked to a coding sequence for expression in a cell.

Some embodiments herein include a "plant promoter." A plant promoter is a promoter that is capable of initiating transcription in a plant cell.

Some embodiments herein include a "tissue-preferred promoter." A tissue-preferred promoter is a promoter that is capable of initiating transcription under developmental control, and include, for example and without limitation: promoters that preferentially initiate transcription in leaves, pollen, tassels, roots, seeds, fibers, xylem vessels, tracheids, and sclerenchyma. Promoters that initiate transcription essentially only in certain tissues are referred to as "tissue-specific." A "cell type-specific" promoter primarily drives expression in certain cell types in one or more organs, for example, vascular cells in roots or leaves. An "inducible" promoter may be a promoter which may be under environmental control. Examples of environmental conditions that may initiate transcription by inducible promoters include anaerobic conditions and the presence of light. Tissue-specific, tissue-preferred, cell type specific, and inducible promoters constitute the class of "non-constitutive" promoters.

Any inducible promoter may be used in some embodiments of the invention. See Ward et al. (1993) *Plant Mol. Biol.* 22:361-366. With an inducible promoter, the rate of transcription increases in response to an inducing agent. Exemplary inducible promoters include, but are not limited to: Promoters from the ACEI system that responds to copper; In2 gene from maize that responds to benzenesulfo-namide herbicide safeners; Tet repressor from Tn10; and the inducible promoter from a steroid hormone gene, the transcriptional activity of which may be induced by a glucocorticosteroid hormone (Schena et al. (1991) *Proc. Natl. Acad. Sci. USA* 88:10421-5).

In contrast to non-constitutive promoters, a "constitutive" promoter is a promoter that is active under most environmental conditions. Exemplary constitutive promoters include, but are not limited to: promoters from plant viruses, such as the 35S promoter from CaMV; promoters from rice actin genes; ubiquitin promoters; pEMU; MAS; maize H3 histone promoter; and the ALS promoter, Xbal/NcoI fragment 5' to the *Brassica napus* ALS3 structural gene (or a nucleotide sequence similarity to said Xbal/NcoI fragment) (PCT International Patent Publication No. WO96/30530).

Additionally, any tissue-specific or tissue-preferred promoter may be utilized in some embodiments of the invention. Plants transformed with a nucleic acid molecule comprising a coding sequence operably linked to a tissue-specific promoter may produce the product of the coding sequence exclusively, or preferentially, in a specific tissue. Exemplary tissue-specific or tissue-preferred promoters include, but are not limited to: a root-preferred promoter, such as that from the phaseolin gene; a leaf-specific and light-induced promoter such as that from cab or rubisco; an anther-specific promoter such as that from LAT52; a pollen-specific promoter such as that from Zm13; and a microspore-preferred promoter such as that from apg.

Trait or phenotype: The terms "trait" and "phenotype" are used interchangeably herein. For the purposes of the present disclosure, traits of particular interest include agronomically important traits, as may be expressed, for example, in a crop plant. In some examples, a trait of particular interest is male sterility.

Transformation: As used herein, the term "transformation" refers to the transfer of one or more nucleic acid molecule(s) into a cell. A cell is "transformed" by a nucleic acid molecule introduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell. Examples include, but are not limited to: transfection with viral vectors; transformation with plasmid vectors; electroporation (Fromm et al. (1986) *Nature* 319:791-3); lipofection (Felgner et al. (1987) *Proc. Natl. Acad. Sci. USA* 84:7413-7); microinjection (Mueller et al. (1978) *Cell* 15:579-85); *Agrobacterium*-mediated transfer (Fraley et al. (1983) *Proc. Natl. Acad. Sci. USA* 80:4803-7); direct DNA uptake; and microprojectile bombardment (Klein et al. (1987) *Nature* 327:70).

Transgene: A transgene is an exogenous nucleic acid sequence. In some examples, a transgene may be a sequence that encodes one or both strand(s) of a dsRNA molecule that comprises a nucleotide sequence that is complementary to a target nucleic acid. In some examples, a transgene may be an antisense nucleic acid sequence, the expression of which inhibits expression of a target nucleic acid. In still other examples, a transgene may be a gene sequence (e.g., a herbicide-resistance gene), a gene encoding an industrially or pharmaceutically useful compound, or a gene encoding a desirable agricultural trait. In these and other examples, a transgene may contain regulatory sequences operably linked to the coding sequence of the transgene (e.g., a promoter).

Vector: A vector refers to a nucleic acid molecule as introduced into a cell, for example, to produce a transformed cell. A vector may include nucleic acid sequences that permit it to replicate in the host cell, such as an origin of replication. Examples of vectors include, but are not limited to: a plasmid; cosmid; bacteriophage; and a virus that carries exogenous DNA into a cell. A vector may also include one or more genes, antisense molecules, and/or selectable marker genes and other genetic elements known in the art. A vector may transduce, transform, or infect a cell, thereby causing the cell to express the nucleic acid molecules and/or proteins encoded by the vector. A vector optionally includes materials to aid in achieving entry of the nucleic acid molecule into the cell (e.g., a liposome, protein coating, etc.).

Unless specifically indicated or implied, the terms "a," "an," and "the" signify "at least one," as used herein.

Unless otherwise specifically explained, all technical and scientific terms used herein have the same meaning as commonly understood by those of ordinary skill in the art to which this disclosure belongs. Definitions of common terms in molecular biology can be found in, for example, B. Lewin, *Genes V*, Oxford University Press, 1994 (ISBN 0-19-854287-9); Kendrew et al. (eds.), *The Encyclopedia of Molecular Biology*, Blackwell Science Ltd., 1994 (ISBN 0-632-02182-9); and R. A. Meyers (ed.), *Molecular Biology and Biotechnology: A Comprehensive Desk Reference*, VCH Publishers, Inc., 1995 (ISBN 1-56081-569-8). All percentages are by weight and all solvent mixture proportions are by volume unless otherwise noted. All temperatures are in degrees Celsius.

Iv. Nucleic Acids and Systems

Plants and animals use sRNAs to direct the post-transcriptional and epigenetic regulation of target genes. Many miRNAs and their corresponding target sequences are highly conserved. For example, target sequences in plants that are recognized by related miRNAs in different species often differ only by several nucleotides. Therefore, the computational prediction of target sites is possible. Jones- Rhoades and Bartel (2004) *Mol. Cell* 14:787-99. Additionally, a functional sRNA target site from one plant species is likely to be functional in a different plant species that expresses the targeting sRNA. For example, miRNA target genes from *Arabidopsis* heterologously expressed in *Nicotiana* are cleaved by endogenous *Nicotiana* miRNAs. Llave et al. (2002) *Science* 297:2053-6.

Embodiments herein include nucleic acids comprising a target site for at least one sRNA molecule. A target site for an sRNA molecule may be, for example, between about 20-30 nucleotides in length. For example, such a target site may be between about 20-25 or 20-21 nucleotides in length. In particular examples, the target site may be 19, about 20, about 21, about 22, about 23, about 24, about 25, about 26, about 27, about 28, about 29, about 30, or 31 nucleotides in length. Target sites for particular sRNAs may by identified or engineered computationally, using program parameters that may be selected within the discretion of those skilled in the art. Target sites may be identified or engineered to be specifically targeted by a single sRNA, or to be targeted by a group of related sRNAs.

Particular embodiments include nucleic acids, comprising, for example, a gene or coding region of interest that comprises an sRNA target site (e.g., an internal target site that is located within a transcribed portion of the gene or coding region), such that co-expression in a cell of the gene or coding region and the targeting sRNA results in reduced or essentially eliminated expression of the gene or coding region. Such nucleic acids may be, for example and without limitation, a heterologous or exogenous nucleic acid in the genome of a cell (e.g., a plant cell), or a vector.

In some embodiments, a nucleic acid comprising a gene or coding region of interest with an sRNA target site further comprises one or more regulatory sequences that are operably linked to the gene or coding region of interest, so as to effect the transcription of the gene or coding region of interest in a cell; i.e., an expression construct. In examples, the cell is a plant cell. In particular embodiments, the gene or coding region of interest is operably linked to a constitutive plant promoter in the expression construct. By, for example, transforming a plant cell or tissue with such an expression construct and regenerating a plant from the plant cell or tissue, a transgenic plant may be produced, wherein the gene or coding region of interest is transcribed in every cell or essentially every cell of the plant.

In embodiments, the gene or coding region of interest may be an agronomic gene or nucleotide sequence encoding a polypeptide of interest, and may also and/or alternatively include, for example and without limitation: genes that confer resistance to an herbicide, such as an herbicide that inhibits the growing point or meristem, for example, an imidazolinone or a sulfonylurea (exemplary genes in this category encode mutant ALS and AHAS enzymes, as described, for example, by Lee et al. (1988) *EMBO J.* 7:1241, and Miki et al. (1990) *Theor. Appl. Genet.* 80:449, respectively); glyphosate resistance as conferred by, e.g., mutant 5-enolpyruvylshikimate-3-phosphate synthase (EPSPs) genes (via the introduction of recombinant nucleic acids and/or various forms of in vivo mutagenesis of native EPSPs genes); aroA genes and glyphosate acetyl transferase (GAT) genes, respectively); other phosphono compounds, such as glufosinate phosphinothricin acetyl transferase (PAT) genes from *Streptomyces* species, including *Streptomyces hygroscopicus* and *Streptomyces viridichromogenes*); and pyridinoxy or phenoxy proprionic acids and cyclohexones (ACCase inhibitor-encoding genes). See, e.g., U.S. Pat. Nos. 4,940,835 and 6,248,876 (nucleotide sequences of forms of EPSPs which can confer glyphosate resistance to a plant). A DNA molecule encoding a mutant aroA gene can be obtained under ATCC accession number 39256. See also U.S. Pat. No. 4,769,061 (nucleotide sequence of a mutant aroA gene). European patent application No. 0 333 033 and U.S. Pat. No. 4,975,374 disclose nucleotide sequences of glutamine synthetase genes, which may confer resistance to herbicides such as L-phosphinothricin. Nucleotide sequences of exemplary PAT genes are provided in European application No. 0 242 246, andDeGree F. et al. (1989) *Bio/Technology* 7:61 (production of transgenic plants that express chimeric bar genes coding for PAT activity). Exemplary of genes conferring resistance to phenoxy proprionic acids and cyclohexones, such as sethoxydim and haloxyfop, include the Acc1-S1, Acc1-S2 and Acc1-S3 genes described by Marshall et al. (1992) *Theor. Appl. Genet.* 83:435. GAT genes capable of conferring glyphosate resistance are described, for example, in WO 2005012515. Genes conferring resistance to 2,4-D, phenoxyproprionic acid and pyridyloxy auxin herbicides are described, for example, in WO 2005107437.

Nucleic acids comprising an agronomic gene or nucleotide sequence encoding a polypeptide of interest may also include, for example and without limitation: a gene conferring resistance to an herbicide that inhibits photosynthesis, such as a triazine (psbA and gs+ genes) or a benzonitrile (nitrilase gene). See, e.g., Przibila et al. (1991) *Plant Cell* 3:169 (transformation of *Chlamydomonas* with plasmids encoding mutant psbA genes). Nucleotide sequences for nitrilase genes are disclosed in U.S. Pat. No. 4,810,648, and DNA molecules containing these genes are available under ATCC Accession Nos. 53435; 67441; and 67442. See also Hayes et al. (1992) *Biochem. J.* 285:173 (cloning and expression of DNA coding for a glutathione S-transferase).

Embodiments herein also or alternatively include a set of nucleic acids, wherein the set includes at least one nucleic acid comprising a target site for at least one sRNA molecule. In some embodiments, the set of nucleic acids further includes at least one nucleic acid encoding at least one sRNA molecule targeting the nucleic acid comprising the target site therefore. In particular embodiments, a plant cell may be transformed (either in one step or in multiple steps) with the nucleic acids of the set. In examples, when a transgenic plant tissue or plant is regenerated from the transformed plant cell, the nucleic acid comprising the target site for the at least one sRNA molecule is expressed essentially in all cells other than those wherein the sRNA molecule is expressed. Thus, when the set of nucleic acids includes a nucleic acid encoding the sRNA molecule under the control of a tissue-specific promoter, the nucleic acid comprising the target site for the at least one sRNA molecule is expressed essentially in all cells other than cells of the tissue wherein the promoter directs expression of the sRNA molecule.

V. Methods

In some embodiments herein, a plant cell, plant part, and/or plant may be genetically modified to comprise at least one nucleic acid comprising a target site for at least one sRNA molecule by any of several methods of introducing a heterologous molecule known in the art, thereby producing a non-natural transgenic plant cell, plant part, or plant. In particular embodiments herein, a heterologous molecule is introduced into a plant cell, plant part, and/or plant by a method selected from, for example and without limitation: transformation and selective breeding (e.g., backcross breeding).

In some embodiments, the nucleic acid is selected such that the target site is a target of an endogenous sRNA of the plant wherein the heterologous nucleic acid is introduced. In particular embodiments, the target site is the target site of an endogenous sRNA of the plant that is endogenously expressed in the plant in a tissue-preferred or tissue-specific manner.

Depending on the particular target gene and the level of production of the sRNA, embodiments herein may provide partial or complete loss of expression, or function, of the target gene. The inhibition in target gene expression in different embodiments is at least a 5%, at least a 10%, at least a 20%, at least a 30%, at least a 50%, at least a 75%, at least an 80%, at least an 85%, at least a 90%, at least a 95%, or a 100% inhibition in target gene expression. Any plant species or plant cell may be genetically modified to comprise a heterologous nucleic acid herein. In some embodiments, the plant cell that is so genetically modified is capable of regeneration to produce a plant. In some embodiments, plant cells that are genetically modified (e.g., host plant cells) include cells from, for example and without limitation, a higher plant, a dicotyledonous plant, a monocotyledonous plants, a consumable plant, a crop plant, and a plant utilized for its oils (e.g., an oilseed plant). Such plants include, for example and without limitation: alfalfa; soybean; cotton; rapeseed (canola); linseed; corn; rice; brachiaria; wheat; safflower; sorghum; sugarbeet; sunflower; tobacco; and grasses (e.g., turf grass). In particular examples, a genetically modified plant cell or plant herein includes, for example and without limitation: *Brassica napus*; Indian mustard (*Brassica juncea*); Ethiopian mustard (*Brassica carinata*); turnip (*Brassica rapa*); cabbage (*Brassica oleracea*); *Glycine max; Linum usitatissimum; Zea mays; Carthamus tinctorius; Helianthus annuus; Nicotiana tabacum; Arabidopsis thaliana*, Brazil nut (*Betholettia excelsa*); castor bean (*Ricinus communis*); coconut (*Cocus nucifera*); coriander (*Coriandrum sativum*); *Gossypium* spp.; groundnut (*Arachis hypogaea*); jojoba (*Simmondsia chinensis*); oil palm (*Elaeis guineeis*); olive (*Olea eurpaea*); *Oryza sativa*; squash (*Cucurbita maxima*); barley (*Hordeum vulgare*); sugarcane (*Saccharum officinarum*); *Triticum* spp. (including *Triticum durum* and *Triticum aestivum*); and duckweed (*Lemnaceae* sp.). In some embodiments, the plant may have a particular genetic background, as for elite cultivars, wild-type cultivars, and commercially distinguishable varieties.

According to methods known in the art, nucleic acids can be introduced into essentially any plant. Embodiments herein may employ any of the many methods for the transformation of plants (and production of genetically modified plants) that are known in the art. Such methods include, for example and without limitation, biological and physical transformation protocols for dicotyledenous plants, as well as monocotyledenous plants. See, e.g., Goto-Fumiyuki et al. (1999) *Nat. Biotechnol.* 17:282-6; Miki et al. (1993) *Methods in Plant Molecular Biology and Biotechnology* (B. R. Glick and J. E. Thompson, Eds.), CRC Press, Inc., Boca Raton, FL, pp. 67-88. In addition, vectors and in vitro culture methods for plant cell and tissue transformation and regeneration of plants are described, for example, in Gruber and Crosby (1993) *Methods in Plant Molecular Biology and Biotechnology*, supra, at pp. 89-119.

Plant transformation techniques available for introducing a nucleic acid into a plant host cell include, for example and without limitation: transformation with disarmed T-DNA using *Agrobacterium tumefaciens* or *A. rhizogenes* as the transformation agent; calcium phosphate transfection; poly-brene transformation; protoplast fusion; electroporation (D'Halluin et al. (1992) *Plant Cell* 4:1495-505); ultrasonic methods (e.g., sonoporation); liposome transformation; microinjection; contact with naked DNA; contact with plasmid vectors; contact with viral vectors; biolistics (e.g., DNA particle bombardment (see, e.g., Klein et al. (1987) *Nature* 327:70-3) and microparticle bombardment (Sanford et al. (1987) *Part. Sci. Technol.* 5:27; Sanford (1988) *Trends Biotech.* 6:299, Sanford (1990) *Physiol. Plant* 79:206; and Klein et al. (1992) Biotechnology 10:268); silicon carbide WHISKERS-mediated transformation (Kaeppler et al. (1990) *Plant Cell Rep.* 9:415-8); nanoparticle transformation (see, e.g., U.S. Patent Publication No. US2009/0104700A1); aerosol beaming; and polyethylene glycol (PEG)-mediated uptake. In specific examples, a heterologous nucleic acid may be introduced directly into the genomic DNA of a plant cell.

A widely utilized method for introducing an expression vector into a plant is based on the natural transformation system of *Agrobacterium*. Horsch et al. (1985) Science 227:1229. *A. tumefaciens* and *A. rhizogenes* are plant pathogenic soil bacteria known to be useful to genetically transform plant cells. The Ti and Ri plasmids of *A. tumefaciens* and *A. rhizogenes*, respectively, carry genes responsible for genetic transformation of the plant. Kado (1991) *Crit. Rev. Plant. Sci.* 10:1. Details regarding *Agrobacterium* vector systems and methods for *Agrobacterium*-mediated gene transfer are also available in, for example, Gruber et al., supra, Miki et al., supra, Moloney et al. (1989) *Plant Cell Reports* 8:238, and U.S. Pat. Nos. 4,940,838 and 5,464,763.

If *Agrobacterium* is used for the transformation, the DNA to be inserted typically is cloned into special plasmids; either into an intermediate vector or a binary vector. Intermediate vectors cannot replicate themselves in *Agrobacterium*. The intermediate vector may be transferred into *A. tumefaciens* by means of a helper plasmid (conjugation). The Japan Tobacco Superbinary system is an example of such a system (reviewed by Komari et al. (2006) *Methods in Molecular Biology* (K. Wang, ed.) No. 343; *Agrobacterium Protocols,* 2nd Edition, Vol. 1, Humana Press Inc., Totowa, NJ, pp. 15-41; and Komori et al. (2007) *Plant Physiol.* 145:1155-60). Binary vectors can replicate themselves both in *E. coli* and in *Agrobacterium*. Binary vectors comprise a selection marker gene and a linker or polylinker which are framed by the right and left T-DNA border regions. They can be transformed directly into *Agrobacterium* (Holsters, 1978). The *Agrobacterium* comprises a plasmid carrying a vir region. The Ti or Ri plasmid also comprises the vir region necessary for the transfer of the T-DNA. The vir region is necessary for the transfer of the T-DNA into the plant cell. Additional T-DNA may be contained.

The virulence functions of the *Agrobacterium tumefaciens* host will direct the insertion of a T-strand containing the construct and adjacent marker into the plant cell DNA when the cell is infected by the bacteria using a binary T DNA vector (Bevan (1984) *Nuc. Acid Res.* 12:8711-21) or the co-cultivation procedure (Horsch et al. (1985) *Science* 227:1229-31). Generally, the *Agrobacterium* transformation system is used to engineer dicotyledonous plants. Bevan et al. (1982) *Ann. Rev. Genet.* 16:357-84; Rogers et al. (1986) *Methods Enzymol.* 118:627-41. The *Agrobacterium* transformation system may also be used to transform, as well as transfer, nucleic acids to monocotyledonous plants and plant cells. See U.S. Pat. No. 5,591,616; Hernalsteen et al. (1984) *EMBO J.* 3:3039-41; Hooykass-Van Slogteren et al. (1984) *Nature* 311:763-4; Grimsley et al. (1987) *Nature* 325:1677-

9; Boulton et al. (1989) *Plant Mol. Biol.* 12:31-40; and Gould et al. (1991) *Plant Physiol.* 95:426-34.

The genetic manipulations of a recombinant host herein may be performed using standard genetic techniques and screening, and may be carried out in any host cell that is suitable to genetic manipulation. In some embodiments, a recombinant host cell may be any organism or microorganism host suitable for genetic modification and/or recombinant gene expression. In some embodiments, a recombinant host may be a plant. Standard recombinant DNA and molecular cloning techniques used here are well-known in the art and are described in, for example and without limitation: Sambrook et al. (1989), supra; Silhavy et al. (1984) *Experiments with Gene Fusions*, Cold Spring Harbor Laboratory Press, Cold Spring Harbor, NY; and Ausubel et al. (1987) Current *Protocols in Molecular Biology*, Greene Publishing Assoc. and Wiley-Interscience, New York, NY.

Following the introduction of a nucleic acid into a plant cell, the plant cell may be grown, and upon emergence of differentiating tissue such as shoots and roots, mature plants can be generated. In some embodiments, a plurality of plants can be generated. Methodologies for regenerating plants are known to those of ordinary skill in the art and can be found, for example, in: *Plant Cell and Tissue Culture* (Vasil and Thorpe, Eds.), Kluwer Academic Publishers, 1994. Genetically modified plants described herein may be cultured in a fermentation medium or grown in a suitable medium such as soil. In some embodiments, a suitable growth medium for higher plants may be any growth medium for plants, including, for example and without limitation; soil, sand, any other particulate media that support root growth (e.g., vermiculite, perlite, etc.) or hydroponic culture, as well as suitable light, water and nutritional supplements that facilitate the growth of the higher plant.

Transformed plant cells which are produced by any of the above transformation techniques can be cultured to regenerate a whole plant that possesses the transformed genotype, and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al. (1983) "Protoplasts Isolation and Culture," in *Handbook of Plant Cell Culture*, Macmillian Publishing Company, New York, pp. 124-176; and Binding (1985) *Regeneration of Plants, Plant Protoplasts*, CRC Press, Boca Raton, pp. 21-73. Regeneration can also be performed from plant callus, explants, organs, pollens, embryos or parts thereof. Such regeneration techniques are described generally in Klee et al. (1987) *Ann. Rev. Plant Phys.* 38:467-86.

In other embodiments, the plant cells which are transformed are not capable of regeneration to produce a plant. Such cells may be employed, for example, in developing a plant cell line having a relevant phenotype, for example, herbicide resistance and/or male sterility.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, or gfp genes) that may be present on the recombinant nucleic acid constructs. Such selection and screening methodologies are well known to those skilled in the art.

A transgenic plant containing a heterologous molecule herein can be produced through selective breeding, for example, by sexually crossing a first parental plant comprising the molecule, and a second parental plant, thereby producing a plurality of first progeny plants. A first progeny plant may then be selected that is resistant to a selectable marker (e.g., glyphosate, resistance to which may be conferred upon the progeny plant by the heterologous molecule herein). The first progeny plant may then by selfed, thereby producing a plurality of second progeny plants. Then, a second progeny plant may be selected that is resistant to the selectable marker. These steps can further include the back-crossing of the first progeny plant or the second progeny plant to the second parental plant or a third parental plant.

It is also to be understood that two different transgenic plants can also be mated to produce offspring that contain two independently segregating, added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

A nucleic acid may also be introduced into a predetermined area of the plant genome through homologous recombination. Methods to stably integrate a polynucleotide sequence within a specific chromosomal site of a plant cell via homologous recombination have been described within the art. For instance, site specific integration as described in US Patent Application Publication No. 2009/0111188 A1 involves the use of recombinases or integrases to mediate the introduction of a donor polynucleotide sequence into a chromosomal target. In addition, PCT International Patent Publication No. WO 2008/021207 describes zinc finger mediated-homologous recombination to stably integrate one or more donor polynucleotide sequences within specific locations of the genome. The use of recombinases such as FLP/FRT as described in U.S. Pat. No. 6,720,475, or CRE/LOX as described in U.S. Pat. No. 5,658,772, can be utilized to stably integrate a polynucleotide sequence into a specific chromosomal site. Finally, the use of meganucleases for targeting donor polynucleotides into a specific chromosomal location is described in Puchta et al. (1996) *Proc. Natl. Acad. Sci. USA* 93:5055-60.

Other various methods for site specific integration within plant cells are generally known and applicable. Kumar et al. (2001) *Trends Plant Sci.* 6 (4): 155-9. Furthermore, site-specific recombination systems that have been identified in several prokaryotic and lower eukaryotic organisms may be applied for use in plants. Examples of such systems include, but are not limited too; the R/RS recombinase system from the pSR1 plasmid of the yeast *Zygosaccharomyces rouxii* (Araki et al. (1985) *J. Mol. Biol.* 182:191-203), and the Gin/gix system of phage Mu (Maeser and Kahlmann (1991) *Mol. Gen. Genet.* 230:170-6).

Various assays can be employed in connection with the nucleic acid molecule of certain embodiments herein. In addition to phenotypic observations, the following techniques are useful in detecting the presence of a nucleic acid molecule in a plant cell. For example, the presence of the molecule can be determined by using a primer or probe of the sequence, an ELISA assay to detect an encoded protein, a Western blot to detect the protein, or a Northern or Southern blot to detect RNA or DNA. Additional techniques, such as in situ hybridization, enzyme staining, and immunostaining, also may be used to detect the presence or expression of a recombinant construct in specific plant organs and tissues.

Southern analysis is a commonly used detection method, wherein DNA is cut with restriction endonucleases and fractionated on an agarose gel to separate the DNA by molecular weight and then transferring to nylon membranes. It is then hybridized with the probe fragment which was radioactively labeled with $^{32}$P (or other probe labels) and washed in an SDS solution.

Likewise, Northern analysis deploys a similar protocol, wherein RNA is cut with restriction endonucleases and fractionated on an agarose gel to separate the RNA by molecular weight and then transferring to nylon membranes. It is then hybridized with the probe fragment which was radioactively labeled with $^{32}$P (or other probe labels) and washed in an SDS solution. Analysis of the RNA (e.g., mRNA) isolated from the tissues of interest can indicate relative expression levels. Typically, if the mRNA is present or the amount of mRNA has increased, it can be assumed that the corresponding transgene is being expressed. Northern analysis, or other mRNA analytical protocols, can be used to determine expression levels of an introduced transgene or native gene.

Nucleic acids herein, or segments thereof, may be used to design primers for PCR amplification. In performing PCR amplification, a certain degree of mismatch can be tolerated between primer and template. Mutations, insertions, and deletions can be produced in a given primer by methods known to an ordinarily skilled artisan.

Hydrolysis probe assay, otherwise known as TAQMAN® (Life Technologies, Foster City, Calif.), is another method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

VI. Plants

Some embodiments herein provide transgenic plants comprising at least one nucleic acid comprising a target site for at least one sRNA molecule, such as may be regenerated from stably transformed plant cells or tissues, or may be produced by introgression of such a nucleic acid from a donor line. Such plants may be used or cultivated in any manner, wherein presence of the transforming polynucleotide(s) of interest is desirable. Accordingly, transgenic plants may be engineered to, inter alia, have one or more desired traits (e.g., male sterility), by transformation, and then may be cropped and cultivated by any method known to those of skill in the art. Particular embodiments herein provide parts, cells, and/or tissues of such transgenic plants. Plant parts, without limitation, include seed, endosperm, ovule and pollen. In some embodiments, the plant part is a seed.

Representative, non-limiting example plants include *Arabidopsis*; field crops (e.g., alfalfa, barley, bean, clover, corn, cotton, flax, lentils, maize, pea, rape/canola, rice, rye, safflower, sorghum, soybean, sunflower, tobacco, and wheat); vegetable crops (e.g., asparagus, beet, *Brassica*, broccoli, Brussels sprouts, cabbage, carrot, cauliflower, celery, cucumber (cucurbits), eggplant, lettuce, mustard, onion, pepper, potato, pumpkin, radish, spinach, squash, taro, tomato, and zucchini); fruit and nut crops (e.g., almond, apple, apricot, banana, blackberry, blueberry, cacao, cassava, cherry, citrus, coconut, cranberry, date, hazelnut, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut, and watermelon); tree woods and ornamentals (e.g., alder, ash, aspen, azalea, birch, boxwood, camellia, carnation, chrysanthemum, elm, fir, ivy, jasmine, juniper, oak, palm, poplar, pine, redwood, rhododendron, rose, and rubber).

To confirm the presence of a transforming polynucleotide(s) of interest in a regenerating plant, a variety of assays may be performed. Such assays include, for example and without limitation: biochemical assays, such as detecting the presence of a protein product, e.g., by immunological means (ELISA and/or Western blots) or by enzymatic function; plant part assays (e.g., leaf or root assays); and analysis of the phenotype of the plant.

There are numerous steps in the development of any novel, desirable plant germplasm, which may begin with the generation of a transgenic crop plant. In some embodiments, a transgenic plant comprising at least one nucleic acid comprising a target site for at least one sRNA molecule (e.g., a male sterile plant) may be used in a plant breeding and/or germplasm development program.

Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety an improved combination of desirable traits from the parental germplasm. These important traits may include higher seed yield, resistance to diseases and insects, better stems and roots, tolerance to drought and heat, and better agronomic quality.

The choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three or more years. The best lines are candidates for new commercial cultivars; those still deficient in a few traits may be used as parents to produce new populations for further selection.

These processes, which lead to the final step of marketing and distribution, usually take from eight to twelve years from the time the first cross is made. Therefore, development of new cultivars is a time-consuming process that requires precise forward planning, efficient use of resources, and a minimum of changes in direction.

Pedigree breeding and recurrent selection breeding methods are used to develop cultivars from breeding populations. Breeding programs combine desirable traits from two or more cultivars or various broad-based sources into breeding pools from which cultivars are developed by selfing and selection of desired phenotypes. The new cultivars are evaluated to determine which have commercial potential.

Pedigree breeding is used commonly for the improvement of self-pollinating crops. Two parents which possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In embodiments herein, a transgene comprising a target site for at least one sRNA molecule may be introduced into a plant germplasm, for example, to develop novel inbred lines that are characterized by the tissue-specific expression of the transgene, under the control of the sRNA molecule. A particular advantage of such a development program may be that the generality of the RNAi pathway results in a higher penetrance of the transgenic phenotype than would otherwise be attainable, for example, by other control mechanisms. In certain embodiments, a herbicide tolerance gene that comprises a target site for an sRNA molecule is introduced into a plant germplasm, such that the trait of male sterility is stably inherited and accomplishes hybrid production with a minimal expenditure of valuable resources.

The following examples are provided to illustrate certain particular features and/or embodiments. The examples should not be construed to limit the disclosure to the particular features or embodiments exemplified.

Examples

Example 1: Tissue-specific miRNAs

Many plant miRNAs have a distinct developmental and tissue-specific expression pattern. For example, *Arabidopsis thaliana* miR171 (previously known as miR39) accumulates predominantly in inflorescence tissues. miR171 is produced from an intergenic region in chromosome III and functionally interacts with mRNA targets encoding several members of the Scarecrow-like (SCL) family of putative transcription factors. Llave et al. (2002) Science 297:2053-6. The interaction results in tissue-specific cleavage of target mRNAs within the region of complementarity between miR171 and a native gene mRNA. Transgene mRNAs carrying the target site sequence are also recognized and cleaved.

Similarly, *Zea mays* (maize) miR156 (SEQ ID NO:1) and miR529 (SEQ ID NO:2) are expressed in a developmental and tissue-specific manner. Chuck et al. (2010) Development 137:1243-50; Zhang et al. (2009) *PloS Genetics* November 5. miR156 is temporally regulated, being expressed mainly during the early vegetative stage, but barely detectable during the reproductive stage. In contrast, miR529 is not detected during the vegetative stage, but can be detected in roots and during the reproductive stage in reproductive tissues. Zhang et al. (2009), supra. miR156 and miR529 share a 14 to 16 nucleotide homology, and both target the tasselsheath4 (referred to herein as tsh4) mRNA. tsh4 regulates bract development and the establishment of meristem boundaries in maize. Chuck et. al. (2010), supra.

miRNA microarray in various maize tissues: Tissues from maize inbred line B104 were used for miRNA profiling. Leaf tissues (at V2, V8 and flag leaf stages); immature tassel tissues (0.5 to 2.5 cm length); mature tassel tissues (tassel visible in the whorl); immature ear tissues (0.5 to 2 cm length); and mature ear tissues (visible ear shoot) were collected and immediately submerged in liquid nitrogen and stored at −80° C. Total RNA and low molecular weight RNAs were extracted using a mirVana™ miRNA isolation kit (INVITROGEN; Carlsbad, CA) following the manufacturer's instructions. RNA quality and quantity were assessed by optical density with a NANODROP 2000 spectrophotometer (THERMO SCIENTIFIC; Wilmington, DE) and by gel electrophoresis. miRNA microarray was performed by a commercial provider (LC SCIENCES; Houston, TX) using μParaflo® microfluidic oligonucleotide microarray technology. Zhou et al., (2012) *Methods Mol. Biol.* 822:153-82. All unique plant miRNA sequences available in MiRBase™ (mirbase.org) were printed on the arrays and used for miRNA profiling.

Data regarding miRNA expression of miR156, miR529, and miR319 (SEQ ID NO: 3) are shown in Table 1. The data demonstrate that miR529 is expressed at high levels in the immature tassel, with medium expression in the mature ear and mature tassel, and very low expression in leaves and immature ear, whereas miR156 is expressed at high or medium levels in all tissues examined except the immature ear and immature tassel. Given the preferential expression of miR529 in tassel and ear tissues, an miR529 recognition site was selected to exemplify tissue-specific engineering.

TABLE 1

| miRNA microarray expression profiling of miR529, miR156, and miR319 in maize tissues. Numbers represent relative expression levels. | | | |
|---|---|---|---|
| Tissue | miR529 | miR156 | miR319 |
| Leaf V2 | 199 | 4648 | 13 |
| Leaf V8 | 34 | 1337 | 8 |
| Flag Leaf | 30 | 1657 | 16 |
| Immature Ear | 90 | 112 | 3905 |
| Immature Tassel | 3174 | 78 | 2078 |
| Mature Ear | 1405 | 1595 | 4616 |
| Mature Tassel | 1512 | 2810 | 1566 |

Example 2: Plant Transformation Vectors

In order to investigate whether endogenous sRNA molecules can be used to confer male sterility, the following nucleic acid constructs were engineered and produced.

Transient Transformation Constructs: pDAB112375 (ZmUbilv2/AAD1 v3/native WT miR529-156 site/ZmPer5 3'UTR); pDAB112376 (ZmUbilv2/AAD1 v3/WT miR529 target site with miR156 site mutated/ZmPer5 3'UTR); pDAB112377 (ZmUbilv2/AAD1 v3/miR529 perfect target site with miR156 site mutated/ZmPer5 3'UTR); and pDAB113016 (ZmUbilv2/AAD1 v3/ZmPer5 3'UTR) (non miRNA target control).

Stable Transformation Constructs (All constructs contain ZmPer5 3'UTR/OsAct1 v2/PATv9/Zm Lip 3'UTR within T-DNA): pDAB113018 (ZmUbilv2/AAD1 v3/native WT miR529-156 site/ZmPer5 3'UTR); pDAB113019 (ZmUbilv2/AAD1 v3/WT miR529 target site with miR156 site mutated/ZmPer5 3'UTR); pDAB113020 (ZmUbilv2/AAD1 v3/miR529 perfect target site with miR156 site mutated/ZmPer5 3'UTR); and pDAB113021 (ZmUbilv2/AAD1 v3/ZmPer5 3'UTR) (non miRNA target control).

miRNA target sites: The miRNA target site sequences for miR156 and miR529 were obtained from MiRBase™. A native target site within a corn tsh4 gene (Chuck et al. (2010), supra) was used to design target sites for this disclosure. The tsh4 target site designed (SEQ ID NO:4) contains overlapping miR156 and miR529 binding sites at the 3' end of the coding region. Table2A. The majority of tsh4 transcript cleavage (68%) occurs between base pairs 10 and 11 of the predicted microRNA binding site for miR529 (underlined CT bases in the tsh4 sequence in Table 2A, 2B and 2C), whereas 31% occurs near the predicted cleavage site for miR156 (between base pairs 5 and 7 of miR529). Chuck et al. (2010), supra. The native tsh4 target site sequence was engineered, such that the miR156 binding site within the tsh4 sequence was mutated without interfering with the miR529 binding and cleavage site. Table 2A shows the native tsh4 target site with binding sites specific to miR156 or mR529, which was used in the construction of pDAB112375. In Tables 2A, 2B, and 2C, mismatches are shown as a "star" (*) while a dot (.) indicates a "G-U" wobble. Table 2B and Table 2C illustrate the modifications (lower case) made in the tsh4 target site as used in constructs of pDAB112376 and pDAB112377, respectively.

TABLE 2

Sequences of native tsh4 binding site and mutated versions used in maize transformations; pDAB112375 (Table 2A), pDAB112376 (Table 2B), and pDAB112377 (Table 2C). Mismatches are shown as a "star" (*) while a dot (•) indicates a "G-U" wobble.

Sequence Alignments

A.

```
5' GACTCCAGCTGTGCTCTCTCTCTTCTGTCAACTCA 3'    native tsh4 site (SEQ ID NO: 4)
              ||||T*||||||||||||||
         3' CACGAGUGAGAGAAGACAGU 5'          miR156 (SEQ ID NO: 1)
        **|||||•|||||||||||||
      3' UCCGACAUGAGAGAGAGAAGA 5'             miR529 (SEQ ID NO:2)
Native tsh4 sequence showing homology to miR156 and miR529 micro-RNAs.
miR529-directed cleavage site CT is underlined.
```

B.

```
5' GACTCagGCTGTaCTCTCTtaCTTCacaaagtACTCA 3' mutant tsh4 (SEQ ID NO: 7)
             ||*||T*||**||||*|
         3' CACGAGUGAGAGAAGACAGU 5'          miR156 (SEQ ID NO: 1)
             |||||||||**||||*
      3' UCCGACAUGAGAGAGAGAAGA 5'             miR529 (SEQ ID NO: 2)
miR529 homology to tsh4 target sequence improved, preserving the cleavage
site, with miR156 binding site mutated.
```

TABLE 2-continued

Sequences of native tsh4 binding site and mutated versions used in
maize transformations; pDAB112375 (Table 2A), pDAB112376 (Table 2B),
and pDAB112377 (Table 2C). Mismatches are shown as a "star" (*)
while a dot (•) indicates a "G-U" wobble.

Sequence Alignments

C.

```
5' GACTCagGCTGTaCTCTCTctCTTCacaaagtACTCA 3' mutant tsh4 (SEQ ID NO: 8)
        ||*|||*||||||||*****|
      3' CACGAGUGAGAGAAGACAGU 5'          miR156 (SEQ ID NO: 1)
        |||||||||**|||*
    3' UCCGACAUGAGAGAGAGAAGA 5'           miR529 (SEQ ID NO: 2)
miR529 homology to tsh4 target sequence further improved, preserving
the cleavage site, with miR156 binding site mutated.
```

GATEWAY® (INVITROGEN) entry vectors were constructed by standard molecular cloning methods, and were used as expression vectors for transient mRNA expression in maize cells. A starting vector expression cassette (pDAB113016) comprised a sequence (SEQ ID NO: 5) that included an AAD1 v3 coding region followed by a fragment comprising a 3' untranslated region (UTR) from a maize peroxidase 5 gene (ZmPer5 3'UTR v2; U.S. Pat. No. 6,699, 984). AAD1 is a herbicide tolerance gene that encodes aryloxyalknoate dioxygenase (U.S. Pat. No. 7,838,733 herein incorporated by reference in its entirety; Wright et al. (2010) Proc. Natl. Acad. Sci. U.S.A. 107:20240-5), and thus confers tolerance to herbicidal compounds such as Haloxy-fop and Quizalofop. Expression of this coding region in plant cells transformed with DNA of plasmid pDAB113016 (and derivative plasmids below) is under the control of a copy of a maize ubiquitin 1 promoter with associated intron1 (U.S. Pat. No. 5,510,474) and a fragment comprising a 3'UTR from a maize peroxidase 5 gene, as above.

Other entry vector/plant transformation vectors were constructed as derivatives of pDAB113016. For example, pDAB112375 comprises a sequence (SEQ ID NO:6) that includes the AAD1 coding region of pDAB113016, followed by a native tsh4 miR529-156 target site (SEQ ID NO: 4; Table 3) positioned between the end of the AAD1 coding region and the ZmPer5 3'UTR. Plasmid pDAB112376 is a further derivative of pDAB113016, and comprises a sequence (SEQ ID NO: 9) that includes the AAD1 coding region of pDAB113016, followed by a modified tsh4 target sequence comprising a native miR529 binding site, with a mutated miR156 binding site (SEQ ID NO: 7; Table 3) positioned between the end of the AAD1 coding region and the ZmPer5 3'UTR. Further, plasmid pDAB112377 is a derivative of pDAB113016, and comprises a sequence (SEQ ID NO: 10) that includes the AAD1 coding region of pDAB113016, followed by a modified tsh4 target site comprising a native miR529 binding site, with a second version of a mutated miR156 binding site (SEQ ID NO:8; Table 3) positioned between the end of the AAD1 coding region and the ZmPer5 3'UTR.

A further plant transformation plasmid, pDAB112378, was constructed to express an artificial miRNA comprising the miR529 sequence (SEQ ID NO:2). A DNA fragment containing the sequence of miR529 was inserted into a rice miR528 precursor sequence to build artificial miRNA sequence CMSRF9973.1 (SEQ ID NO:11). Production of miRNA CMSRF9973.1 transcripts was under the control of a copy of a maize ubiquitin 1 promoter with intron1, as above, and a fragment comprising a 3'UTR from a maize peroxidase 5 gene, as above.

A negative control plasmid (pDAB112330) comprised a Cry34Ab1 protein coding region (U.S. Pat. No. 8,273,535) under the expression control of a copy of a maize ubiquitin 1 promoter with intron1, as above, and a fragment comprising a 3'UTR from a maize ubiquitin 1 gene (essentially as in GENBANK Accession No. S94464.1).

A further negative control plasmid, pDAB100286, comprised a yellow fluorescent protein (YFP) marker gene coding region (Shagin et al. (2004) Mol. Biol. Evol. 21:841-50) under the expression control of a copy of a maize ubiquitin 1 promoter with intron1, as above, and a fragment comprising a 3'UTR from a maize peroxidase 5 gene, as above.

TABLE 3

Exemplary miRNA target sites.

| SEQ ID NO: 4 | GACTCCAGCTGTGCTCTCTCTCTTCTGTCAACTCA |
| SEQ ID NO: 7 | GACTCAGGCTGTACTCTCTTACTTCACAAAGTACTCA |
| SEQ ID NO: 8 | GACTCAGGCTGTACTCTCTCTCTTCACAAAGTACTCA |

Transformation/expression vectors for Agrobacterium-mediated maize embryo transformation were constructed through the use of standard cloning methods and GATE-WAY® recombination reactions employing a typical destination binary vector (pDAB101849) and entry vectors, as described above. Binary destination vector pDAB101849 comprises a herbicide tolerance gene (phosphinothricin acetyl transferase (PAT); Wehrmann et al. (1996) Nat. Biotechnol. 14:1274-8) under the expression control of a rice actin promoter with associated intron1 and 5'UTR (essentially as disclosed as bases 12 to 1411 of GENBANK Accession No. EU155408.1). A fragment comprising a 3'UTR from a maize lipase gene (ZmLip 3'UTR, U.S. Pat. No. 7,179,902) was used to terminate transcription of the PAT mRNA. The GATEWAY® recombination reaction was used to move the ZmUbi1/AAD-1 v3/ZmPer5 3'UTR expression cassette, with or without miR529 and miR156 target sites, into the destination binary vector, between the T-DNA borders and upstream of the PAT expression cassette.

33

TABLE 4

| miRNA tsh4 target content of binary vectors. | | |
|---|---|---|
| Binary Vector | Entry/WHISKERS Vector | tsh4 Target Sequence |
| pDAB113018 | pDAB112375 | SEQ ID NO: 4 |
| pDAB113019 | pDAB112376 | SEQ ID NO: 7 |
| pDAB113020 | pDAB112377 | SEQ ID NO: 8 |
| pDAB113021 | pDAB113016 | None |

In addition, transformation vector pDAB109812 was constructed through the use of standard GATEWAY® recombination reactions employing a typical binary destination vector (pDAB101847). Binary destination vector pDAB101847 comprises an AAD1 herbicide tolerance coding region (as above) under the expression control of a sugarcane bacilliform virus (SCBV) promoter (SEQ ID NO:12); essentially as described in U.S. Pat. No. 6,093,569. A synthetic 5'UTR sequence (SEQ ID NO:13), comprised of sequences from a Maize Streak Virus (MSV) coat protein gene 5'UTR and intron 6 from a maize Alcohol Dehydrogenase 1 (ADH1) gene, is positioned between the 3' end of the SCBV promoter segment and the start codon of the AAD1 coding region. A fragment comprising a 3'UTR from a maize lipase gene, as above, was used to terminate transcription of the AAD1 mRNA. Transformation vector pDAB109812 was constructed by adding a yellow fluorescent protein marker gene cassette (Phi-YFP™ coding region containing a potato intron ST-LS1 from EVROGEN, Moscow, Russia) to pDAB101847 by standard molecular cloning and GATEWAY® recombination reactions. Expression of Phi-YFP™ in vector pDAB109812 is under the control of a maize ubiquitin 1 promoter with associated intron1, as above, and a maize ZmPer5 3'UTR, as above.

The structures of all plasmids were confirmed by restriction enzyme digests and determinations of the DNA base sequences of relevant regions were confirmed by standard molecular biological techniques.

Example 3: Transient Expression of AAD1

Zea mays embryos from inbred line B104 that express AAD1 mRNAs having miRNA target sites within the mRNA were produced. Control tissues having no miRNA target sites in the AAD1 mRNA, or having no AAD1 gene expression cassette, were also produced. Other control tissues were produced that had only a YFP gene expression cassette (and no AAD1 construct). Preparations of plant transformation DNA molecules constructed as described in EXAMPLE 2 were delivered into maize B104 immature embryos via particle bombardment transformation.

Plasmid DNAs of pDAB112375, pDAB112376, pDAB112377, pDAB113016, pDAB100286, pDAB112378 and pDAB112330 were isolated and purified from Escherichia coli by standard techniques, and diluted in TE buffer (10 mM Tris HCl plus 1 mM EDTA, pH 8) to 1.0 µg/µL.

Gold particles stock preparation: Gold particle stock was prepared by weighing 50 mg of 1 µm gold microcarriers (BIO-RAD LABORATORIES, Richmond, CA) into a sterile 2.0 mL microcentrifuge tube, followed by 3 washes with 100% ethanol and pelleting at 1500 x g for 2 minutes in a microcentrifuge. The particles were then washed 3 times with sterile water as above. Finally, 500 µL sterile 50% glycerol was added to the gold particles in the tube and the suspension was stored at –20° C.

Embryo isolation and culture: (Day 1) Surface-sterilized B104 immature ears (10 to 12 days post-pollination) were used for the isolation of embryos. Excised immature embryos from 3 to 4 ears were pooled into 2 mL microfuge tubes containing 2.0 mL liquid medium (LS basal medium (Linsmaier and Skoog, (1965) Physiologia Plantarum 18:100-27) containing CHU N6 vitamins (Chu et al. (1975) Scientia Sinica 18:659-68), 700 mg/L L-Proline, 68.5 gm/L sucrose, 36 gm/L D(+) glucose, and 1.5 mg/L 2,4-D). After embryo isolation, the liquid medium was removed and discarded. Embryos were removed and placed onto plates (40 embryos per plate) containing a semi-solid osmotic medium (MS basal medium (Murashige and Skoog, (1962) Physiologia Plantarum 15:473-497), 2 mg/L Glycine, 500 µg/L Thiamine, 500 µg/L Pyroxidine, 50 µg/L Nicotinic Acid., 120 gm/L sucrose, 100 mg/L myo-inositol, and 2.4 gm/L GELRITE). The embryos were arranged in a 6×7 grid within the target area for particle bombardment. Three replicate plates were prepared for each construct to be tested. All plates were incubated at 28° C. under continuous low light (50 $\mu Em^{-2}$ $sec^{-1}$) for 24 hours prior to particle bombardment.

Coating gold particles with DNA: (Day 2) Tubes of frozen gold particles glycerol stock were thawed on ice for a few minutes, then vortexed for 2 minutes at high speed until a uniform gold suspension was produced. Gold suspension was pipetted into sterile microcentrifuge tubes (50 µL each), with an intermediate vortexing of the particle stock between each tube to maintain a uniform suspension. 2.5 µg each of appropriate plasmid DNAs were included. Instantaneous mixing of experimental components was accomplished by gently vortexing the microcentrifuge tube while 2.5 µL appropriate DNAs (1 µg/µL), 50 µL ice-cold sterile 2.5 M CaCl$_2$), and 20 µL of sterile 0.1 M spermidine were added (in that order). The tubes were then vortexed at high speed at 4° C. for 20 minutes. The gold/DNA particles were then washed 3 times with 100% ethanol and finally suspended in 30 µL 100% ethanol. The tubes were placed on ice and were used within 2 hrs. from the time of preparation.

Preparation of macrocarriers with gold/DNA microcarriers: The following operations were performed in a laminar flow hood. Sterile macrocarriers for the BIOLISTIC PDS-1000/He PARTICLE DELIVERY SYSTEM (BIO-RAD LABORATORIES, Inc.) were placed in sterile Petri dishes. Tubes of gold/DNA microcarriers were vortexed and 5 µL gold/DNA suspension was quickly spread onto the appropriate macrocarrier. Macrocarriers with gold/DNA were allowed to dry for 10 mins. prior to use for particle bombardment.

Particle bombardment transformation: After sterilizing 1100 psi rupture disks by quickly submerging them into 70% isopropanol, a rupture disk was inserted into the disc retaining cap. The macrocarriers and sterile stopping screens were loaded into the launch assembly and placed in the chamber. Each of the plates with arranged embryos was placed on the chamber shelf at 6 cm distance. The chamber was then evacuated to, and held at, 28 mm Hg vacuum, and the "fire" button was held until the rupture disk burst. The vacuum was then released and the target plate was covered and sealed with 3M™ Micropore™ medical tape. All plates were then incubated for 24 hrs. under 50 $\mu Em^{-2}$ $sec^{-1}$ continuous light at 28° C.

On Day 3 of the experiment, embryos were removed from the plates in batches of 40 embryos/sampling tube, and sent for protein and molecular analyses.

Example 4: Stable Expression of AAD1

Agrobacterium-mediated transformation was used to stably integrate a chimeric gene into the plant genome, and thus generate transgenic maize cells, tissues, and plants that produce AAD1 mRNAs having miRNA target sites within the mRNA. Control tissues having no miRNA target sites in the AAD1 mRNA were also produced. Transformed tissues were selected by their ability to grow on Haloxyfop-or Bialaphos-containing medium.

*Agrobacterium* Culture Initiation: Glycerol stocks of the project vectors were provided in the *Agrobacterium tumefaciens* host strain DAt13192 (PCT International Patent Publication No. WO2012/016222A2). *Agrobacterium* cultures were streaked from glycerol stocks onto AB minimal medium (Watson, et al. (1975) *J. Bacteriol.* 123:255-64) and incubated at 20° C. in the dark for 3 days containing appropriate antibiotics. The cultures were then streaked onto a plate of YEP medium (g/L: yeast extract, 10; Peptone, 10; NaCl, 5) with antibiotics and incubated at 20° C. in the dark for 1 day.

On the day of an experiment, a mixture of Inoculation Medium and acetosyringone (Frame et al. (2011) *Methods Mol. Biol.* 710:327-41) was prepared in a volume appropriate to the number of constructs in the experiment and pipetted into a sterile, disposable, 250 mL flask. Inoculation Medium contains: 2.2 g/L MS salts; 1× ISU Modified MS Vitamins (Frame et al. (2011), supra) 68.4 g/L sucrose; 36 g/L glucose; 115 mg/L L-proline; and 100 mg/L myo-inositol; at pH 5.4). Acetosyringone was added to the flask containing Inoculation Medium to a final concentration of 200 µM from a 1 M stock solution in 100% dimethyl sulfoxide.

For each construct, 1 or 2 inoculating loop-fulls of *Agrobacterium* from the YEP plate were suspended in 15 mL Inoculation Medium/acetosyringone mixture inside a sterile, disposable, 50 mL centrifuge tube, and the optical density of the solution at 550 nm ($OD_{550}$) was measured in a spectrophotometer. The suspension was then diluted to $OD_{550}$ of 0.3 to 0.4 using additional Inoculation Medium/acetosyringone mixture. The tube of *Agrobacterium* suspension was then placed horizontally on a platform shaker set at about 75 rpm at room temperature, and shaken for 1 to 4 hours before use.

Ear sterilization and embryo isolation: Ears from *Zea mays* cultivar B104 were produced in a greenhouse and harvested 10 to 12 days post pollination. Harvested ears were de-husked and surface-sterilized by immersion in a 20% solution of commercial bleach (ULTRA CLOROX® Germicidal Bleach, 6.15% sodium hypochlorite; with two drops of TWEEN™ 20) for 20 minutes, followed by three rinses in sterile, deionized water inside a laminar flow hood. Immature zygotic embryos (1.8 to 2.2 mm long) were aseptically excised from each ear and distributed into one or more micro-centrifuge tubes containing 2.0 mL *Agrobacterium* suspension into which 2 µL 10% BREAK-THRU® S233 surfactant (EVONIK INDUSTRIES; Essen, Germany) had been added.

*Agrobacterium* co-cultivation: Following isolation, the embryos were placed on a rocker platform for 5 minutes. The contents of the tube were then poured onto a plate of Co-cultivation Medium (4.33 g/L MS salts; 1× ISU Modified MS Vitamins; 30 g/L sucrose; 700 mg/L L-proline; 3.3 mg/L Dicamba in KOH (3,6-dichloro-o-anisic acid or 3,6-dichloro-2-methoxybenzoic acid); 100 mg/L myo-inositol; 100 mg/L Casein Enzymatic Hydrolysate; 15 mg/L AgNO3; 200 µM acetosyringone in DMSO; and 3 g/L agar (SIGMA-ALDRICH, plant cell culture tested) at pH 5.8). The liquid *Agrobacterium* suspension was removed with a sterile, disposable, transfer pipette, and the co-cultivation plate containing the embryos was placed at the back of the laminar flow hood with the lid ajar for 30 minutes, after which time the embryos were oriented with the scutellum facing up using sterile forceps with the aid of a microscope. The plate was returned to the back of the laminar flow hood with the lid ajar for a further 15 minutes. The plate was then closed, sealed with 3M™ Micropore™ medical tape, and placed in an incubator at 25° C. with continuous light at approximately 60 $\mu Em^{-2}$ $sec^{-1}$ light intensity.

Callus Selection and Regeneration of Transgenic Events: Following the co-cultivation period, embryos were transferred to Resting Medium (4.33 g/L MS salts; 1× ISU Modified MS Vitamins; 30 g/L sucrose; 700 mg/L L-proline; 3.3 mg/L Dicamba in KOH; 100 mg/L myo-inositol; 100 mg/L Casein Enzymatic Hydrolysate; 15 mg/L AgNO3; 0.5 g/L MES (2-(N-morpholino) ethanesulfonic acid monohydrate; PHYTOTECHNOLOGIES LABR.; Lenexa, K S); 250 mg/L Cefotaxime; and 7.0 gm/L agar; at pH 5.8). No more than 36 embryos were moved to each plate. The plates were wrapped with Micropore™ tape and incubated at 27° C. with continuous light at approximately 50 $\mu mol$ $m^{-2}s^{-1}$ light intensity for 7 to 10 days. Callused embryos (<18/plate) were then transferred onto Selection Medium I, which is comprised of Resting Medium (above), but with only 6.5 g/L agar, and with either 100 nM R-Haloxyfop acid (0.0362 mg/L; for selection of transformants harboring the AAD1 gene) or 5.0 mg/L Bialaphos (for selection of transformants harboring the PAT gene), as appropriate. Bialaphos was provided as Herbiace® (20% ai). The plates were wrapped with Micropore™ tape and incubated at 27° C. with continuous light at approximately 50 $\mu Em^{-2}$ $sec^{-1}$ light intensity for 7 days. Callused embryos (<12/plate) were then transferred to Selection Medium II, which is comprised of Resting Medium (above) but with only 6.5 g/L agar, and with either 50 nM R-Haloxyfop acid (0.0181 mg/L) or 5.0 mg/L Bialaphos, as appropriate. The plates were wrapped and incubated at 27° C. with continuous light at approximately 50 $\mu Em^{-2}$ $sec^{-1}$ light intensity for 14 days.

At this stage resistant calli (<9/plate) were moved to Pre-Regeneration Medium (4.33 g/L MS salts; 1× ISU Modified MS Vitamins; 45 g/L sucrose; 350 mg/L L-proline; 100 mg/L myo-inositol; 50 mg/L Casein Enzymatic Hydrolysate; 1.0 mg/L AgNO3; 0.5 g/L MES; 0.5 mg/L naphthaleneacetic acid in NaOH; 2.5 mg/L abscisic acid in ethanol; 1 mg/L 6-benzylaminopurine; 250 mg/L Cefotaxime; 5.5 g/L agar; and either 50 nM R-Haloxyfop acid or 3.0 mg/L Bialaphos, as appropriate; at pH 5.8). The plates were wrapped and incubated at 27° C. with continuous light at approximately 50 $\mu Em^{-2}$ $sec^{-1}$ light intensity for 7 days. Regenerating calli (<6/plate) were then transferred to Regeneration Medium in Phytatrays™ (SIGMA-ALDRICH) and incubated at 28° C. with 16 hours light/8 hours dark per day at approximately 150 $\mu mol$ $m^{-2}s^{-1}$ light intensity for 14 days or until shoots developed. Regeneration Medium contains 4.33 g/L MS salts; 1× ISU Modified MS Vitamins; 60 g/L sucrose; 0.50 g/L MES; 125 mg/L Cefotaxime; 5.5 g/L agar; and either 50 nM R-Haloxyfop acid or 3.0 mg/L Bialaphos, as appropriate; at pH 5.8. Small shoots with primary roots were then isolated and transferred to Elongation Medium without selection (i.e., Regeneration Medium without R-Haloxyfop acid or Bialaphos) for further growth. Rooted plantlets about 6 cm or taller were transplanted into soil and moved to a growth chamber for hardening off.

Transfer and establishment of $T_0$ plants in the greenhouse for assay and seed production: Transformed plant tissues selected by their ability to grow on medium containing either Haloxyfop or Bialaphos, as appropriate, were transplanted from Phytatrays™ to small pots (T. O. Plastics, 3.5"

SVD) filled with growing media (PROMIX BX; Premier Tech Horticulture), covered with Humidomes™ (ARCO PLASTICS Ltd.), and then hardened-off in a growth room (28° C. day/24° C. night, 16-hour photoperiod, 50-70% RH, 200 μEm⁻² sec⁻¹ light intensity). When plants reached the V3-V4 stage, they were transplanted into SUNSHINE CUSTOM BLEND 160 soil mixture and grown to flowering in the greenhouse (Light Exposure Type: Photo or Assimilation; High Light Limit: 1200 PAR; 16-hour day length; 27° C. day/24° C. night). Putative transgenic plantlets were analyzed for transgene copy number by quantitative real-time PCR assays using primers designed to detect relative copy numbers of the transgenes, and events selected for advancement were transplanted into 5 gallon pots. Observations were taken periodically to track any abnormal phenotypes.

Plants of the T1 generation were obtained by pollinating the silks of T0 transgenic plants with pollen collected from plants of non-transgenic elite inbred line B104, and planting the resultant seeds. Reciprocal crosses were performed when possible.

Example 5: Biochemical and Molecular Analyses of Transgenic Maize Tissues

ELISA quantification of AAD1 and PAT proteins: Enzyme Linked Immunosorbant Assays (ELISAs) were used to measure the production of AAD1 and PAT proteins in maize cells and stably-transformed tissues. AAD1 and PAT proteins were quantified using kits from ACADIA BIOSCIENCES (Portland, ME) and ENVIROLOGIX (Portland, ME), respectively. The ELISAs were performed using multiple dilutions of plant extracts and using the reagents and instructions essentially as provided by the suppliers.

Plant protein extraction: Proteins were extracted from 4 leaf discs (totaling 1.3 cm²) or 40 immature embryos (for transient expression studies) in 0.6 mL of PBST (PBS buffer containing 0.05% TWEEN® 20) containing either 0.5% BSA (for AAD1 extraction) or 1% PVP-40 (PolyVinylPyrrolidone; for PAT). A 2 mm steel bead was added, the tubes were capped and secured in a GENO/GRINDER (CERTIPREP; Metuchen, NJ), and shaken for 5 minutes at 1500 rpm. Tubes were centrifuged at 4000 rpm for 7 minutes at 4° C., and supernatants containing the soluble proteins were stored at −80° C. until used.

Protein extraction from tassels was performed by grinding 0.5 mL tassel tissue in a GENO/GRINDER at 1500 rpm for 2 minutes using garnet powder, one ceramic sphere (0.25 inch diameter; MP BIOCHEMICALS, Santa Anna, CA) and 1 mL of PBS containing 5 mM EDTA, 5 mM DTT, 10 μL Protease Inhibitor Cocktail VI for plant cell research (Research Products International Corp., Mt. Prospect, IL) and 0.4% TWEEN® 20.

Total protein concentrations were determined using a PIERCE 660 nm Protein Assay kit (THERMO SCIENTIFIC; Rockford, IL) following the supplier's instructions.

Hydrolysis Probe qPCR for copy number analysis: Various types of molecular analyses were employed to screen for low copy, simple events. Leaf tissue was collected from rooted putative transgenic plants before transplanting to soil. DNA was extracted with a QIAGEN MagAttract™ kit using THERMO FISHER KingFisher™ magnetic particle processors and the supplier's recommended protocols. Integrated transgene copy number analysis was performed using specific Hydrolysis Probe assays for the AAD1 and PAT genes. In addition, contamination by inadvertent integration of the binary vector plasmid backbone was detected by a Hydrolysis Probe assay specific for the Spectinomycin resistance gene (Spec) borne on the binary vector backbone. Hydrolysis Probe assays for endogenous maize genes Invertase; (GenBank™ Accession No. U16123; SEQ ID NO:14) and Elongation Factor 1α (EF1α) (GENBANK Accession No. AF136823.1; SEQ ID NO: 15) were developed as internal reference standards. Table 5 lists the oligonucleotide sequences of the Hydrolysis Probe assay components (synthesized by INTEGRATED DNA TECHNOLOGIES, Coralville, IA). Biplex Hydrolysis Probe PCR reactions were set up according to Table 6 with about 10 ng DNA, and assay conditions are presented in Table 7.

TABLE 5

List of forward and reverse nucleotide primers and fluorescent probes used for transgene copy number and relative expression detection.

| Gene Detected | Oligonucleotide | Sequence |
|---|---|---|
| AAD1 | AAD1F | TGTTCGGTTCCCTCTACCAA (SEQ ID NO: 16) |
| | AAD1R | CAACATCCATCACCTTGACTGA (SEQ ID NO: 17) |
| | AAD1P (FAM* Probe) | CACAGAACCGTCGCTTCAGCAACA (SEQ ID NO: 18) |
| PAT | PAT_F | ACAAGAGTGGATTGATGATCTAGAGAGGT (SEQ ID NO: 19) |
| | PAT_R | CTTTGATGCCTATGTGACACGTAAACAGT (SEQ ID NO: 20) |
| | PAT_FamP (FAM Probe) | GGTGTTGTGGCTGGTATTGCTTACGCTGG (SEQ ID NO: 21) |
| Spec | SPC1A | CTTAGCTGGATAACGCCAC (SEQ ID NO: 22) |
| | SPC1S | GACCGTAAGGCTTGATGAA (SEQ ID NO: 23) |
| | TQSPC (FAM Probe) | CGAGATTCTCCGCGCTGTAGA (SEQ ID NO: 24) |
| Maize Invertase | InvertaseF | TGGCGGACGACGACTTGT (SEQ ID NO: 25) |
| | InvertaseR | AAAGTTTGGAGGCTGCCGT (SEQ ID NO: 26) |
| | InvertaseP (HEX* Probe) | CGAGCAGACCGCCGTGTACTT (SEQ ID NO: 27) |

TABLE 5-continued

List of forward and reverse nucleotide primers and
fluorescent probes used for transgene copy number
and relative expression detection.

| Gene Detected | Oligonucleotide | Sequence |
|---|---|---|
| Maize Elongation Factor 1α (EF1α) | EF1a_F EF1a_R EF1a-MGB* (VIC® Probe) | ATAACGTGCCTTGGAGTATTTGG (SEQ ID NO: 28) TGGAGTGAAGCAGATGATTTGC (SEQ ID NO: 29) TTGCATCCATCTTGTTGC (SEQ ID NO: 30) |

*FAM = 6-Carboxy Fluorescein Amidite; HEX = Hexachlorofluorescein

TABLE 6

Hydrolysis Probe PCR Mixture for
Transgene DNA Copy Number
Analysis.

| Reaction Component | μL | Final Concentration |
|---|---|---|
| Water | 0.5 | |
| PVP (10%) | 0.1 | 0.1% |
| ROCHE 2X Master Mix | 5 | 1X |
| Transgene Forward Primer (10 μM) | 0.4 | 0.4 μM |
| Transgene Reverse Primer (10 μM) | 0.4 | 0.4 μM |
| Transgene Probe (5 μM) | 0.4 | 0.2 μM |
| Invertase Forward Primer (10 μM) | 0.4 | 0.4 μM |
| Invertase Reverse Primer (10 μM) | 0.4 | 0.4 μM |
| Invertase Probe (5 μM) | 0.4 | 0.2 μM |

TABLE 7

Thermocycler Conditions for
Hydrolysis Probe PCR Amplification.

| PCR Steps | Temp (° C.) | Time | No. cycles |
|---|---|---|---|
| Denature/Activation | 95 | 10 min | 1 |
| Denature | 95 | 10 sec | 40 |
| Anneal/Extend | 58 | 35 sec | |
| Acquire | 72 | 1 sec | |
| Cool | 40 | 10 sec | 1 |

For amplification, LIGHTCYCLER®480 Probes Master mix (ROCHE APPLIED SCIENCE, Indianapolis, IN) was prepared at 1× final concentration in a 10 μL volume multiplex reaction containing 0.1% PVP, 0.4 μM of each primer, and 0.2 μM of each probe. The FAM (6-Carboxy Fluorescein Amidite) fluorescent moiety was excited at 465 nm, and fluorescence was measured at 510 nm. The corresponding values for the HEX (hexachlorofluorescein) fluorescent moiety were 533 nm and 580 nm, and for VIC® the values were 538 nm and 554 nm. The level of fluorescence generated for each reaction was analyzed using the ROCHE LIGHTCYCLER®480 Real-Time PCR system according to the manufacturer's recommendations. Transgene copy number was determined by comparison of LIGHTCY-CLER®480 outputs of Target/Reference gene values for unknown samples to Target/Reference gene values of known copy number standards (1-Copy representing hemizygous plants, 2-Copy representing homozygous plants).

Cp scores; i.e., the point at which the florescence signal crosses the background threshold using the fit points algorithm (LIGHTCYCLER® software release 1.5), and the Relative Quant module (based on the ΔΔCt method), were used to perform the analysis of real time PCR data.

In the LIGHTCYCLER® Fit Points Algorithm software, a graph of the data was made by plotting the logarithm of the input DNA template concentration against the measured Cp values. The slope of the curve is a desired comparison parameter; therefore the initial log input number can be an arbitrary starting point on the curve, with the caveat that the arbitrary concentration values used for input DNA template are representative of the actual serial dilution used. For example, for a 10-fold serial dilution series, the actual inputs concentrations may be 1000, 100, 10, etc., for which points the LC480 Fit Points Algorithm software plots 3, 2, 1, etc. as the logarithms of the inputs. Using a linear regression, the resulting best fit of this line (input log vs Cp) was then used to estimate a slope (m) from an equation of the form y=mx+b. There is an inverse relationship between the starting template amount and Cp value, and therefore the slope (m) is always negative.

A perfect (i.e., 100% efficient) PCR reaction doubles the total template every cycle. PCR efficiency (Eff) is calculated as:

$$Eff = 10e^{(-1/m)}$$

Thus, the slope (m) of the graph of log input vs Cp will be −3.3219 for a perfectly efficient reaction (whose efficiency is defined as 2.00).

In other words, a 100% efficient PCR reaction is defined by:

$$2.0 = 10e^{(-1/-3.3219)}$$

The LC480 Fit Points Algorithm software reports the efficiency value by the first formula. So a 99% efficient reaction has an Eff value of 1.99, rather than 0.99.

To express this as a percent efficiency, subtract 1 from this value and multiply by 100. Or, $$\% \, Eff = [(10e^{(-1/m)}-1)] \times 100$$

AAD1 relative transcript analysis: Quantitative Hydrolysis Probe PCR was also used to detect the relative levels of AAD1 transcript. Leaf and tassel tissues were collected at the VT stage (i.e., immediately prior to pollen shed). Approximately 500 ng total RNA (extracted with a King-Fisher™ total RNA Kit; THERMO FISHER SCIENTIFIC) was used for cDNA synthesis using a high capacity cDNA synthesis kit (INVITROGEN) and random primer T20VN (TTTTTTTTTTTTTTTTTTTVN; SEQ ID NO:31, where V is A, C, or G, and N is A, C, G, or T/U). Typically, a 20 μL reaction contained 2.5 U/μL MultiScribe™ reverse transcriptase, 200 nM T20VN oligonucleotide, and 4 mM dNTPs. The reaction was initiated by incubation for 10 minutes at 25° C., then synthesis was performed for 120 minutes at 37° C. and inactivated by 5 minutes at 85° C.

Newly-synthesized cDNA was used for PCR amplification. Hydrolysis Probe qPCR set up, running conditions, and signal capture were the same as given above for DNA copy number analyses. AAD1 expression data were calculated using 2-ΔΔCt relative to the level of EF1α.

MicroRNA detection: Traditional methods such as Northern blot analysis are not suitable for high throughput screening of small RNAs, in part due to the requirement for a large amount of RNA. This study utilized an innovative approach for detection of mature microRNAs that employed a stem-looped, key-like primer for cDNA synthesis, followed by Hydrolysis Probe PCR analysis (Chen et al. (2005) *Nucleic Acids Res.* 33: e179; Yang et al. (2009) *Plant Biotechnol. J.* 7:621-30; Varkonyi-Gasic et al. (2007) *Plant Methods* 3:12). The key-like RT-PCR primers comprise a universal sequence of 35 nucleotides on the 5' end to create a partially double stranded stem-loop structure, and 8 nucleotides on the 3' end, chosen to be complementary to the specific mature microRNA, and which are used to initiate the reverse transcription reaction. This stem-loop structure introduces a universal reverse PCR primer binding site and a compatible probe from a Universal Probe Library (UPL21, ROCHE DIAGNOSTICS) for downstream PCR amplification, thus alleviating the unique challenge of designing conventional PCR primers to amplify short microRNA sequences.

Total RNA isolated by means of a fully-automated King-Fisher™ extraction method is sufficient for miRNA detection using Hydrolysis Probe PCR amplification, as well as microRNA analysis. All assays included negative controls of no-template (mix only). For the standard curves, a blank (water in source well) was also included in the source plate to check for sample cross-contamination.

For cDNA synthesis, the key-like primer for miR156 and miR529 (Table 8, miR156_RT and miR529_RT) as well as the oligonucleotides for EF1a (EF1α_F and EF1a R; Table 5) were included in the reaction (Table 9) using temperature settings of 10 minutes at 25° C. for pre-incubation, 120 minutes for synthesis at 37° C., and 5 minutes at 85° C. for inactivation. The RT product was then amplified using a microRNA-specific forward primer and the universal reverse primer (Table 8). FAM-labeled UPL21 was used for fluorescent signal generation and amplification of EF1a was used as an endogenous reference mRNA. A LIGHTCYCLER®480 Real-Time PCR system was used for cycling and signal detection. Transcription level was calculated using 2-ΔΔCt relative to EF1α. Data were analyzed using LIGHTCYCLER™ Software v1.5 by relative quantification using a second derivative max algorithm for calculation of Cq values according to the supplier's recommendations. For expression analyses, expression values were calculated using the ΔΔCt method (i.e., 2-(Cq TARGET-Cq REF)), which relies on the comparison of differences of Cq values between two targets, with the base value of 2 being selected under the assumption that, for optimized PCR reactions, the product doubles every cycle.

TABLE 8

Oligonucleotides used for cDNA Synthesis
and miRNA Detection (miR156 and miR529).

| Name | Sequence |
|---|---|
| miR156_RT | GTTGGCTCTGGTGCAGGGTCCGAGGTATTCGCAC CAGAGCCAACGTGCTC (SEQ ID NO: 32) |
| miR529_RT | GTTGGCTCTGGTGCAGGGTCCGAGGTATTCGCAC CAGAGCCAACAGGCTG (SEQ ID NO: 33) |
| miR156_F Forward Primer | GGTGACAGAAGAGAGTGAGCAC (SEQ ID NO: 34) |

TABLE 8-continued

Oligonucleotides used for cDNA Synthesis
and miRNA Detection (miR156 and miR529).

| Name | Sequence |
|---|---|
| miR529_F Forward Primer | GGCGGAGAAGAGAGAGAGTACAG (SEQ ID NO: 35) |
| Universal Reverse Primer | GTGCAGGGTCCGAGGT (SEQ ID NO: 36) |
| UPL21 (FAM*) | TGGCTCTG |

*FAM = 6-Carboxy Fluorescein Amidite

TABLE 9 cDNA Synthesis Mixture for
miR156 and miR529.

| Component | μL | Stock | Final |
|---|---|---|---|
| 10X RT Buffer | 2 | 10X | 1X |
| miR156_RT Primer | 0.5 | 10 μM | 0.25 μM |
| miR529_RT Primer | 0.5 | 10 μM | 0.25 μM |
| EF1a_F Primer | 0.5 | 10 μM | 0.25 μM |
| EF1a_R Primer | 0.5 | 10 μM | 0.25 μM |
| dNTP mix | 0.8 | 100 mM | 4 mM |
| Water | 4.2 | | |
| Multiscribe ™ RT | 1 | 50 U/μL | 2.5 U/μL |
| RNA | 10 | ~50 ng/μL | |
| Total | 20 | | |

TABLE 10

Hydrolysis Probe PCR Mixture for
miRNA Transcript Detection.

| Component | μL | Stock | Final |
|---|---|---|---|
| 2X Roche MasterMix ™ | 5 | 2X | 1X |
| miRNA-Specific Forward Primer | 0.4 | 10 μM | 0.4 |
| Universal Reverse Primer | 0.4 | 10 μM | 0.4 |
| UPL21 | 0.2 | 10 μM | 0.2 |
| EF1a_F Primer | 0.4 | 10 μM | 0.4 |
| EF1a_R Primer | 0.4 | 10 μM | 0.4 |
| EF1α_MGB VIC ® | 0.2 | 10 μM | 0.2 |
| 10% PVP | 0.1 | | |
| cDNA | 2.0 | | |
| Water | 0.9 | | |

Figure 2:
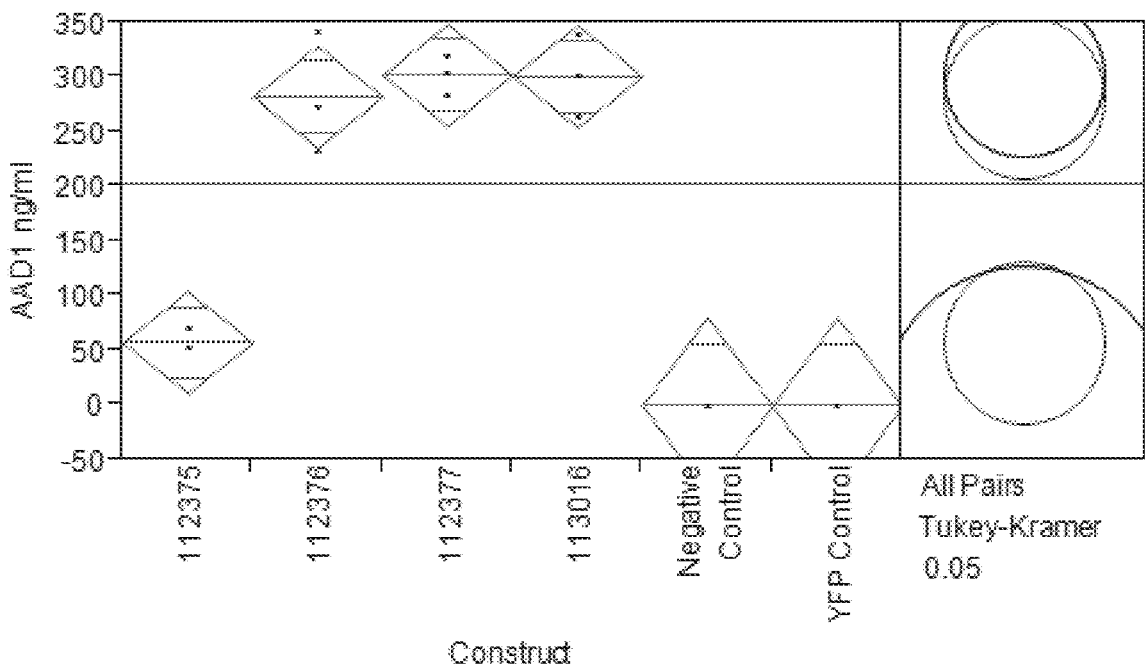
FIG. 2 includes data showing the transient expression of AAD1 in immature corn embryos.
Figure 3A:
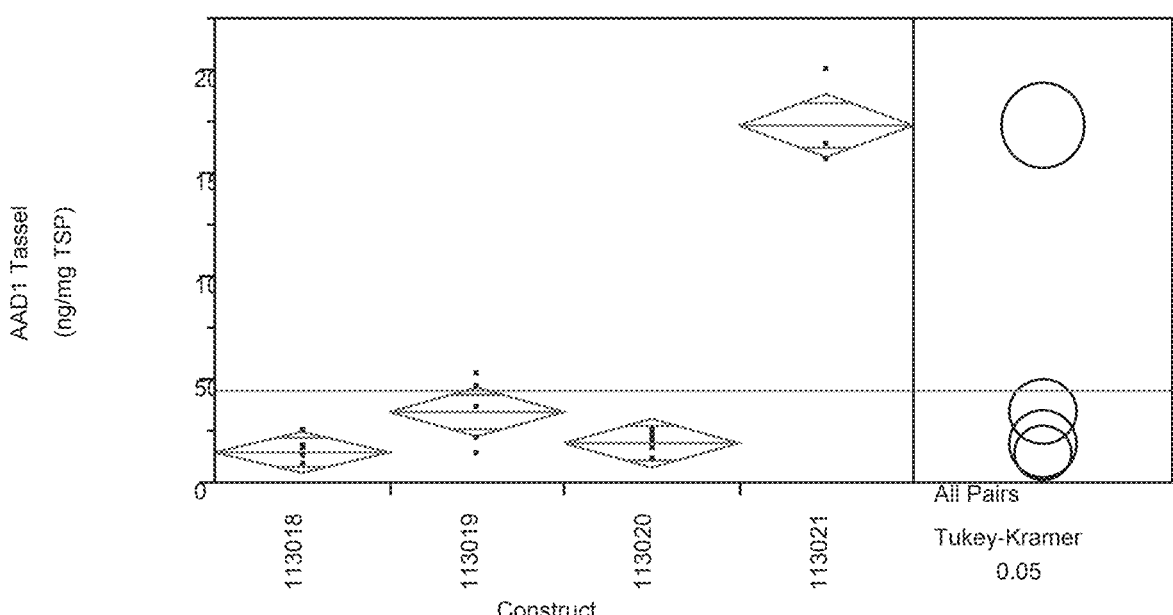
FIGS. 3A and 3B include data showing the expression of AAD1 in tassel.
Figure 3B:
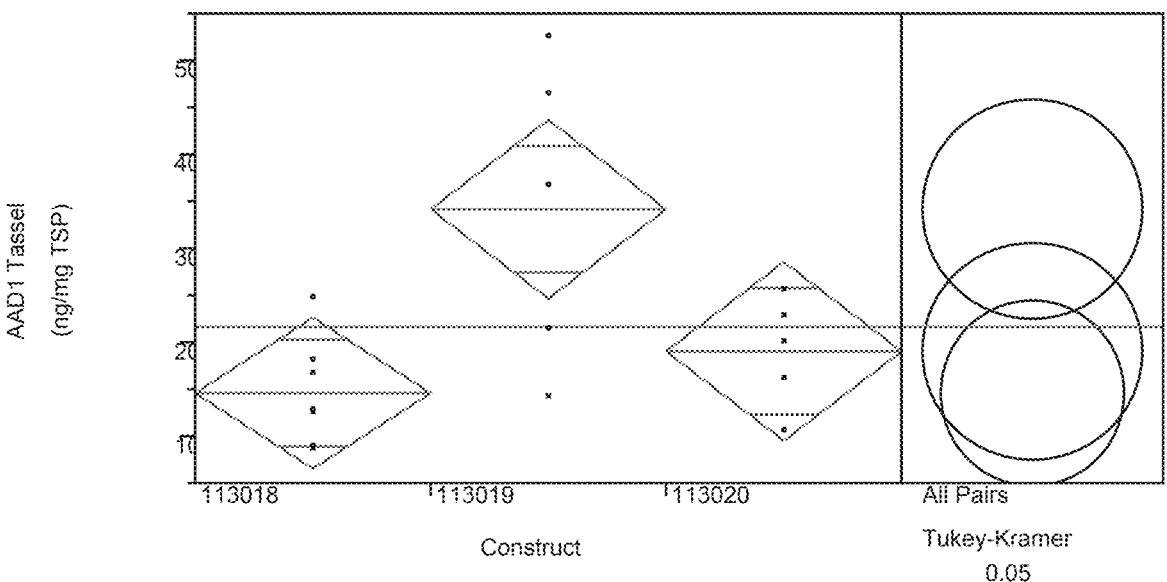
Figure 4A:
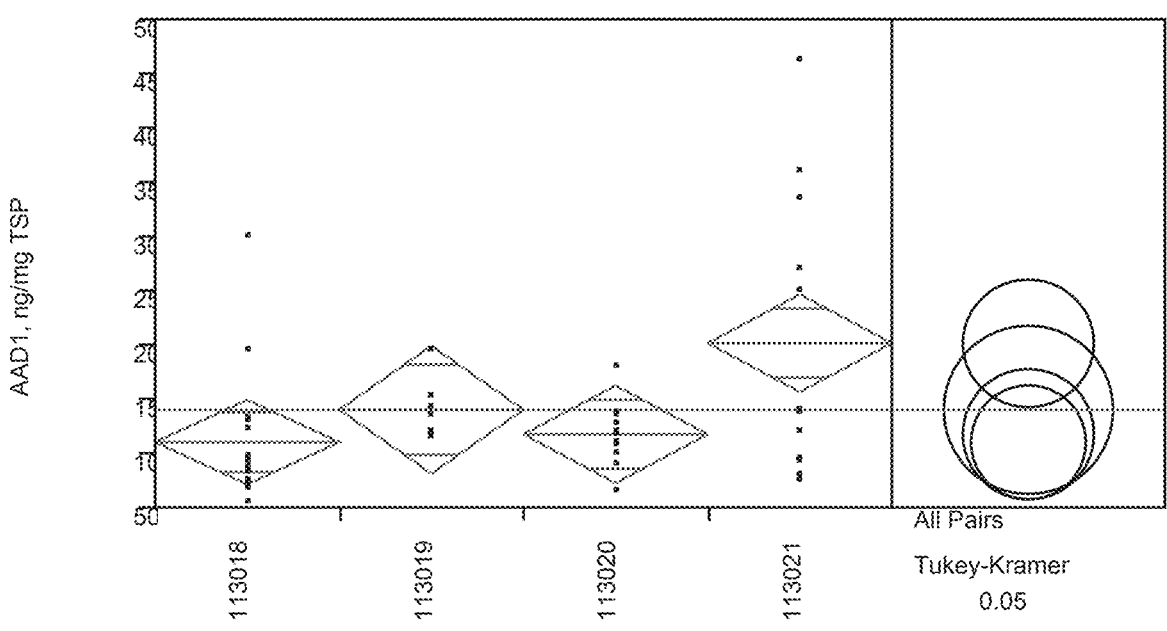
FIGS. 4A and 4B include data showing the expression of AAD1 in leaf.
Figure 4B:
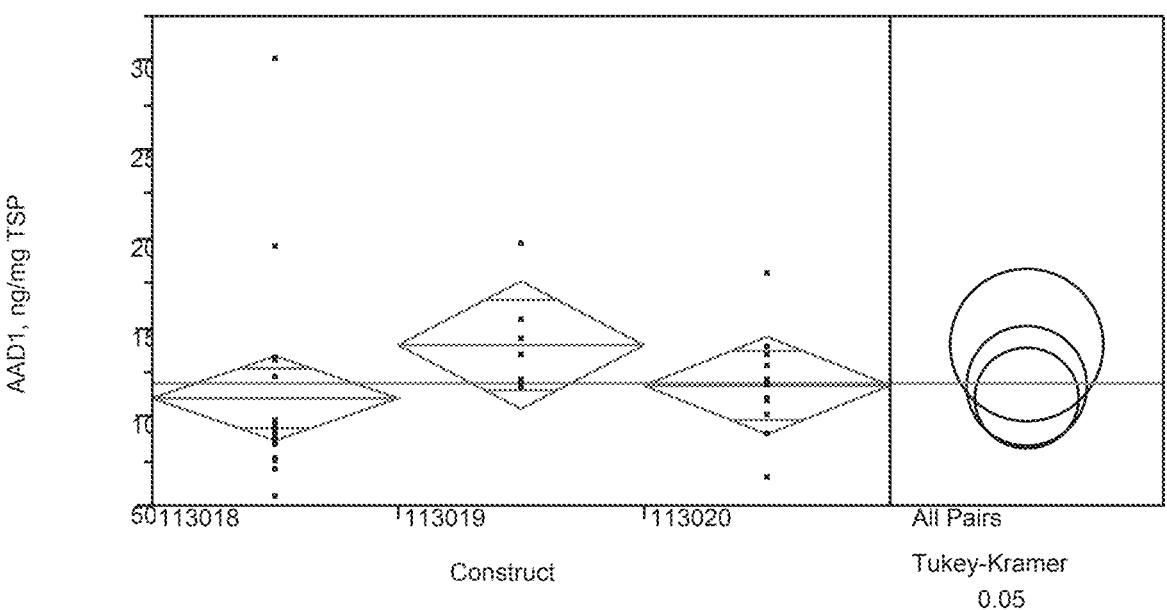
Figure 5A:
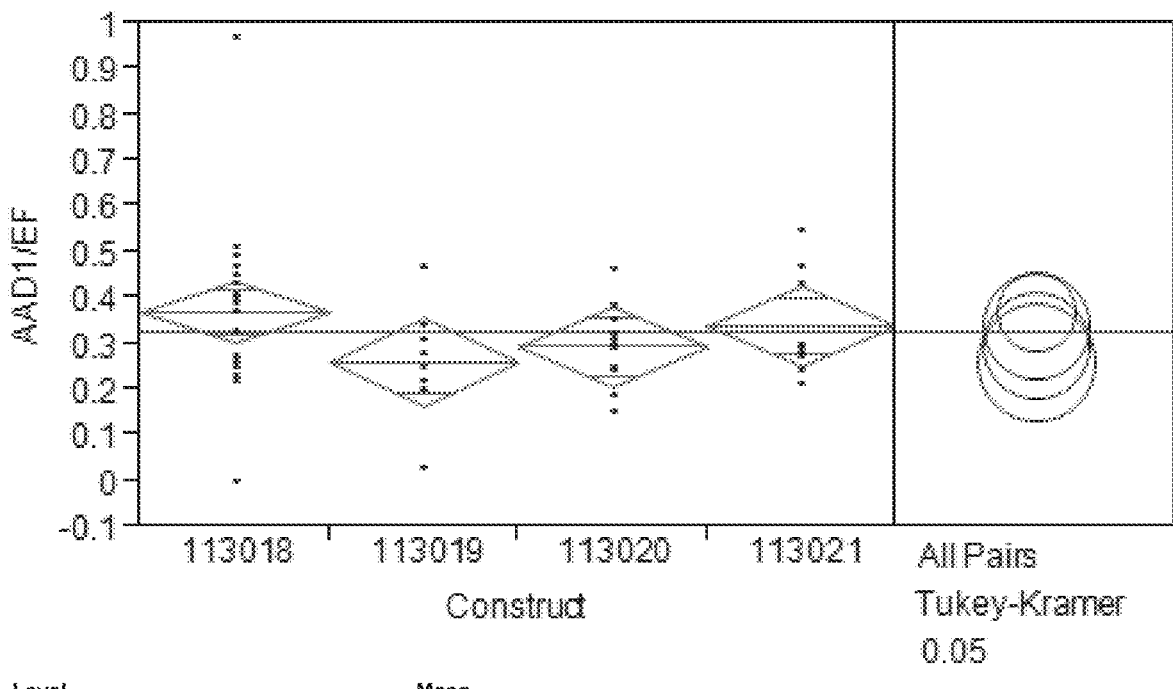
FIGS. 5A and 5B include data showing the expression of AAD1 RNA in leaf (FIG. 5A) and tassel (FIG. 5B).
Figure 5B:
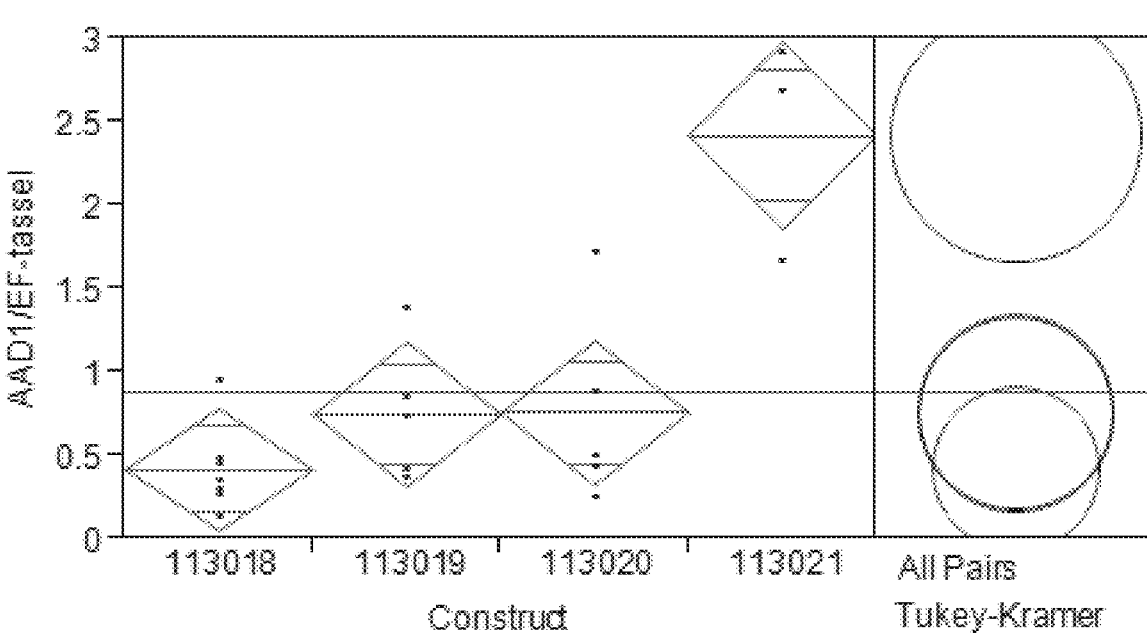

Example 6: tsh4 Target Site-mediated Reduction of AAD1 mRNA and Protein Production Twenty four hours after particle bombardment of immature embryos with plasmid DNAs containing AAD1 constructs or control plasmids as described in EXAMPLE 2, the cells were harvested and the amounts of AAD1 protein produced were determined by ELISA. Table 11 presents AAD1 protein production data that show elevated amounts of AAD1 protein were produced in cells bombarded with plasmids pDAB113016, pDAB112376, and pDAB112377, compared to cells receiving plasmids pDAB112375, pDAB100286, or not bombarded (Negative Control). Production of AAD1 is repressed in cells transformed with pDAB112375 (native tsh4 target site), presumably due to a high abundance of miR156 in corn immature embryos. Cells transformed with plasmids having an AAD1 gene with no miRNA target site (pDAB113016), or with mutated tsh4 target sites (pDAB112377 and pDAB112376), produced higher levels of AAD1 protein. No effect from the artificial miRNA construct harbored by pDAB112378 or from the Cry34Ab control construct harbored by pDAB112330 was observed in any of the treatments. See also FIG. 2.

TABLE 11

AAD1 Protein Levels in Maize Immature Embryos 24 Hours after Particle Bombardment.

| AAD1 Test Plasmid | Co-bombardment plasmid | Mean AAD1 Amount (ng/mL) |
|---|---|---|
| pDAB113016 (no miRNA target site) | pDAB112330 (Cry34Ab) | 302 |
| pDAB113016 (no miRNA target site) | pDAB112378 (artificial miRNA) | 436 |
| pDAB112376 (SEQ ID NO: 9; modified tsh4 target site SEQ ID NO: 7) | pDAB112378 (artificial miRNA) | 317 |
| pDAB112377 (SEQ ID NO: 10; modified tsh4 target site SEQ ID NO: 8) | pDAB112378 (artificial miRNA) | 249 |
| pDAB112375 (SEQ ID NO: 2; native tsh4 target site) | pDAB112378 (artificial miRNA) | 51 |
| pDAB112375 (SEQ ID NO: 2; native tsh4 target site) | pDAB112330 (Cry34Ab) | 58 |
| pDAB100286 (No AAD1; YFP) | None | 0.00 |
| None (Negative Control) | None | 0.00 |

*Agrobacterium*-mediated procedures were used to produce stably-transformed maize immature embryos using plasmids pDAB113018, pDAB113019, pDAB113020, and pDAB113021. Table 4. Plasmid pDAB113018 harbors two selectable marker genes (PAT and AAD1) within the T-DNA borders (EXAMPLE 2). The mRNA produced from the AAD1 transgene in pDAB113018 contains a native tsh4 miR156/miR529 target site sequence. pDAB113018-transformed embryos were randomly split between plates of Selection Medium I containing 100 nM R-Haloxyfop acid (for selection of transformants harboring the AAD1 gene) or 5.0 mg/L Bialaphos (for selection of transformants harboring the PAT gene). All the embryos placed on Haloxyfop-containing medium browned and died, while the embryos on Bialaphos-containing medium grew and regenerated as usual. Transgenic embryos are routinely selected, grow and regenerate on Haloxyfop-containing medium when transformed with an AAD1 gene lacking the tsh4 target site sequence. The immature embryos transformed with plasmids having an AAD1 gene with no miRNA target site (pDAB113016), or with mutated tsh4 target sites for miR156 (pDAB112377 and pDAB112376), produced higher levels of AAD1 protein grew on on Haloxyfop-containing medium and regenerated transgenic plants. Thus, levels of AAD1 protein produced in pDAB113018-transformed cells are insufficient to provide Haloxyfop tolerance. Death of the pDAB113018-transformed embryos on Haloxyfop-containing medium is presumably due to destruction of the AAD1 mRNA in the developing embryos by miR156-mediated mRNA cleavage.

Stable transgenic $T_0$ plants (1 to 2 copies of the transgenes) were transferred to the greenhouse for mature plant production. For each construct, 8 to 12 $T_0$ plants were tested for leaf expression of AAD1 mRNA and protein, and 4 to 6 $T_0$ plants were tested for tassel expression of AAD1 mRNA and protein. AAD1 mRNA levels were calculated relative to the levels of maize Elongation Factor mRNA as described in EXAMPLE 5. Table 12 shows the results of the analyses. See also FIGS. 3A-5B. Examination of the data shows that there is up to a 6-fold reduction of mRNA production and an 11-fold repression of AAD1 protein production in tassel tissues in plants transformed with plasmids expressing AAD1 mRNA containing an miR529 target site (plasmids pDAB113018, pDAB113019, and pDAB113020), when compared to tissues producing AAD1 mRNA with no target site. In leaf tissues, however, there is very little difference in either AAD1 mRNA or protein accumulation between plants transformed with the different plasmids. This result is in line with the data of Table 1, which shows that the level of miR529 is 16- to 100-fold higher in immature tassel tissues than in leaves. Thus, the results summarized in Table 11, and particularly in Table 12, demonstrate that engineering of mRNA to include miRNA target cleavage sites may be used as a mechanism to control tissue-specific accumulation of a specific mRNA and protein.

TABLE 12

Levels of AAD1 mRNA and Protein in Leaves and Tassels of Transgenic B104 Plants. Means were separated using the Tukey-Kramer Test.

| Transforming Plasmid | Leaves | | Tassels | |
|---|---|---|---|---|
| | mRNA Level* | Protein** | mRNA Level* | Protein** |
| pDAB113018 | 0.371 (A)*** | 110.22 (B) | 0.420 (B) | 145.86 (B) |
| pDAB113019 | 0.261 (A) | 140.10 (AB) | 0.752 (B) | 341.54 (B) |
| pDAB113020 | 0.294 (A) | 117.37 (AB) | 0.760 (B) | 190.30 (B) |
| pDAB113021 (no target site) | 0.340 (A) | 201.45 (A) | 2.423 (A) | 1730.50 (A) |

*Relative to maize EF1α mRNA.
**ng AAD1 protein/mg Total Soluble Protein
***Levels not connected by the same letter are significantly different A transgenic maize plant is produced wherein the accumulation of an AAD1 mRNA comprising an miRNA target site is limited by cleavage by miRNA (e.g., miR156, miR529, and miR319) in tissues or cells comprising the immature tassel, including the palea, lemma, stamen, filament, anther, microspores, male gametophyte, sperm cell, tube cell, or other cells that affect or control pollen development. Such limited accumulation of AAD1 mRNA is insufficient to produce a level of AAD1 protein accumulation sufficient to confer tolerance of immature tassel tissues to herbicides that are substrates for AAD1, such as Haloxyfop and Quizalofop. Thus, treatment of such transgenic plants at an immature tassel stage of development with herbicides that are substrates for AAD1 prevents tassel and pollen development, and results in a male sterile plant. Micro RNA expression profiling disclosed in Table 1 shows that miR529 is not specifically expressed in the tassel tissue, but rather is expressed at similar levels in both tassel and ear tissues in later stages of development. Therefore, treatment of transgenic plants (accumulating AAD1 mRNA comprising said miRNA target site) with herbicides that are substrates for AAD1 during an early stage of tassel development prevents tassel and pollen development, thus resulting in male sterility, and without affecting ear tissue development.

Example 7: AAD1 mRNA and protein production in $T_1$ maize plants

Five single copy transgenic events per construct were planted in the greenhouse for T1 expression analysis. For each event; 7 to 8 plants (35-40 plants per construct) were tested for leaf expression of AAD-1 mRNA, and 2 plants (10 plants per construct) were tested for expression of AAD-1 mRNA and protein in different tissues in multiple growth stages. AAD-1 mRNA levels were calculated relative to the levels of maize Elongation Factor mRNA (EF1a transcripts) as described in EXAMPLE 5. The data in Table 13 show that there was no effect of miRNA target sites on AAD1 expression in leaves of V6 plants transformed with constructs pDAB113019 and pDAB113020 compared to the "no miRNA" control plants transformed with pDAB113121. However, a significant decrease in AAD1 mRNA expression was observed in plants transgenic to constructs pDAB113018 that contain native miRNA target site without any mutation. The AAD1 reduction in these plants is potentially due to miR156 that is present in high abundance in the leaf tissue. These results confirm that mutations for the miR156 site made in pDAB113019 and pDAB113020 removed the miR156 binding in these constructs and therefore down regulation of AAD1 was avoided in the leaf tissue.

TABLE 13

Ratio of AAD1 to EF1α mRNA levels in Leaves of $T_1$ Transgenic B104

Plants at the V6 Growth Stage.

Means were separated using the Tukey-Kramer Test.

| Transforming Plasmid | Number of plants sampled | Mean mRNA Ratio |
|---|---|---|
| pDAB113021 | 38 | 2.31 (A)* |
| pDAB113020 | 40 | 2.30 (A) |
| pDAB113019 | 40 | 2.09 (A) |
| pDAB113018 | 37 | 1.30 (B) |

*Levels not connected by same letter are significantly different.

The protein and RNA expression analysis of immature tassel in V8 stage showed significant down regulation of both AAD1 mRNA and protein in transgenic plants expressing AAD-1 mRNA containing an miR529 target site (plasmids pDAB113018, pDAB113019, and pDAB113020), when compared to tissues producing AAD-1 mRNA with no target site (pDAB113021). (Table 14) There was a similar level of AAD1 reduction in plants transformed with pDAB113018 and pDAB113020, which confirms that AAD1 down regulation in immature tassel was due to miR529 and mutation made in the miRNA binding site of construct pDAB113020 did not affect the binding of miR529. There was significant but limited down regulation of AAD1 in the plants transformed with pDAB113019, indicating that mutation in the miRNA binding site of construct pDAB113019 had some effect on miR529 binding. These results confirm that desired and precise down regulation of the transgene could be obtained by selected manipulations of binding sites of native miRNA. In leaf tissues of V8 plants, however, there was very little difference in either AAD-1 mRNA or protein accumulation between plants transformed with pDAB113019 and pDAB113020 containing a modified miR529 target site (Table 14).

TABLE 14

Ratio of AAD1 to EF1α mRNA levels,
and level of AAD1 Protein, in
Tassels and Leaves of $T_1$ Transgenic B104 Plants
at the V8 Growth Stage. Means were separated
using the Tukey-Kramer Test.

| Transforming Plasmid | Tassel | | Leaf | |
| | Mean mRNA Ratio | Protein** | Mean mRNA Ratio | Protein** |
|---|---|---|---|---|
| pDAB113021 (no target site) | 0.84 (A)* | 339 (A) | 0.86 (A) | 107.5 (A) |
| pDAB113019 | 0.54 (AB) | 188 (B) | 0.79 (AB) | 140.8 (A) |
| pDAB113020 | 0.33 (B) | 49.8 (C) | 0.96 (A) | 91.1 (A) |
| pDAB113018 | 0.31 (B) | 47.1 (C) | 0.45 (B) | 74.5 (A) |

*Levels not connected by same letter are significantly different.
**ng/mg total protein Similarly, there was slight or no down regulation of AAD1 in the immature ear in V12 stage plants, or in the leaves of R3 stage plants, transformed with the various constructs (Table 15). However, compared to the control "no miRNA target site" construct pDAB113021, there was a substantial reduction of AAD1 protein in the V6 root tissue of plants transformed with pDAB113018, pDAB113019, and pDAB113020 (Table 15). These results confirm that hat miR529 is not specifically expressed in the tassel tissue, but rather is expressed at some levels in V6 root stage resulting in substantial reduction of AAD1 protein.

TABLE 15

Levels of AAD1 Protein (ng/mg total protein) in Selected
Tissues of $T_1$ Transgenic B104 Plants at Three Growth Stages.
Means were separated using the Tukey-Kramer Test.

| Transforming Plasmid | Immature ear, V12 stage | Leaf, R3 stage | Root, V6 stage |
|---|---|---|---|
| pDAB113021 | 312.7 (AB) | 112.8 (AB)* | 163.6 (A) |
| pDAB113020 | 256.3 (B) | 119.4 (AB) | 102.9 (BC) |
| pDAB113019 | 296.3 (AB) | 137.6 (A) | 137.4 (AB) |
| pDAB113018 | 408.9 (A) | 74.7 (B) | 51.4 (C) |

Example 8: Herbicide-induced Control of Pollen Production and Male Sterility Five transgenic maize $T_0$ events of line B104 were produced by Agrobacterium-mediated transformation with plasmid pDAB109812, essentially as provided in EXAMPLE 4, and grown in the greenhouse. Null negative control plants (no AAD1 gene) and isoline positive control plants (in which AAD1 mRNA expression was driven by a copy of the maize ubiquitin 1 promoter with associated intron 1, and terminated by a copy of a maize per5 3'UTR, both as described above) were planted at the same time.

Thirty T1 plants (derived by fertilization of the 5 To events with B104-derived pollen) were grown in the greenhouse and subjected to a selection spray of 70 g acid-equivalents per hectare (ae/ha) of Assure® II at about the V2 stage to remove null segregant plants and provide hemizygous plant survivors having a functional AAD1 gene. Assure® II contains active ingredient Quizalofop P-Ethyl Ethyl(R)-2-4-[4-6-chloroquinoxalin-2-yl oxy)-phenoxy] propionate, and is produced by Dupont™ Crop Protection, Wilmington, DE. The commercial product contains 0.88 lbs. active ingredient (ai) per gallon.)

Twelve hemizygous plants for each event were chosen, and at the time of tassel appearance the whorls were treated according to Table 16. Controls were treated in the same way. Plants were grown to maturity in individual 5-gallon pots. When the tassel was partially emerged, leaves surrounding the tassel were carefully removed by trimming. Tassels were sprayed with either a 1.143% (v/v) or 2.286% (v/v) of Assure® II solution containing 1.0% (v/v) crop oil concentrate (COC). COC is an emulsifiable refined paraffinic oil containing about 85% paraffinic oil and about 15% emulsifiers. Applications were accomplished by applying 8 bursts of spray (0.1 mL each) from a hand-held DeVilbiss bulb atomizer. This method distributed 0.8 mL treatment solution to the tassel, and provides the equivalent of 560 gm ai/ha and 1120 gm ai/ha, respectively, for the 1.143% and 2.286% solutions. Neighboring plants and tissues were shielded from spray drift.

TABLE 16

Distributions of treatments amongst
12 hemizygous T1 plants from
transgenic B104 events
previously selected for a
functional AAD1 gene (n = 12).

| Treatment* | No. Plants Treated |
|---|---|
| 0 (untreated) | 2 |
| 0 (1% COC Check) | 2 |

TABLE 16-continued

Distributions of treatments amongst
12 hemizygous T1 plants from
transgenic B104 events
previously selected for a
functional AAD1 gene (n = 12).

| Treatment* | No. Plants Treated |
|---|---|
| 560 | 4 |
| 1120 | 4 |

*g ae/ha Assure ® II

Tassel damage was characterized by visual assessment of tissue death as a percentage of total tassel tissue.

Leaf paint assessments were performed using the same solutions as were used on the tassel sprays. Leaf paints were applied on both sides of the midvein (without contacting the midvein) of a 4-inch segment located in the middle of the 4th oldest leaf, using a small sponge paint applicator.

Tassels, leaves and stalks were rated for injury after applications (Table 17 and Table 18). There was 100% tassel elimination for plants of four out of the five pDAB109812 (i.e., SCBV: AAD1) events, effectively inducing male sterility. Additionally, leaves and stalks of these plants were not damaged. Thus, the plants retained effective herbicide tolerance in the vegetative and female reproductive tissues. The positive control plants (maize ubiquitin1 promoter driving AAD1 expression) did not show any tassel or vegetative injury, demonstrating tissue-specific AAD1 expression with the SCBV promoter. The null control plants (no AAD1 gene) showed 100% tassel elimination and also vegetative injury, as expected.

TABLE 17

Summary of event data.

| Event | Plant | Treatment* | % Tassel Injury 12 DAA** | % Tassel Injury 20 DAA | Leaf Paint Stalk Injury 20 DAA |
|---|---|---|---|---|---|
| 109812[1]-019.001AJ | 1 | 0 (untreated) | 0 | 0 | NA** |
| | 2 | 0 (untreated) | 0 | 0 | NA |
| | 3 | 560 | 30 | 30 | No |
| | 4 | 560 | 20 | 30 | No |
| | 5 | 0 (COC check) | 0 | 0 | No |
| | 6 | 560 | 20 | 30 | No |
| | 7 | 560 | 20 | 30 | No |
| | 8 | 1120 | 30 | 30 | No |
| | 9 | 1120 | 10 | 20 | No |
| | 10 | 1120 | 30 | 70 | No |
| | 11 | 1120 | 10 | 20 | No |
| | 12 | 0 (COC check) | 0 | 0 | No |
| 109812[1]-009.001AJ | 1 | 0 (untreated) | 0 | 0 | |
| | 2 | 0 (untreated) | 0 | 0 | |
| | 3 | 0 (COC check) | 0 | 0 | No |
| | 4 | 0 (COC check) | 0 | 0 | No |
| | 5 | 560 | 30 | 100*** | No |
| | 6 | 560 | 40 | 100*** | No |
| | 7 | 560 | 30 | 30 | No |
| | 8 | 560 | 30 | 30 | No |
| | 9 | 1120 | 40 | 40 | No |
| | 10 | 1120 | 30 | 100*** | No |
| | 11 | 1120 | 30 | 30 | No |
| | 12 | 1120 | 30 | 30 | No |
| 109812[1]-005.001AJ | 1 | 0 (untreated) | 0 | 0 | |
| | 2 | 560 | 40 | 50 (delayed) | No |
| | 3 | 0 (COC check) | 0 | 0 | No |
| | 4 | 560 | 40 | 100*** | No |
| | 5 | 560 | 30 | 30 | No |
| | 6 | 560 | 30 | 40 | No |
| | 7 | 0 (COC check) | 30 | 0 | No |
| | 8 | 1120 | 30 | 100*** | No |
| | 9 | 1120 | 30 | 30 | No |
| | 10 | 1120 | 30 | 100*** | No |

TABLE 17-continued

| | | | Summary of event data. | | |
|---|---|---|---|---|---|
| Event | Plant | Treatment* | % Tassel Injury 12 DAA** | % Tassel Injury 20 DAA | Leaf Paint Stalk Injury 20 DAA |
| | 11 | 1120 | 30 | 30 | No |
| | 12 | NT** | NT | NT | NT |
| 109812[1]-010.001AJ | 1 | 0 (untreated) | 0 | 0 | |
| | 2 | 0 (untreated) | 0 | 0 | |
| | 3 | 560 | 30 | 30 | No |
| | 4 | 560 | 40 | 40 | No |
| | 5 | 0 (COC check) | 0 | 0 | No |
| | 6 | 560 | 30 | 30 | No |
| | 7 | 1120 | 90 | 100*** | Yes (ear only) |
| | 8 | 0 (COC check) | 0 | 0 | No |
| | 9 | 560 | 50 | 95 | No |
| | 10 | 1120 | 30 | 30 | No |
| | 11 | 1120 | 30 | 30 | No |
| | 12 | 1120 | 50 | 40 | No |
| 109812[1]-018.001AJ | 1 | 0 (untreated) | 0 | 0 | |
| | 2 | 0 (COC check) | 0 | 0 | No |
| | 3 | 0 (COC check) | 0 | 0 | No |
| | 4 | 560 | 30 | 85 | No |
| | 5 | 560 | 30 | 30 | No |
| | 6 | 560 | 0 | 0 | No |
| | 7 | 1120 | 30 | 30 | No |
| | 8 | 560 | 50 | 100† | No |
| | 9 | 1120 | 30 | 30 | No |
| | 10 | 1120 | 20 | 50 | No |
| | 11 | 1120 | 20 | 30 | No |
| | 12 | NT | NT | NT | |

*g ai/ha Assure ® II

**DAA = Days After Application; NA = Not Applicable; NT = Not Tested

***Tassel was necrotic and did not expand

†Tassel and top leaves died

TABLE 18

| | | | Summary of control plant data. | | |
|---|---|---|---|---|---|
| Source ID | Treatment* | % Tassel Injury 7 DAA | Leaf Paint Symptoms 7 DAA | % Tassel Injury 12 DAA | % Tassel Injury 22 DAA | Leaf Paint Stalk Injury 22 DAA |
| | | | Null (No AAD1 gene) | | | |
| 1 | 560 | 30 | Yes | 70 | 100 | Yes |
| 2 | 560 | 20 | Yes | 50 | 100 | Yes |
| 3 | 560 | 40 | No | 60 | 100 | Yes |
| 4 | 560 | 50 | Yes | 70 | 100 | Yes |
| 5 | 1120 | 40 | No | 70 | 100 | Yes |
| 6 | Untreated | 0 | | 0 | 0 | No |
| 7 | 1120 | 50 | Yes | 70 | 100 | Yes |
| 8 | 1120 | 20 | No | 30 | 90 | Yes |
| 9 | Untreated | 0 | | 0 | 0 | No |
| 10 | Untreated | 0 | | 0 | 0 | No |
| 11 | 1120 | 30 | Yes | 50 | 90 | Yes |
| 12 | Untreated | 0 | | 0 | 0 | No |
| | | Positive control (High AAD1 expression) | | | | |
| 1 | 560 | 0 | Yes | 0 | 0 | No |
| 2 | 560 | 0 | Yes | 0 | 0 | No |
| 3 | 560 | 0 | Yes | 0 | 0 | No |
| 4 | 560 | 0 | No | 0 | 0 | No |
| 5 | Untreated | 0 | | 0 | 0 | No |
| 6 | Untreated | 0 | | 0 | 0 | No |
| 7 | 1120 | 0 | Yes | 0 | 0 | No |
| 8 | 1120 | 0 | Yes | 0 | 0 | No |
| 9 | Untreated | 0 | | 0 | 0 | No |
| 10 | 1120 | 0 | No | 0 | 0 | No |

TABLE 18-continued

Summary of control plant data.

| Source ID | Treatment* | % Tassel Injury 7 DAA | Leaf Paint Symptoms 7 DAA | % Tassel Injury 12 DAA | % Tassel Injury 22 DAA | Leaf Paint Stalk Injury 22 DAA |
|---|---|---|---|---|---|---|
| 11 | Untreated | 0 | | 0 | 0 | No |
| 12 | 1120 | 0 | Yes | 0 | 0 | No |

*g ai/ha Assure ® II
**DAA = Days After Application;
NA = Not Applicable;
NT = Not Tested
***Tassel was necrotic and did not expand
†Tassel and top leaves died In summary, the data show that a timed and directed application of Assure® II to SCBV: AAD1 plants can effectively kill male reproductive tissue, whilst still providing vegetative tolerance.

Example 9: Herbicide-induced Male Sterile Hybridization System

Transgenic maize plants are produced that have been transformed with an AAD1 gene under the control of a plant promoter and other plant expression regulatory elements. Inherent to the AAD1 mRNA is a target site sequence recognized, for example, by an miRNA (e.g., miR156, miR529, and miR319). It is advantageous that native expression of the miRNA whose target site is introduced into the AAD1 mRNA is detected in tissues or cells comprising the immature tassel, including the palea, lemma, stamen, filament, anther, microspores, male gametophyte, sperm cell, tube cell, or other cells that affect or control pollen development, although expression may also be detected in ear and root tissue (Chuck et al. (2010) *Development* 137:1243-50; Zhang et al. (2009) *PloS Genetics November* 5).

It is additionally advantageous that the promoter used to control expression of the AAD1 mRNA be one that is inactive or only weakly functional in tissues or cells comprising the immature tassel, including the palea, lemma, stamen, filament, anther, microspores, male gametophyte, sperm cell, tube cell, or other cells that affect or control pollen development and production.

It is further advantageous that expression of AAD1 mRNA in other plant parts not directly involved in pollen production (such as leaves, roots, stems, developing ears, silks, etc.) is sufficient to produce an AAD1 protein accumulation to levels sufficient to confer tolerance of those tissues to growth inhibitory levels of herbicidal compounds that are substrates for AAD1, such that those tissues are not damaged or otherwise detrimentally affected by application (for example, by spraying) of the herbicide compounds. Application of inhibitory levels of herbicidal compounds that are substrates for AAD1 to plants at an early stage of tassel development inhibits or prevents tassel and pollen development and thus produces a male sterile plant. Further, the development, growth, morphology, maturity and yield of such plants are not affected by treatment with the herbicidal compounds.

Example 10: Stereospecific Herbicide-induced Male Sterile Hybridization Systems Transgenic maize plants having an AAD1 transgene are produced, in which expression of the AAD1 transgene is under the control of constitutive plant expression regulatory elements, such as the maize ubiquitin1 promoter with associated intron 1. Such AAD1 plants are secondarily transformed with a plant expression cassette comprising an AAD12 coding region (U.S. Pat. No. 8,283,522) under the control of a promoter and other plant expression regulatory elements that are chosen such that AAD12 transgene expression and accumulation of the AAD12 protein occur exclusively in male reproductive tissues (for example, immature tassel, palea, lemma, stamen, filament, anther, microspores, male gametophyte, sperm cell, tube cell, or other cells that affect or control pollen development and production).

The AAD1 and AAD12 proteins utilize enantiomeric substrates (the R-form or the S-form, respectively) of compounds comprising a benzene ring, oxygen, and propionic acid. For example, the AAD12 protein can use as substrates 2,4-D (2,4-dichlorophenoxyacetic acid) and pyridyloxyacetate herbicidal compounds, whereas the AAD1 protein inactivates "fops," substrates such as Haloxyfop and Quizalofop. During hybrid seed production female rows (containing plants to be used as pollen acceptors) are sprayed at an early tassel stage (before pollen shed) with an herbicidal compound analog (pro-herbicide S-form) that is a specific substrate for AAD12, whilst the male rows (containing plants to be used as pollen donors) are not sprayed.

The activity of AAD12 protein in the male tissues of the sprayed plants converts the S-form pro-herbicidal compound into an active herbicidal compound, which results in destruction of the male tissues and thus induces male sterility. The other tissues of the sprayed plants (as a result of AAD1 protein production and the lack of AAD12 production in those tissues) are not affected by the S-form pro-herbicidal compound and are further resistant to fops herbicidal compounds (for example, Haloxyfop and Quizalofop). Thus, weeds in the fields are controlled by the action of the fops herbicides. Subsequently, plants in unsprayed male rows are able to produce pollen and to pollinate plants in female rows to create hybrid seed. The method avoids yield loss due to plant damage that occurs during a machine or manual de-tasseling process, which becomes unnecessary when a herbicide-induced male sterility system is employed.

In some examples, an additional herbicide tolerance gene (such as a DGT gene (U.S. Patent Application 61/593,555, filed Feb. 1, 2012)) is expressed throughout the whole plant, while an AAD12 gene is expressed exclusively in the male tissues, with the same end result of induction of male sterility upon application of the appropriate herbicidal compounds at the appropriate stages of plant development. Other herbicide tolerance genes are used in some examples.

In dicotyledonous plants, the roles of the AAD1 and AAD12 proteins is reversed, such that AAD12 would be constitutively expressed throughout the plant, while AAD1 expression would be male-tissue specific, and an R-form pro-herbicidal compound would be used to destroy male tissues.

What may be claimed is:

1. A transgenic plant cell comprising a recombinant polynucleotide that encodes an AAD-1 protein that exhibits aryloxyalkanoate dioxygenase activity, wherein said activity enzymatically degrades a phenoxy auxin herbicide and an (R)-aryloxyphenoxypropionate herbicide, wherein, an sRNA target site comprising SEQ ID NO:7, or SEQ ID NO:8 is operably linked to the nucleotide sequence encoding the protein encoded by base pairs 1-888 of SEQ ID NO: 5.

2. The plant cell of claim 1 wherein the sRNA target site is recognized by an endogenous sRNA of the plant cell.

3. The plant cell of claim 1 wherein said plant cell is a dicotyledonous or a monocotyledonous plant cell.

4. A transgenic plant comprising a plurality of the plant cells of claim 1, wherein expression of said polynucleotide renders said plant tolerant to an aryloxyalkanoate herbicide.

5. The plant of claim 4 wherein said aryloxyalkanoate herbicide is a phenoxy auxin herbicide.

6. The plant of claim 4 wherein said aryloxyalkanoate herbicide is selected from the group consisting of 2,4-dichlorophenoxyacetic acid, MCPA, dichlorprop, and mecoprop.

7. The plant of claim 4 wherein said aryloxyalkanoate herbicide is an (R)-aryloxyphenoxypropionate.

8. The plant of claim 4 wherein said aryloxyalkanoate herbicide is selected from the group consisting of (R)-fluazifop, (R)-haloxyfop, (R)-diclofop, (R)-quizalofop, (R)-fenoxaprop, (R)-metamifop, (R)-cyhalofop, and (R)-clodinofop.

9. The plant of claim 4 wherein expression of the AAD-1 protein is reduced or eliminated in at least one tissue of the plant as compared to tissues expressing an AAD-1 mRNA with no sRNA target site.

10. The plant of claim 4 wherein expression of the AAD-1 protein is reduced or eliminated in tissue-specific or tissue-preferred manner as compared to plants producing AAD-1 mRNA with no target site.

11. The plant of claim 4 wherein said plant further comprises a second herbicide resistance gene.

12. The plant of claim 11 wherein said phenoxy auxin herbicide is an R-enantiomer of a chiral phenoxy auxin.

13. The plant of claim 11 wherein said phenoxy auxin herbicide is an achiral phenoxy auxin selected from the group consisting of 2,4-D and MCPA.

14. The plant of claim 11 wherein said (R)-aryloxyphenoxypropionate herbicide is selected from the group consisting of (R)-fluazifop, (R)-haloxyfop, (R)-diclofop, (R)-quizalofop, (R)-fenoxaprop, (R)-metamifop, (R)-cyhalofop, and (R)-clodinofop.

15. A seed comprising a plurality of the plant cells of claim 1.

16. A method of controlling weeds in a field, wherein said method comprises applying an aryloxyalkanoate herbicide to said field and planting a seed of claim 15 in said field.

17. A part, progeny, or asexual propagate grown from the seed of claim 15, wherein said part, progeny, or asexual propagate comprises said polynucleotide.

* * * * *